(12) United States Patent
Markle et al.

(10) Patent No.: US 8,535,262 B2
(45) Date of Patent: *Sep. 17, 2013

(54) USE OF AN EQUILIBRIUM INTRAVASCULAR SENSOR TO ACHIEVE TIGHT GLYCEMIC CONTROL

(75) Inventors: William H. Markle, Laguna Niguel, CA (US); David R. Markle, Berwyn, PA (US)

(73) Assignee: Glumetrics, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/316,397

(22) Filed: Dec. 9, 2011

(65) Prior Publication Data

US 2012/0116191 A1    May 10, 2012

Related U.S. Application Data

(63) Continuation of application No. 12/274,617, filed on Nov. 20, 2008, now Pat. No. 8,088,097.

(60) Provisional application No. 60/989,732, filed on Nov. 21, 2007.

(51) Int. Cl.
*A61M 31/00* (2006.01)
(52) U.S. Cl.
USPC .......................................................... 604/66
(58) Field of Classification Search
USPC ...................... 604/65–67, 131–133; 514/765; 424/9.6, 1.11, 1.65, 9.1
See application file for complete search history.

(56) References Cited

U.S. PATENT DOCUMENTS

| | | | |
|---|---|---|---|
| 1,120,700 A | 12/1914 | Ehrlich |
| 1,334,901 A | 3/1920 | Higdon |
| 2,018,792 A | 10/1935 | Kern |
| 2,094,224 A | 9/1937 | Tietz et al. |
| 2,112,244 A | 3/1938 | Jurist |
| 2,274,551 A | 2/1942 | Kenyon et al. |
| 2,496,151 A | 1/1950 | Dawson et al. |
| 2,812,524 A | 11/1957 | Pruitt |

(Continued)

FOREIGN PATENT DOCUMENTS

| CN | 85108331 | 6/1987 |
|---|---|---|
| CS | 7707425 | 2/1980 |

(Continued)

OTHER PUBLICATIONS

"Optical Glucose Sensor Holds Promise for Diabetics and Intensive Care patients", Science Daily, Mar. 18, 2004. [Science daily Article].*

(Continued)

*Primary Examiner* — Manuel Mendez
(74) *Attorney, Agent, or Firm* — Knobbe Martens Olson & Bear, LLP

(57) ABSTRACT

A method for achieving tight glycemic control in a patient in need thereof is disclosed. The method comprises deploying an equilibrium glucose sensor within a blood vessel in the patient, coupling the sensor to a monitor that displays the blood glucose concentration, and administering a blood glucose regulator when the blood glucose concentration varies outside of the predetermined concentration range. The blood glucose regulator is administered in an amount sufficient to return the blood glucose concentration to within the predetermined concentration range, thereby achieving tight glycemic control.

34 Claims, 20 Drawing Sheets

(56) References Cited

U.S. PATENT DOCUMENTS

| | | |
|---|---|---|
| 3,011,293 A | 12/1961 | Rado |
| 3,302,219 A | 2/1967 | Harris |
| 3,488,098 A | 1/1970 | Sobczak |
| 3,659,586 A | 5/1972 | Johns et al. |
| 3,795,239 A | 3/1974 | Eberhard et al. |
| 3,827,089 A | 8/1974 | Grow |
| 3,846,353 A | 11/1974 | Grotta |
| 3,865,548 A | 2/1975 | Padawer |
| 3,874,010 A | 4/1975 | Geary |
| 3,884,225 A | 5/1975 | Witter |
| 3,895,403 A | 7/1975 | Davis |
| 3,905,888 A | 9/1975 | Mindt et al. |
| 3,909,504 A | 9/1975 | Browne |
| 3,924,281 A | 12/1975 | Gibbs |
| 3,930,580 A | 1/1976 | Bazell et al. |
| 3,996,345 A | 12/1976 | Ullman |
| 4,003,707 A | 1/1977 | Lübbers et al. |
| 4,041,932 A | 8/1977 | Fostick |
| 4,094,578 A | 6/1978 | DiVita et al. |
| 4,180,879 A | 1/1980 | Mann |
| 4,197,853 A | 4/1980 | Parker |
| 4,200,110 A | 4/1980 | Peterson et al. |
| 4,240,438 A | 12/1980 | Updike et al. |
| 4,245,645 A | 1/1981 | Arseneault et al. |
| 4,269,605 A | 5/1981 | Dean et al. |
| 4,306,562 A | 12/1981 | Osborne |
| 4,307,933 A | 12/1981 | Palmer et al. |
| 4,308,254 A | 12/1981 | Tayot et al. |
| 4,344,438 A | 8/1982 | Schultz |
| 4,345,606 A | 8/1982 | Littleford |
| 4,358,851 A | 11/1982 | Scilfres et al. |
| 4,361,918 A | 12/1982 | Roisseth |
| 4,371,374 A | 2/1983 | Cerami et al. |
| 4,459,712 A | 7/1984 | Pathan |
| 4,465,335 A | 8/1984 | Eppes |
| 4,469,357 A | 9/1984 | Martin |
| 4,474,431 A | 10/1984 | Bricheno |
| 4,476,870 A | 10/1984 | Peterson et al. |
| 4,490,867 A | 1/1985 | Gabrielson |
| 4,495,293 A | 1/1985 | Shaffar |
| 4,502,169 A | 3/1985 | Persson |
| RE31,879 E | 5/1985 | Lübbers et al. |
| 4,528,616 A | 7/1985 | Koppensteiner |
| 4,548,907 A | 10/1985 | Seitz et al. |
| 4,557,900 A | 12/1985 | Heitzmann |
| 4,560,248 A | 12/1985 | Cramp et al. |
| 4,568,444 A | 2/1986 | Nakamura et al. |
| 4,600,310 A | 7/1986 | Cramp et al. |
| 4,621,049 A | 11/1986 | Wang |
| 4,629,451 A | 12/1986 | Winters et al. |
| 4,636,144 A | 1/1987 | Abe et al. |
| 4,649,271 A | 3/1987 | Hök et al. |
| 4,650,472 A | 3/1987 | Bates |
| 4,654,031 A | 3/1987 | Lentz |
| 4,654,127 A | 3/1987 | Baker et al. |
| 4,654,327 A | 3/1987 | Teng |
| 4,659,817 A | 4/1987 | Gallop et al. |
| 4,675,925 A | 6/1987 | Littleton |
| 4,684,538 A | 8/1987 | Klemarczyk |
| 4,689,308 A | 8/1987 | Gerhard |
| RE32,514 E | 10/1987 | Steklenski |
| 4,703,756 A | 11/1987 | Gough et al. |
| 4,707,056 A | 11/1987 | Bittner |
| 4,710,623 A | 12/1987 | Lipson et al. |
| 4,727,730 A | 3/1988 | Boiarski et al. |
| 4,737,153 A | 4/1988 | Shimamura et al. |
| 4,744,618 A | 5/1988 | Mahlein |
| 4,746,751 A | 5/1988 | Oviatt |
| 4,750,795 A | 6/1988 | Blotekjaer |
| 4,751,918 A | 6/1988 | Bernard et al. |
| 4,754,538 A | 7/1988 | Stewart, Jr. et al. |
| 4,776,047 A | 10/1988 | DiMatteo |
| 4,785,814 A | 11/1988 | Kane |
| 4,792,689 A | 12/1988 | Peterson |
| 4,794,619 A | 12/1988 | Tregay |
| 4,796,633 A | 1/1989 | Zwirkoski |
| 4,798,738 A | 1/1989 | Yafuso et al. |
| 4,801,187 A | 1/1989 | Elbert et al. |
| 4,803,049 A | 2/1989 | Hirschfeld et al. |
| 4,810,655 A | 3/1989 | Khalil et al. |
| 4,816,130 A | 3/1989 | Karakelle et al. |
| 4,820,636 A | 4/1989 | Hill et al. |
| 4,821,738 A | 4/1989 | Iwasaki et al. |
| 4,822,127 A | 4/1989 | Kamiya et al. |
| 4,833,091 A | 5/1989 | Leader et al. |
| 4,838,269 A | 6/1989 | Robinson et al. |
| 4,844,841 A | 7/1989 | Koller et al. |
| 4,846,543 A | 7/1989 | Kapany et al. |
| 4,851,195 A | 7/1989 | Matthews et al. |
| 4,854,321 A | 8/1989 | Boiarski |
| 4,861,728 A | 8/1989 | Wagner |
| 4,872,226 A | 10/1989 | Lonardo |
| 4,872,759 A | 10/1989 | Stich-Baumeister |
| 4,886,338 A | 12/1989 | Yafuso et al. |
| 4,889,407 A | 12/1989 | Markle et al. |
| 4,903,707 A | 2/1990 | Knute et al. |
| 4,906,232 A | 3/1990 | Reynolds |
| 4,923,273 A | 5/1990 | Taylor |
| 4,927,222 A | 5/1990 | Kamiya et al. |
| 4,937,901 A | 7/1990 | Brennan |
| 4,939,801 A | 7/1990 | Schaal et al. |
| 4,941,308 A | 7/1990 | Grabenkort et al. |
| 4,943,364 A | 7/1990 | Koch et al. |
| 4,946,038 A | 8/1990 | Eaton |
| 4,955,862 A | 9/1990 | Sepetka |
| 4,960,412 A | 10/1990 | Fink |
| 4,966,597 A | 10/1990 | Cosman |
| 5,000,901 A | 3/1991 | Iyer et al. |
| 5,005,576 A | 4/1991 | Günther |
| 5,007,704 A | 4/1991 | McCartney |
| 5,012,809 A | 5/1991 | Shulze |
| 5,018,225 A | 5/1991 | Fergni et al. |
| 5,030,420 A | 7/1991 | Bacon |
| 5,047,020 A | 9/1991 | Hsu |
| 5,047,208 A | 9/1991 | Schweitzer et al. |
| 5,047,627 A | 9/1991 | Yim et al. |
| 5,054,497 A | 10/1991 | Kapp et al. |
| 5,068,931 A | 12/1991 | Smith |
| 5,069,674 A | 12/1991 | Fearnot et al. |
| 5,082,112 A | 1/1992 | Dunklee |
| 5,093,266 A | 3/1992 | Leader et al. |
| 5,098,618 A | 3/1992 | Zelez |
| 5,104,388 A | 4/1992 | Quackenbush |
| 5,108,502 A | 4/1992 | Pawlowski et al. |
| 5,109,452 A | 4/1992 | Selvin et al. |
| 5,114,676 A | 5/1992 | Leiner et al. |
| 5,119,463 A | 6/1992 | Vurek |
| 5,132,432 A | 7/1992 | Haugland et al. |
| 5,137,033 A | 8/1992 | Norton |
| 5,137,833 A | 8/1992 | Russell |
| 5,141,497 A | 8/1992 | Erskine |
| 5,156,962 A | 10/1992 | Suzuki et al. |
| 5,162,130 A | 11/1992 | McLaughlin |
| 5,166,990 A | 11/1992 | Riccitelli et al. |
| 5,167,715 A | 12/1992 | Kalafala et al. |
| 5,168,587 A | 12/1992 | Shutes |
| 5,175,016 A | 12/1992 | Yafuso et al. |
| 5,176,882 A | 1/1993 | Gray et al. |
| 5,178,267 A | 1/1993 | Grabenkort et al. |
| 5,180,376 A | 1/1993 | Fischell |
| 5,182,353 A | 1/1993 | Hui et al. |
| 5,185,263 A | 2/1993 | Kroneis et al. |
| 5,188,803 A | 2/1993 | Hochberg |
| 5,217,691 A | 6/1993 | Greene et al. |
| 5,230,031 A | 7/1993 | Markle |
| 5,246,109 A | 9/1993 | Markle et al. |
| 5,246,441 A | 9/1993 | Ross et al. |
| 5,257,338 A | 10/1993 | Markle |
| 5,262,037 A | 11/1993 | Markle et al. |
| 5,279,596 A | 1/1994 | Castaneda et al. |
| 5,280,130 A | 1/1994 | Markle et al. |
| 5,280,548 A | 1/1994 | Atwater et al. |
| 5,284,154 A | 2/1994 | Raymond et al. |
| 5,286,294 A | 2/1994 | Ebi et al. |

| | | | |
|---|---|---|---|
| 5,290,266 A | 3/1994 | Rohling et al. | |
| 5,302,731 A | 4/1994 | Pitner et al. | |
| 5,305,740 A | 4/1994 | Kolobow | |
| 5,310,471 A | 5/1994 | Markle et al. | |
| 5,312,344 A | 5/1994 | Grinfeld | |
| 5,322,513 A | 6/1994 | Walker | |
| 5,330,718 A | 7/1994 | Hui et al. | |
| 5,334,157 A | 8/1994 | Klein et al. | |
| 5,335,305 A | 8/1994 | Kosa et al. | |
| 5,354,448 A | 10/1994 | Markle et al. | |
| 5,357,732 A | 10/1994 | Markle et al. | |
| 5,361,758 A | 11/1994 | Hall et al. | |
| 5,380,304 A | 1/1995 | Parker | |
| 5,389,217 A | 2/1995 | Singer | |
| 5,408,999 A | 4/1995 | Singh et al. | |
| 5,409,469 A | 4/1995 | Schaerf | |
| 5,503,770 A * | 4/1996 | James et al. | 252/301.16 |
| 5,511,408 A | 4/1996 | Yoshioka et al. | |
| 5,511,547 A | 4/1996 | Markle et al. | |
| 5,512,246 A | 4/1996 | Russell et al. | |
| 5,514,710 A | 5/1996 | Haugland et al. | |
| 5,536,783 A | 7/1996 | Olstein et al. | |
| 5,545,179 A | 8/1996 | Williamson, IV | |
| 5,558,714 A | 9/1996 | Watanabe et al. | |
| 5,569,186 A | 10/1996 | Lord et al. | |
| 5,596,988 A | 1/1997 | Markle et al. | |
| 5,605,152 A | 2/1997 | Slate et al. | |
| 5,618,587 A | 4/1997 | Markle et al. | |
| 5,622,259 A | 4/1997 | Church | |
| 5,634,911 A | 6/1997 | Hermann et al. | |
| 5,643,212 A | 7/1997 | Coutre et al. | |
| 5,643,580 A | 7/1997 | Subramaniam | |
| 5,658,264 A | 8/1997 | Samson | |
| 5,669,920 A | 9/1997 | Conley et al. | |
| 5,676,784 A | 10/1997 | McGaffigan | |
| D388,418 S | 12/1997 | Polson et al. | |
| 5,700,253 A | 12/1997 | Parker | |
| 5,702,373 A | 12/1997 | Samson | |
| 5,747,666 A | 5/1998 | Willis | |
| 5,755,704 A | 5/1998 | Lunn | |
| 5,763,238 A | 6/1998 | James et al. | |
| 5,797,876 A | 8/1998 | Spears et al. | |
| 5,810,985 A | 9/1998 | Bao et al. | |
| 5,827,242 A | 10/1998 | Follmer et al. | |
| 5,891,100 A | 4/1999 | Fleckenstein | |
| 5,891,114 A | 4/1999 | Chien et al. | |
| 5,922,612 A | 7/1999 | Alder et al. | |
| 5,947,940 A | 9/1999 | Beisel | |
| 5,951,929 A | 9/1999 | Wilson | |
| 5,954,651 A | 9/1999 | Berg et al. | |
| 6,002,954 A * | 12/1999 | Van Antwerp et al. | 600/317 |
| 6,011,984 A | 1/2000 | Van Antwerp et al. | |
| 6,019,736 A | 2/2000 | Avellanet et al. | |
| 6,117,290 A | 9/2000 | Say et al. | |
| 6,152,933 A | 11/2000 | Werp et al. | |
| 6,156,010 A | 12/2000 | Kuracina et al. | |
| 6,175,752 B1 * | 1/2001 | Say et al. | 600/345 |
| 6,187,130 B1 | 2/2001 | Berard et al. | |
| 6,197,534 B1 | 3/2001 | Lakowicz et al. | |
| 6,200,301 B1 | 3/2001 | Pfeiffer et al. | |
| 6,227,627 B1 | 5/2001 | Goossens | |
| 6,254,829 B1 | 7/2001 | Hartmann et al. | |
| 6,273,874 B1 | 8/2001 | Parris | |
| 6,304,766 B1 | 10/2001 | Colvin, Jr. | |
| 6,319,540 B1 | 11/2001 | Van Antwerp et al. | |
| 6,361,508 B1 | 3/2002 | Johnson et al. | |
| 6,363,273 B1 | 3/2002 | Mastrorio et al. | |
| 6,370,406 B1 | 4/2002 | Wach et al. | |
| 6,375,627 B1 | 4/2002 | Mauze | |
| 6,387,672 B1 * | 5/2002 | Arimori et al. | 435/183 |
| 6,464,849 B1 | 10/2002 | Say et al. | |
| 6,477,395 B2 | 11/2002 | Shulman et al. | |
| 6,521,447 B2 | 2/2003 | Zou et al. | |
| 6,544,212 B2 | 4/2003 | Galley et al. | |
| 6,584,335 B1 | 6/2003 | Haar et al. | |
| 6,585,665 B1 | 7/2003 | Chapman et al. | |
| 6,602,702 B1 | 8/2003 | McDevitt et al. | |
| 6,623,490 B1 | 9/2003 | Crane et al. | |
| 6,627,177 B2 | 9/2003 | Singaram et al. | |
| 6,653,141 B2 | 11/2003 | Singaram et al. | |
| 6,663,595 B2 | 12/2003 | Spohn et al. | |
| 6,682,938 B1 * | 1/2004 | Satcher et al. | 436/172 |
| 6,702,972 B1 | 3/2004 | Markle | |
| 6,711,423 B2 | 3/2004 | Colvin | |
| 6,741,877 B1 | 5/2004 | Shults et al. | |
| 6,766,183 B2 | 7/2004 | Walsh et al. | |
| 6,794,195 B2 | 9/2004 | Colvin | |
| 6,800,451 B2 | 10/2004 | Daniloff et al. | |
| 6,804,544 B2 | 10/2004 | Van Antwerp et al. | |
| 6,855,556 B2 | 2/2005 | Amiss et al. | |
| 6,858,403 B2 | 2/2005 | Han et al. | |
| 7,033,322 B2 | 4/2006 | Silver | |
| 7,064,103 B2 | 6/2006 | Pitner et al. | |
| D525,632 S | 7/2006 | Jost et al. | |
| RE39,438 E | 12/2006 | Shah et al. | |
| 7,181,260 B2 | 2/2007 | Gutierrez | |
| 7,216,001 B2 | 5/2007 | Hacker et al. | |
| D544,871 S | 6/2007 | Lim et al. | |
| 7,226,414 B2 | 6/2007 | Ballerstadt | |
| 7,229,450 B1 | 6/2007 | Chitre et al. | |
| D550,242 S | 9/2007 | Niijima | |
| D550,245 S | 9/2007 | Niijima | |
| 7,276,029 B2 | 10/2007 | Goode, Jr. et al. | |
| 7,277,740 B2 | 10/2007 | Rohleder et al. | |
| 7,277,745 B2 | 10/2007 | Natarajan et al. | |
| 7,303,814 B2 | 12/2007 | Lamberti et al. | |
| 7,306,621 B1 | 12/2007 | Halla et al. | |
| D559,264 S | 1/2008 | Niijima | |
| D560,224 S | 1/2008 | Park et al. | |
| 7,316,909 B2 | 1/2008 | Pitner et al. | |
| 7,317,111 B2 | 1/2008 | Bhatt et al. | |
| D610,065 S | 2/2008 | Park et al. | |
| 7,326,538 B2 | 2/2008 | Pitner et al. | |
| 7,345,160 B2 | 3/2008 | Daunert et al. | |
| 7,353,055 B2 | 4/2008 | Hogan | |
| 7,358,094 B2 | 4/2008 | Bell et al. | |
| 7,381,184 B2 | 6/2008 | Funderburk et al. | |
| 7,381,938 B2 | 6/2008 | Kobayashi et al. | |
| 7,390,462 B2 | 6/2008 | Rao et al. | |
| 7,417,164 B2 | 8/2008 | Suri | |
| D580,950 S | 11/2008 | Steele et al. | |
| D582,939 S | 12/2008 | Neuhaus | |
| 7,470,420 B2 | 12/2008 | Singaram et al. | |
| 7,496,392 B2 | 2/2009 | Alarcon et al. | |
| D592,223 S | 5/2009 | Neuhaus | |
| 7,559,894 B2 | 7/2009 | McEowen | |
| 7,615,007 B2 | 11/2009 | Shults et al. | |
| 7,661,301 B2 | 2/2010 | Moor | |
| 7,751,863 B2 | 7/2010 | Markle et al. | |
| 7,767,846 B2 | 8/2010 | Suri | |
| D626,143 S | 10/2010 | Karten et al. | |
| 7,824,918 B2 | 11/2010 | Suri | |
| 7,829,341 B2 | 11/2010 | Gamsey et al. | |
| 7,879,024 B2 | 2/2011 | Thorstenson et al. | |
| 7,939,664 B2 | 5/2011 | Gamsey et al. | |
| 7,959,577 B2 | 6/2011 | Schmitz et al. | |
| 7,981,058 B2 | 7/2011 | Akay | |
| 8,088,097 B2 * | 1/2012 | Markle et al. | 604/66 |
| 8,110,251 B2 | 2/2012 | Markle et al. | |
| 8,178,676 B2 | 5/2012 | Gamsey et al. | |
| 8,202,731 B2 | 6/2012 | Suri | |
| 8,467,843 B2 | 6/2013 | Markle et al. | |
| 8,473,222 B2 | 6/2013 | Romey et al. | |
| 2001/0016682 A1 | 8/2001 | Berner et al. | |
| 2002/0018843 A1 | 2/2002 | Van Antwerp et al. | |
| 2002/0026110 A1 | 2/2002 | Colvin, Jr. | |
| 2002/0107178 A1 * | 8/2002 | Van Den Berghe | 514/3 |
| 2002/0128546 A1 * | 9/2002 | Silver | 600/365 |
| 2002/0193672 A1 | 12/2002 | Walsh et al. | |
| 2003/0013974 A1 | 1/2003 | Natarajan et al. | |
| 2003/0028089 A1 | 2/2003 | Galley et al. | |
| 2003/0065254 A1 | 4/2003 | Schulman et al. | |
| 2003/0100821 A1 | 5/2003 | Heller et al. | |
| 2003/0171666 A1 | 9/2003 | Loeb | |
| 2003/0232198 A1 | 12/2003 | Lamberti et al. | |
| 2003/0232383 A1 | 12/2003 | Daunert et al. | |
| 2004/0028612 A1 | 2/2004 | Singaram et al. | |
| 2004/0072358 A1 | 4/2004 | Ballerstadt | |

| | | |
|---|---|---|
| 2004/0077969 A1 | 4/2004 | Onda et al. |
| 2004/0087842 A1 | 5/2004 | Lakowicz et al. |
| 2004/0136924 A1 | 7/2004 | Boyd et al. |
| 2004/0176672 A1 | 9/2004 | Silver et al. |
| 2004/0219535 A1 | 11/2004 | Bell et al. |
| 2004/0230138 A1 | 11/2004 | Inoue et al. |
| 2004/0243018 A1 | 12/2004 | Organ et al. |
| 2004/0260158 A1 | 12/2004 | Hogan |
| 2004/0260162 A1 | 12/2004 | Rohleder et al. |
| 2004/0267203 A1 | 12/2004 | Potter et al. |
| 2005/0019219 A1 | 1/2005 | Oshiman et al. |
| 2005/0048121 A1 | 3/2005 | East et al. |
| 2005/0054975 A1 | 3/2005 | Patel et al. |
| 2005/0059097 A1 | 3/2005 | Daunert et al. |
| 2005/0090014 A1* | 4/2005 | Rao et al. .................. 436/166 |
| 2005/0113658 A1 | 5/2005 | Jacobson et al. |
| 2005/0118599 A1 | 6/2005 | Pawliszyn |
| 2005/0118726 A1 | 6/2005 | Schultz et al. |
| 2005/0123935 A1 | 6/2005 | Haugland et al. |
| 2005/0124896 A1 | 6/2005 | Richter et al. |
| 2005/0130249 A1 | 6/2005 | Parris et al. |
| 2005/0173245 A1 | 8/2005 | Feldman et al. |
| 2005/0193860 A1 | 9/2005 | Schulman et al. |
| 2005/0233465 A1 | 10/2005 | Miller |
| 2005/0240086 A1 | 10/2005 | Akay |
| 2005/0241959 A1 | 11/2005 | Ward et al. |
| 2005/0266038 A1 | 12/2005 | Glauser et al. |
| 2005/0267326 A1 | 12/2005 | Loeb et al. |
| 2005/0282225 A1 | 12/2005 | Daunert et al. |
| 2005/0283204 A1 | 12/2005 | Buhlmann et al. |
| 2006/0008500 A1 | 1/2006 | Chavan et al. |
| 2006/0039950 A1 | 2/2006 | Zhou et al. |
| 2006/0051874 A1 | 3/2006 | Reed et al. |
| 2006/0079740 A1 | 4/2006 | Silver et al. |
| 2006/0083688 A1* | 4/2006 | Singaram et al. .................. 424/9.6 |
| 2006/0084854 A1 | 4/2006 | Cho et al. |
| 2006/0088722 A1 | 4/2006 | Aller et al. |
| 2006/0105174 A1 | 5/2006 | Aller et al. |
| 2006/0135888 A1 | 6/2006 | Mimnagh-Kelleher et al. |
| 2006/0173252 A1 | 8/2006 | Ellingsen et al. |
| 2006/0189863 A1 | 8/2006 | Peyser et al. |
| 2006/0189979 A1 | 8/2006 | Esch et al. |
| 2006/0195042 A1 | 8/2006 | Flahert |
| 2006/0270949 A1 | 11/2006 | Mathie et al. |
| 2006/0287600 A1 | 12/2006 | McEowen |
| 2007/0003588 A1 | 1/2007 | Chinn et al. |
| 2007/0014726 A1 | 1/2007 | Merical et al. |
| 2007/0020181 A1 | 1/2007 | Workman et al. |
| 2007/0038155 A1 | 2/2007 | Kelly, Jr. et al. |
| 2007/0060872 A1 | 3/2007 | Hall et al. |
| 2007/0100356 A1 | 5/2007 | Lucatero et al. |
| 2007/0123775 A1 | 5/2007 | Meyer et al. |
| 2007/0136825 A1 | 6/2007 | Frommer et al. |
| 2007/0156079 A1 | 7/2007 | Brown |
| 2007/0175828 A1 | 8/2007 | Goedje et al. |
| 2007/0179437 A1 | 8/2007 | Grage et al. |
| 2007/0207498 A1 | 9/2007 | Palmieri et al. |
| 2007/0244382 A1 | 10/2007 | Robinson et al. |
| 2007/0256477 A1 | 11/2007 | Moor |
| 2007/0265675 A1 | 11/2007 | Lund et al. |
| 2008/0001091 A1 | 1/2008 | Kobayashi et al. |
| 2008/0009687 A1 | 1/2008 | Smith et al. |
| 2008/0027245 A1 | 1/2008 | Suri |
| 2008/0086042 A1 | 4/2008 | Brister et al. |
| 2008/0154107 A1 | 6/2008 | Jina |
| 2008/0183061 A1 | 7/2008 | Goode et al. |
| 2008/0187655 A1 | 8/2008 | Markle et al. |
| 2008/0188722 A1 | 8/2008 | Markle et al. |
| 2008/0188725 A1 | 8/2008 | Markle et al. |
| 2008/0261255 A1 | 10/2008 | Tolosa et al. |
| 2008/0287761 A1 | 11/2008 | Hayter et al. |
| 2008/0305009 A1 | 12/2008 | Gamsey et al. |
| 2008/0305506 A1 | 12/2008 | Suri |
| 2008/0306363 A1 | 12/2008 | Chaiken et al. |
| 2008/0311675 A1 | 12/2008 | Thomas et al. |
| 2009/0018418 A1 | 1/2009 | Markle et al. |
| 2009/0018426 A1 | 1/2009 | Markle et al. |
| 2009/0048430 A1 | 2/2009 | Hellinga et al. |
| 2009/0061528 A1 | 3/2009 | Suri |
| 2009/0062696 A1 | 3/2009 | Nathan et al. |
| 2009/0076336 A1 | 3/2009 | Mazar et al. |
| 2009/0081803 A1 | 3/2009 | Gamsey et al. |
| 2009/0082566 A1 | 3/2009 | Mitra |
| 2009/0088329 A1 | 4/2009 | Brennan et al. |
| 2009/0104714 A1 | 4/2009 | Thomas et al. |
| 2009/0112075 A1 | 4/2009 | Klok et al. |
| 2009/0143659 A1 | 6/2009 | Li et al. |
| 2009/0171381 A1 | 7/2009 | Schmitz et al. |
| 2009/0177143 A1 | 7/2009 | Markle et al. |
| 2009/0182217 A1 | 7/2009 | Li et al. |
| 2009/0192416 A1 | 7/2009 | Ernst et al. |
| 2009/0196864 A1 | 8/2009 | Bulla |
| 2009/0200620 A1 | 8/2009 | Omura et al. |
| 2009/0228068 A1 | 9/2009 | Buhlmann et al. |
| 2009/0264719 A1 | 10/2009 | Markle et al. |
| 2009/0275815 A1 | 11/2009 | Bickoff et al. |
| 2009/0324945 A1 | 12/2009 | Licht et al. |
| 2010/0173065 A1 | 7/2010 | Michal et al. |
| 2010/0274110 A1 | 10/2010 | Markle |
| 2010/0279424 A1 | 11/2010 | Suri |
| 2010/0292617 A1 | 11/2010 | Lei et al. |
| 2010/0312483 A1 | 12/2010 | Peyser |
| 2011/0077477 A1 | 3/2011 | Romey |
| 2011/0105866 A1 | 5/2011 | Markle |
| 2011/0152658 A1 | 6/2011 | Peyser |
| 2011/0171742 A1 | 7/2011 | Gamsey |
| 2011/0224516 A1 | 9/2011 | Romey et al. |
| 2011/0236989 A1 | 9/2011 | Suri et al. |
| 2011/0263953 A1 | 10/2011 | Markle |
| 2012/0053427 A1 | 3/2012 | Markle |
| 2012/0208286 A1 | 8/2012 | Gamsey et al. |
| 2012/0282412 A1 | 11/2012 | Markle |

FOREIGN PATENT DOCUMENTS

| | | |
|---|---|---|
| DE | 3036868 | 5/1982 |
| DE | 3509262 | 10/1985 |
| DE | 3720736 | 1/1989 |
| DE | 195 02 183 | 8/1996 |
| DE | 298 17 986 | 2/1999 |
| DE | 198 20 808 | 11/1999 |
| EP | 0 073 558 | 3/1983 |
| EP | 0 147 168 | 7/1985 |
| EP | 0 596 700 | 5/1994 |
| EP | 0 617 977 A1 | 10/1994 |
| EP | 0 758 451 B1 | 1/1999 |
| EP | 000760723-0001 | 7/2007 |
| EP | 2217316 | 7/2010 |
| EP | 2 222 686 | 8/2010 |
| EP | 2 147 003 | 4/2011 |
| EP | 2 054 476 | 6/2011 |
| FR | 2 350 831 | 12/1977 |
| FR | 2 624 007 | 6/1989 |
| GB | 1 123 094 | 8/1968 |
| GB | 1 447 163 | 8/1976 |
| GB | 2 048 682 | 12/1980 |
| JP | 53-68249 | 6/1978 |
| JP | 54-13347 | 1/1979 |
| JP | 54-111363 | 8/1979 |
| JP | 54-155856 | 12/1979 |
| JP | 56-116752 | 9/1981 |
| JP | 56-116754 | 9/1981 |
| JP | 58-162921 | 9/1983 |
| JP | 3-52936 | 3/1991 |
| JP | 06-016859 | 4/1994 |
| JP | 06-285049 | 10/1994 |
| JP | 2003-262613 | 9/2003 |
| JP | 1332866 | 5/2008 |
| JP | 2009-544729 | 12/2009 |
| JP | 2010-507711 | 3/2010 |
| JP | 2010-517693 | 5/2010 |
| JP | 2010-518397 | 5/2010 |
| JP | 2010-526599 | 8/2010 |
| JP | 2010-527010 | 8/2010 |
| JP | 2010-535903 | 11/2010 |
| JP | 2011-504399 | 2/2011 |
| JP | 2011-511755 | 4/2011 |
| SU | 6216724 | 8/1978 |
| WO | WO 87/00920 | 2/1987 |

| | | |
|---|---|---|
| WO | WO 88/04415 | 6/1988 |
| WO | WO 92/19150 | 11/1992 |
| WO | WO 94/10553 | 5/1994 |
| WO | WO 96/22730 | 8/1996 |
| WO | WO 96/22798 | 8/1996 |
| WO | WO 97/20530 | 6/1997 |
| WO | WO 97/37713 | 10/1997 |
| WO | WO 97/48437 | 12/1997 |
| WO | WO 98/08554 | 3/1998 |
| WO | WO 00/02048 | 1/2000 |
| WO | WO 00/13003 | 3/2000 |
| WO | WO 00/43536 | 7/2000 |
| WO | WO 01/20019 | 3/2001 |
| WO | WO 02/46752 | 6/2002 |
| WO | WO 03/034047 | 4/2003 |
| WO | WO 03/060464 | 7/2003 |
| WO | WO 2004/054438 | 7/2004 |
| WO | WO 2004/099778 A1 | 11/2004 |
| WO | WO 2005/090014 A1 | 4/2005 |
| WO | WO 2005/054831 | 6/2005 |
| WO | WO 2005/065241 | 7/2005 |
| WO | WO 2006/023725 | 3/2006 |
| WO | WO 2006/044973 | 4/2006 |
| WO | WO 2007/059311 | 5/2007 |
| WO | WO 2007/067743 | 6/2007 |
| WO | WO 2007/105140 | 9/2007 |
| WO | WO 2008/014280 | 1/2008 |
| WO | WO 2008/072338 | 6/2008 |
| WO | WO 2008/097747 | 8/2008 |
| WO | WO 2008/098011 | 8/2008 |
| WO | WO 2008/098087 | 8/2008 |
| WO | WO 2008/137604 | 11/2008 |
| WO | WO 2008/141241 | 11/2008 |
| WO | WO 2008/141243 | 11/2008 |
| WO | WO 2009/009756 | 1/2009 |
| WO | WO 2009/018426 | 1/2009 |
| WO | WO 2009/021057 | 2/2009 |
| WO | WO 2009/067626 | 5/2009 |
| WO | WO 2009/129186 | 10/2009 |
| WO | WO 2010/141888 | 9/2010 |
| WO | WO 2010/123972 | 10/2010 |
| WO | WO 2011/041546 | 4/2011 |
| WO | WO 2011/056274 | 5/2011 |
| WO | WO 2011/075710 | 6/2011 |
| WO | WO 2011/075711 | 6/2011 |
| WO | WO 2011/084713 | 7/2011 |
| WO | WO 2011/097586 | 8/2011 |
| WO | WO 2011/113020 | 9/2011 |
| WO | WO 2011/137178 | 11/2011 |
| WO | WO 2013/033076 | 3/2013 |
| WO | WO 2013/049068 | 4/2013 |

OTHER PUBLICATIONS

Check, William, "ICUs tighten belts on Blood Glucose Levels", in Cap Today, vol. 14, No. 2, Feb. 2005. [Check].*
WO 2000/043536, pub date: Jul. 27, 2000.*
WO 2008/001091, pub date: Jun. 28, 2007.*
Levetan et al., Hospital management of Diabetes, Pub date: Dec. 2000. [Levetan paper 2000].*
Furnary et al., Effect of hyperglycemia . . . surgical procedures, pub date: Mar./Apr. 2004. [Furnary paper 2004].*
Van der Berghe et al., "Intensive Insulin therapy in critically ill patients", pub date: Nov. 8, 2001. [Van der berghe paper 2001].*
Wilson et al., Intensive insulin therapy in critical care, pub date: Apr. 2007. [Wilson paper 2007].*
Agayn, V. I. and Dr. R. Walt (1993). "Fiber-optic sensor for continuous monitoring of fermentation pH." Biotechnology 72(6):6-9.
Angel, S. M., "Optrodes: Chemically Selective Fiber Optic Sensors," Spectroscopy, Apr. 1987, pp. 38-47.
Badugu R., et al, "Wavelength-ratiometric near-physiological pH sensors based on 6-aminoquinolinium boronic acid probes" Talanta, Elsevier, Amsterdam, NL, Apr. 30, 2005, vol. 66, Issue No. 3, pp. 569-574.
Badugu, R. et al. "Boronic acid fluorescents ensors for monosaccharide signaling based on the 6-methoxyquinolinium heterocyclic nucleus: progress toward noninvasive and continuous glucose monitoring." 2005 Bioorg. Med. Chem. 13 (1):113-119.
Badugu, R. et al. "Fluorescence sensors for monosaccharides based on the 6-methylquinolinium nucleus and boronic acid moiety: potential application to ophthalmic diagnostics." 2005 Talanta 65 (3):762-768.
Bean & Johnson, 54 J. Am. Chem. Soc. 4415 (1932).
Bolton C F. 1999 Acute Weakness. In: Oxford Textbook of Critical Care; Eds. Webb A R, Shapiro M J, Singer M, Suter P M; Oxford Medical Publications, Oxford UK; pp. 490-495.
Burnett, Peebles & Hageman, 96 Biochemical and Biophysical Research Communications 157 (1980).
Cappuccio, F.E. et al. 2004 "Evaluation of pyranine derivatives in boronic acid based saccharide sensing: Significance of charge interaction between dye and quencher in solution and hydrogel" Journal of Fluorescence 14:521-533.
Check, W., "ICUs tighten belts on blood glucose levels", Cap Today, Feb. 2005, in 7 pages, vol. 19-2.
Dawson, et al., 98 JACS 5996 (1970).
Definition of "cathether" from Webster's Ninth New Collegiate Dictionary, 1990, p. 216.
EPO Exam Report re EP App. No. 08 728 399.0, dated Dec. 7, 2010.
EPO Office Action re App. No. 07 799 791.4 dated Jan. 29, 2010.
European Examination dated Apr. 1, 2010, re EP Application No. 08 769 266.1-1211.
European Examination Report dated May 11, 2010, re EP Application No. 08 729 209.0.
European Examination Report re App. No. 08 797 302.0, dated Jan. 24, 2011.
European Examination Report re Application No. 08 755 267.5, dated Apr. 26, 2010.
European Examination Report re Application No. 08 755 267.5, dated Sep. 14, 2010.
Forster, "Intermolecular Energy Transfer and Fluorescence, Annaten der Physik" (1948) pp. 55-75.
Furnary A.P. et al. "Effect of hyperglycemia and continuous intravenous insulin infusions on outcomes of cardiac surgical procedures: The Portland Diabetic Project", Endocrine Practice, Mar./Apr. 2004, pp. 21-33, vol. 10.
Gamoh, et al., 222 Analytica Chimica Acta 201 (1989).
Gamsey, S. et al. 2007 "Boronic acid based bipyridinium salts as tunable receptors for monosaccharides and alpha-hydroxycarboxylates" J Am Chem Soc 129:1278-1286.
Gehrich, J. L., D. W. Lubbers, et al. (1986). "Optical fluorescence and its application to an intravascular blood gas monitoring system." IEE TBio-med Eng BME-33: 117-132.
Glazer, 59 Biochemistry 996 (1968).
Glazer, Chemical Abstracts, vol. 68, No. 111805q (1968).
Guilbault, George E., "Practical Fluorescence" (1973), pp. 599-600.
Hakkinen, Lajunen & Purokoski, A Potentiometric Study on the Complex Formation of Lactitol and Maltitol with Some Inorganic Oxyacids in Aqueous Solution, Chemical Abstracts, vol. 110, No. 83116f (1989).
Hakkinen, Purokoski & Lajunen, A Potentiometric Study on the Complex Formation of Germanic Acid and Germanate Ion with Sugar Acids and Disaccharides in Aqueous Solution, Chemical Abstracts, vol. 105, No. 233265s (1986).
Hayashi, et al., 149 Clinica Chimica Acta 149 (1985).
Hirata O. et al. 2002 "Allosteric saccharide sensing by a phenylboronic-acids-appended 5,15-bis(triarylethynyl)porphyrin" J Supramolecular Chemistry 2:133-142.
Hirsch Irl B. et al. "Acute Complications of Diabetes" Endocrinology and Metabolism Clinics of North America, Dec. 2000, pp. 745-771, vol. 29-4.
Hirshfeld, "Reabsorption Sensing in Fluorescence Spectroscopy," UCRL Abstract No. 89736 ABST, published by Pittsberg Conference on Scientific Instrumentation, Mar. 1984.
Kirk-Othmer, Encyclopedia of Chemical Technology, 3rd ed., vol. 8, John Wiley and Sons, New York, pp. 201-203 (1979).
Kostov, Y., P. Harms, et al. (2001). "Low-cost microbioreactor for high-throughput bioprocessing." Biotechnol Bioeng 72: 346-352.
Lakowitz et al., :"Optical sensing of glucose using phase-modulation fluorimtry," Analytica Chimica Acta, 271, (1993), 155-164.

Leijten FSS & DE Weerdt A W 1994 Critical illness polyneuropathy: a review of the literature, definition and pathophysiology. Clinical Neurology and Neurosurgery, 96: 10-19.

Lindner, et al., 473 J. Chromatography 227-240 (1989).

Lutty, G. A. (1978). "The acute intravenous toxicity of stains, dyes, and other fluorescent substances." Toxical Pharmacol. 44: 225-229.

Meadows and Schultz, "Design, manufacture and characterization of an optical fiber glucose affinity sensor based on an homogeneous fluorescence energy transfer assay system," (1993) Anal. Chim. Acta 280: pp. 21-30.

Medtronic, Features of the Guardian REAL-Time Continuous Glucose Monitoring System, Features that fit your diabetes management lifestyle, located at http://www.minimed.com/products/guardian/features.html on Aug. 28, 2007.

Mizock B A. Am J Med 1995; 98: 75-84.

Mosbach, Methods in Enzymology, vol. XLIV, 53 (1976).

Niu C.G. et al. "Fluorescence ratiometric pH sensor prepared from covalently immobilized porphyrin and benzothioxanthen e." 2005 Anal. Bioanal. Chem. 383(2):349-357.

Offenbacher, H., O. S. Wolfbeis, et al. (1986). "Fluorescence optical sensors for continuous determination of near-neutral pH values." Sensor Actuator 9: 73-84.

PCT Application No. PCT/US2008/063330.

PCT No. PCT/US2008/063332.

PCT International Preliminary Report and Written Opinion re PCT/US2009/040379 dated Oct. 19, 2010.

PCT International Preliminary Report on Patentabilitu re PCT/US2008/063330 dated Nov. 19, 2009.

PCT International Preliminary Report on Patentability and Written Opinion re PCT/US2008/053097 dated Aug. 11, 2009.

PCT International Preliminary Report on Patentability and Written Opinion re PCT/US2008/072359, dated Feb. 9, 2010.

PCT International Search Report (Declaration of Non-Establishment of ISR) and Written Opinion re PCT/US2009/040379 dated Aug. 4, 2009.

PCT International Search Report and Written Opinion in App. No. PCT/US2011/028222, dated May 6, 2011, in 30 pages.

PCT International Search Report and Written Opinion re App. No. PCT/US 10/61163, dated Mar. 9, 2011.

PCT International Search Report and Written Opinion re App. No. PCT/US10/61169, dated Mar. 1, 2011.

PCT International Search Report and Written Opinion re App. No. PCT/US10/61173, dated Feb. 28, 2011.

PCT International Search Report and Written Opinion re PCT App. No. PCT/US 10/50910, dated Dec. 3, 2010.

PCT International Search Report and Written Opinion re PCT/US2008/052204, dated May 27, 2008.

PCT International Search Report and Written Opinion re PCT/US2008/053226, dated Oct. 15, 2008.

PCT International Search Report and Written Opinion re PCT/US2008/063330 dated Sep. 3, 2008.

PCT International Search Report and Written Opinion re PCT/US2008/069855 dated Apr. 16, 2009.

PCT International Search Report and Written Opinion re PCT/US2008/072359 dated Dec. 15, 2008.

PCT International Search Report and Written Opinion re PCT/US2008/084239 dated Jan. 29, 2009.

PCT International Search Report and Written Opinion re PCT/US2010/037502, dated Aug. 6, 2010.

PCT International Search Report and Written Opinion re PCT/US2010/044761, dated Oct. 6, 2010.

PCT International Search Report and Written Opinion re PCT/US2011/034167, mailed Jul. 29, 2011.

PCT International Search Report re PCT/US2007/074255 dated Jul. 8, 2008 in 3 pages.

PCT International Search Report re PCT/US2008/053097 dated Jun. 27, 2008.

PCT Partial International Search Report re PCT/US2008/072359 dated Oct. 15, 2008.

PCT Partial Search Report re PCT/US2008/053226 dated Jun. 27, 2008.

PCT Preliminary Report re PCT/US2008/084239 dated May 25, 2010.

PCT Report on Patentability and Written Opinion re PCT/US2007/074255 dated Jan. 27, 2009 in 9 pages.

PCT Report on Patentability and Written Opinion re PCT/US2008/063332 dated Nov. 19, 2009.

PCT Search Report and Written Opinion re PCT/US2011/023939, dated Jul. 27, 2011.

Purokoski, Lajunen & Hakkinen, A Potentiometric Study on the Complex Formation of Arsenious Acid, Arsenite Ion, Telluric Acid and Tellurate Ion with Sugar Acids and Disaccharides in Aqueous Solution, Chemical Abstracts, vol. 107, No. 122178n (1987).

Roy, et al., J. Inorg. Nucl. Chem., 106 (1957).

Schulman, S. G., S. Chen, et al. (1995). "Dependence of the fluorescence of immobilized 1-hydroxypyrene-3,6,8-trisulfonate on solution pH: extension of the range of applicability of a pH fluorosensor." Anal Chim Acta 304: 165-170.

Seitz, "Chemical Sensors Based on Fiber Optics," Analytical Chemistry, vol. 56, pp. 16a-34a, 1984.

Sharrett, Z. et al. 2008 "Boronic acid-appended bis-viologens as a new family of viologen quenchers for glucose sensing" Tetrahedron Letters 49:300-304.

Snyder, et al., "The Preparation of Some Azo Boronic Acids," 70 J. Am. Chem. Soc. 232 (1948).

Song, A., S. Parus, et al. (1997) "High-performance fiber-optic pH microsensors for practical physiological measurements using a dual-emission sensitive dye." Analytical Chemistry 69: 863-867.

Streitwieser, Jr. & Heathcock, Introduction to Organic Chemistry (1976).

Sturdevant, M. F.: "How Sterilization Changes Long-Term Resin Properties", Plastics Engineering, Jan. 1991, pp. 27-32.

Suri, J. T. et al. 2003 "Continuous glucose sensing with a fluorescent thin-film hydrogel" Angew Chem Int Ed 42:5857-5859.

The Immunoassay Handbook, pp. 1-618, ed. David Wild, Macmillan Press, 1994, United Kingdom.

Turner N.G. et al. "Determination of the pH Gradient Across the Stratum Corneum." 1998 J. Investig. Dermatol. Symp. Proc. Aug. 3(2):110-3.

Udenfreund, "Fluorescence Assay in Biology and Medicine" (1962) pp. 108-109.

University of Santa Cruz, "Optical Glucose Sensor Holds Promise for Diabetics and Intensive Care Patients", Mar. 18, 2004, in 6 pages.

Van Den Berghe G., et al. "Intensive Insulin Therapy in the Medical ICU", The New England Journal of Medicine, Feb. 2, 2006, pp. 449-461, vol. 354-5.

Van Kempien & Kreuzer, "A Single-Unit Carbon Dioxide Sensing Microelectrode System," Respiration Physiology, (1975), 23, 371-379.

Vermeer, et al., 37 Tetr. Letters 3255 (1970).

Wilson, Intensive Insulin Therapy in Critical Care, Diabetes Care, Apr. 2007, pp. 1005-1011, vol. 30-4.

Zochodne D W et al. 1987 Polyneuropathy associated with critical illness: a complication of sepsis and multiple organ failure. Brain, 110: 819-842.

U. S. Reexamination, Request for Inter Partes Reexamination, dated Sep. 6, 2012.

Atherton, S. J. et al.: "Reactions of Three Bis(viologen) Tetraquaternary Salts and Their Reduced Radicals", J. Am. Chern. Soc. 1986, 108,3380-3385.

Ayala et al., Database Caplus, DN 133:189758. (Protein Science (2000), 9(8), 1589-1593).

Badugu, R., et al.: "A Glucose sensing contact lens: A new approace to non-invasive continuous physiological glucose monitoring", SPIE Proceedings, The International Society for Optical Engineering—SPIE, Bellingha, Washington, USA, vol. 5317, Jan. 25, 2004.

Baldini "Invasive Sensors in Medicine." Optical Chemical Sensors, NATO Science Series 11: Mathematics, Physics and Chemistry [online], 2006 [Retrieved on Nov. 15, 2010], vol. 224, pp. 417-435, Retrieved from the Internet: <URL http:www.springerlink.com>.

Ballerstadt, Ralph, et al.: "Fluorescence Resonance Energy Transfer-Based Near-Infrared Fluorescence Sensor for Glucose Monitoring", Diabetes Technology & Therapeutics, vol. 6, No. 2, Apr. 1, 2004.

Benmakroha et al. "Haemocompatibility of invasive sensors," Med. & Biol. Eng. & Comput., 1995, 33,811-821 (Nov. 1995).

Cao, H. et al.: "Fluorescent Chemosensors for Carbohydrates: A Decade's Worth of Bright Spies for Saccharides in Review", Journal of Fluorescence, vol. 14, No. 5, Sep. 2004.

Choleau et al.: "Calibration of a subcutaneous amperometric glucose sensor implanted for 7 days in diabetic patients, Part 2. Superiority of the one-point calibration method." Biosensors and Bioelectrics, vol. 17, No. 8, Aug. 1, 2002.

Cordes, D. B., et al., 2006, in Topics in Fluorescence Spectroscopy; vol. 11, Glucose Sensing, Springer "Two component optical sugar sensing using boronic acid-substituted viologens with anionic fluorescent dyes" pp. 47-87. (ISBN: 978-0-387-29571-8 p. 76, scheme 3.7).

DiCesare, N., et al.: "Saccharide Detection Based on the Amplified Fluorescence Quenching of a Water-Soluble Poly(phenylene ethynylene) by a Boronic Acid Functionalized Benzyl Viologen Derivativ~", LanQrnuir.2002,18, 7785-7787.

"Fiber Optic Oxygen Sensors: Theory of Operation", Fiber Optic Oxygen Sensors Theory of Operation, http://www.oceanoptics.com/Products/sensortheory.asp—4 pages.

Fidaleo et al., Database Caplus, DN 140:249134 (Chemical and Biochemical Engineering Quarterly (2003), 17(4), 311-318).

Gamsey, Soya et al.: "Continuous glulcose detection using boronic acid-substituted viologens in, fluorescent hydrogels: linker effects and extension to fiber optics" Langmuir, ACS, Washington, DC vol. 22, No. 21, Oct. 10, 2006, pp. 9067-9074 (XP002442273ISSN: 0743-7463, compound (1) schemata 1,2 figure 1).

Hunneche, "Antioxidant Activity of a Combinatorial Library of Emulsifier—Antioxidant Bioconjugates," J. Agric. Food Chem. 2008, 56, 9258-9268.

Hvastkovs, E. G., et al.: "Minor Groove Binding of a Novel Tetracationic Diviologen", Langmuir 2006, 22, 10821-10829.

Kuraganov, B. I., et al.: Criterion for Hill equation validity for description of biosensor calibration curves, Analytica Chimica Acta, vol. 427, No. 1, Jan. 1, 2001.

Kuwabara, T., et al.: "Effect of Alkali Metal Ions on Photochromic Behavior of Bisviologen-incorporated Oligo-oxyethylene Units", Rapid Communication. Photochemistry and Photobiology, 2003, 77(5); 572-575.

Lee S. K., et al.: "Conform~tion and binding properties of polymethylene-linked bisviologens-2-naphthol complexes", Journal of the Chemical Society, Perkin Transactions 2 2001, 1983-1988.

Liu, et al., "Characterization of Immobilization of an Enzyme in a Modified Y Zeolite Matrix and Its Application to an Amperometric Glucose Biosensor," Anal. Chem. 1997, 69, pp. 2343-2348.

Mignani et al. "Biomedical sensors using optical fibres." Reports on Progress in Physics [online], Jan. 1996 [Retrieved on Nov. 15, 2010], vol. 59, No. 1, pp. 1-28, Retrieved from the internet: <URL http://iopscience.iop.org>.

Mohr, G. J. et al.: Application of a Novel Lipophilized Fluorescent dye in an Opitcal Nitrate Sensor, Journal of Fluorescence 1995, 5, 135-138.

Park, Y. S., et al.: "Facile Reduction of ZeoliteOEncapsulated Viologens with Solvated Electrons and Selective Dispersion of Inter- and Intramolecular Dimers of Propylene-Bridged Bisviologen Radical Cation", LanQmuir 2000,16,4470-4477.

Peterson et al. "Fiber-optic for in vive measurement of oxygen partial pressure," Analytical Chemistry [online], Jan. 1984 [Retrieved on Nov. 15, 2010], vol. 57, No. 1, pp. 62-67, Retrieved from the Internet: <URL: http://pubs.acs.org>.

Piper, Hannah G. "Real-Time Continuous Glucose Monitoring in Pediatric Patients During and After Cardiac Surgery," in Pediatrics, vol. 118, No. 3, Sep. 2006.

Retrieved from the Internet <URL: http://www.invitrogen.com/site/us/en/home/References/Molecular-Probes-The-Handbook/Fluorophores -and-Their-Amine-Reactive-Derivatives/Fluorescein-Oregon-Green-and-Rhodamine-Green-Dyes.html#>, 11 pages.

Reyes-De-Corcuera, Josi et al.: "Enzyme-electropolymer-based amperometric biosensors: an innovative platform for time-temperature integrators." Journal of Agricultural and Food Chemistry, vol. 53, No. 23, Nov. 1, 2005.

Sato, H. et al.: "Polymer Effect in Electrochromic Behavior of Oligomeric Viologens", Journal of Applied Polymer Science, vol. 24, 2075-2085 (1979).

Stokes, et al.: "An optical oxygen sensor and reaction vessel for high-pressure applications", Limnol. Oceanogr., 44(1),1999,189-195.

Su et al., "Polyethersulfone Hollow Fiber Membranes for Hemodialysis," Progress in Hemodialysis—From Emergent Biotechnology to Clinical Practice, www.intechopen.com, Nov. 7, 2011. ISBN 978-953-307-377-4.

Suri, J. T. et al.: "Monosaccharide Detection with 4,7-Phenanthrolinium Salts: Charge-Induced Fuorescence Sensig", Langmuir 2003,19,5145-5152.

Takashima, H., et al.: "Rema~l<ably stereoselective photoinduced electron-transfer reaction between zinc myoglobin and optically active binaphthyl bisviologen", Journal 0 Biological Inorganic Chemistry 2003, 8, 499-506.

Tsukahara, K., et al.: "Syntheses, Characterizations, and Redox Behavior of Optically Active Viologens and Bisviologens", Bulletin of the Chemical Society of Japan 1999, 72,139-149.

Volker, Ludwig et al.: "Continuous Glucose Monitoring with Glucose Sensors: Calibration and Assessment Criteria", Diabetes Technology & Therapeutics, vol. 5, No. 4, Aug. 1, 2003.

Wang, D. et al. 2001 "Ph( )toh Jminescence quenching of conjugated macromolecules by bipyridinium derivatives in aqueous media: charge dependence" Langmuir 17:1262-1266.

Wolfbeis, O. S., E. Fuerlinger, et al. (1983). "Fluorimetric analysis. I. Study on fluorescent indicators for measuring near neutral ('physiological') pH values." Fresneius' Z. Anal. Chem. 314 (2): 119-124.

Xu, Z., A. Rollins, et al. (1998) "A novel fiber-optic pH sensor incorporating carboxy SNAFL-2 and fluorescent wavelength-ratiometric detection" Journal of Biomedical Materials Research 39:9-15.

Zhang, S., S. Tanaka, et al. (1995). "Fibre-optical sensor based on fluorescent indicator for monitoring physiological pH values." Med Biol Eng Comput 33: 152-156.

Zhujun, Z. and W. R. Seitz (1984). "A fluorescence sensor for quantifying pH in the range from 6.5 to 8.5." Analytical Chimica Acta 160:47-55.

Zhujun, Z., et al. (1984). Analytical Chimica Acta 160:305-309.

Zisser, MD, et al. "Excitation: The use of Fluorescence in Glucose Monitoring (Part 11)," Glumetrics, Feb. 13, 2010.

* cited by examiner

* Dimension Clinical Chemistry System, model RxL, Dade Behring, Inc., Deerfield, Ill.
Lacara, T. et al. "Comparison of Point-of-care and laboratory glucose analysis in critically ill patients" Am J. Crit Care, 16, 336-347, 2007)

USE OF AN EQUILIBRIUM INTRAVASCULAR SENSOR TO ACHIEVE TIGHT GLYCEMIC CONTROL

CROSS-REFERENCE TO RELATED APPLICATIONS

This application is a continuation of U.S. patent application Ser. No. 12/274,617, filed Nov. 20, 2008 and entitled "Use of an Equilibrium Intravascular Sensor to Achieve Tight Glycemic Control," which claims the benefit of U.S. Provisional Patent Application No. 60/989,732, filed Nov. 21, 2007. U.S. patent application Ser. No. 12/274,617 is related to U.S. patent application Ser. No. 11/671,880, filed Feb. 6, 2007. All of the above referenced applications are incorporated by reference herein in their entirety.

BACKGROUND OF THE INVENTION

1. Field of the Invention

Embodiments of the present invention relate to analyte sensors. In particular, certain embodiments of the present invention relate to methods of using non-consuming intravascular glucose sensors to achieve tight glycemic control.

2. Description of the Related Art

A specific type of polyneuropathy develops in patients that are treated within an intensive care unit (hereinafter also designated ICU) for several days to weeks and this for a variety of primary injuries or illnesses. This polyneuropathy, known as "Critical Illness Polyneuropathy" (hereinafter also designated CIPNP) occurs in about 70% of patients who have the systemic inflammatory response syndrome (SIRS) (Zochodne D W et al. 1987 Polyneuropathy associated with critical illness: a complication of sepsis and multiple organ failure. Brain, 110: 819-842); (Leijten F S S & De Weerdt A W 1994 Critical illness polyneuropathy: a review of the literature, definition and pathophysiology. Clinical Neurology and Neurosurgery, 96: 10-19). However, clinical signs are often absent and it remains an occult problem in many ICUs worldwide. Nonetheless, it is an important clinical entity as it (is) a frequent cause of difficulty to wean patients from the ventilator and it leads to problems with rehabilitation after the acute illness has been treated and cured.

When CIPNP is severe enough, it causes limb weakness and reduced tendon reflexes. Sensory impairment follows but is difficult to test in ICU patients. Electro-physiological examination (EMG) is necessary to establish the diagnosis (Bolton C F. 1999 Acute Weakness. In: Oxford Textbook of Critical Care; Eds. Webb A R, Shapiro M J, Singer M, Suter P M; Oxford Medical Publications, Oxford UK; pp. 490-495). This examination will reveal a primary axonal degeneration of first motor and then sensory fibers. Phrenic nerves are often involved. Acute and chronic denervation has been confirmed in muscle biopsies of this condition. If the underlying condition (sepsis or SIRS) can be successfully treated, recovery from and/or prevention of the CIPNP can be expected. This will occur in a matter of weeks in mild cases and in months in more severe cases. In other words, the presence of CIPNP can delay the weaning and rehabilitation for weeks or months.

The pathophysiology of this type of neuropathy remains unknown (Bolton C F 1996 Sepsis and the systemic inflammatory response syndrome: neuromuscular manifestations. Crit Care Med. 24: 1408-1416). It has been speculated to be directly related to sepsis and its mediators. Indeed, cytokines released in sepsis have histamine-like properties which may increase microvascular permeability. The resulting endoneural edema could induce hypoxia, resulting in severe energy deficits and hereby primary axonal degeneration. Alternatively, it has been suggested that cytokines may have a direct cytotoxic effect on the neurons. Contributing factors to disturbed microcirculation are the use of neuromuscular blocking agents and steroids. Moreover, a role for aminoglucosides in inducing toxicity and CIPNP has been suggested. However, there is still no statistical proof for any of these mechanisms in being a true causal factor in the pathogenesis of CIPNP.

Although polyneuropathy of critical illness was first described in 1985 by three different investigators, one Canadian, one American, and one French, to date there is no effective treatment to prevent or stop Critical Illness Polyneuropathy.

To date the current standard of practice of care, especially of critically ill patients, was that within the settings of good clinical ICU practice, blood glucose levels are allowed to increase as high as to 250 mg/dL or there above. The reason for this permissive attitude is the thought that high levels of blood glucose are part of the adaptive stress responses, and thus do not require treatment unless extremely elevated (Mizock B A. Am J Med 1995; 98: 75-84). Also, relative hypoglycemia during stress is thought to be potentially deleterious for the immune system and for healing (Mizock B A. Am J Med 1995; 98: 75-84).

Van Den Berghe, U.S. Patent Publication No. 2002/0107178 A1, disclosed that critical illness in a patient and/or CIPNP can be prevented, treated or cured, at least to a certain extent, by strictly controlling glucose metabolism during said critical illness by applying intensive treatment with a blood glucose regulator, for example, insulin treatment, with clamping of blood glucose levels within a range where the lower limit can be selected to be about 60, about 70 or about 80 mg/dL and the upper limit can be selected to be about 110, about 120 or about 130 mg/dL, more specifically to the normal range (i.e., from about 80 to about 110 mg/dL). The skilled art worker, for example, the physician, will be able to decide exactly which upper and lower limits to use. Alternatively, the range is from about 60 to about 130, preferably, from about 70 to about 120, more preferred, from about 80 to about 110 mg/dL.

Unfortunately, despite the benefits of tight glycemic control in the ICU patient, it has been difficult to implement in part because there are no accurate, real-time, indwelling glucose sensors available. Consequently, it has been a significant burden on the patients and the ICU staff to perform frequent blood sampling for conventional ex vivo blood glucose monitoring.

There has been an on-going effort over many years to use equilibrium chemistry to measure polyhydroxyl compound (e.g., glucose) concentration in bodily fluids. For example, several attempts have been made to detect glucose by fluorescence using dyes associated with boronic acid groups. Boronate moieties bind glucose reversibly. When boronic acid functionalized fluorescent dyes bind glucose, the properties of the dye are affected, such that a signal related to the concentration of glucose may be generated and detected.

Russell (U.S. Pat. Nos. 5,137,833 and 5,512,246) used a boronic acid functionalized dye that bound glucose and generated a signal related to the glucose concentration. James et al. (U.S. Pat. No. 5,503,770) employed a similar principle, but combined a fluorescent dye, an amine quenching functionality, and boronic acid in a single complex. The fluorescence emission from the complex varied with the amount of glucose binding. Van Antwerp et al. (U.S. Pat. Nos. 6,002,954 and 6,011,984) combined features of the previously cited references and also disclosed a device purported to be implantable. A. E. Colvin, Jr. (U.S. Pat. No. 6,304,766) also disclosed optical-based sensing devices for in situ sensing in humans that utilize boronate-functionalized dyes. But despite the effort, no practical intravascular system has been developed and commercialized for in vivo monitoring.

Certain measurable parameters using blood or bodily fluid, such as pH and concentrations of $O_2$, $CO_2$, $Na^+$, $K^+$, and polyhydroxyl compounds, like glucose, have been determined in vivo. The ability to do these measurements in vivo is important because it is necessary to make frequent determinations of such analytes when monitoring a patient. In many instances, a sensor will be analyte specific and therefore a plurality of sensors may be needed to measure several analytes, which can cause attendant discomfort to the patient and add complexity to the electronic monitoring equipment.

In an effort to solve the design problems posed by the limitation in physical dimension for in vivo monitoring, others have incorporated different dyes into one device to get simultaneous readings of two parameters. For example, Alder et al. (U.S. Pat. No. 5,922,612) disclosed a method for optical determination of pH and ionic strength of an aqueous sample using two different dyes on one sensor. Gray et al. (U.S. Pat. No. 5,176,882) taught the use of a fiber optic device incorporating a hydrophilic polymer with immobilized pH sensitive dye and potassium or calcium sensitive fluorescent dyes to measure the analyte concentration in conjunction with pH. In U.S. Pat. No. 4,785,814, Kane also disclosed the use of two dyes embedded in a composite membrane for the simultaneous measurements of pH and oxygen content in blood. However, incorporation of multiple dyes into a single sensor complicates the manufacture of such sensors.

Besides the foregoing problems associated with separate indwelling sensors for each analyte being monitored, particularly in the intensive care setting, and multiple dye sensors, another problem associated with many dye-based analyte sensors is pH sensitivity. A slight change in pH may modify or attenuate indicator emissions, and cause inaccurate readings. This problem is particularly acute for monitoring blood glucose levels in diabetic and non-diabetic ICU patients, whose blood pH may fluctuate rapidly. Since accurate blood glucose level measurements are essential for treating these patients, there is a significant need for a glucose sensor that facilitates real-time correction of the pH effect without requiring separate indwelling pH and analyte sensors, or sensors having multiple dyes. Accordingly, in order for acutely ill patients in the ICU setting to enjoy the benefit of tight glycemic control, there remains an important unmet need for a glucose sensor configured for intravascular deployment, wherein the sensor employs a non-consuming, equilibrium chemistry that provides accurate, real-time glucose levels which simultaneously monitors and corrects for fluctuations in blood pH.

SUMMARY OF THE INVENTION

A method for achieving tight glycemic control in a patient in need thereof is disclosed. The method comprises deploying an equilibrium glucose sensor within a blood vessel in the patient, coupling the sensor to a monitor that displays the blood glucose concentration, and administering a blood glucose regulator when the blood glucose concentration varies outside of the predetermined concentration range. The blood glucose regulator is administered in an amount sufficient to return the blood glucose concentration to within the predetermined concentration range, thereby achieving tight glycemic control.

In some embodiments, an alarm signal is generated when the blood glucose concentration varies outside of the predetermined concentration range. In other embodiments, the monitor displays the rate and direction of change in the blood glucose concentration. In still other embodiments, the blood glucose concentration has a rising or falling trend and the blood glucose regulator is administered in an amount sufficient to reverse the rising or falling trend. An alarm signal may be generated when the rate and direction of change in the blood glucose concentration varies outside a predetermined range.

The predetermined concentration range may be from about 60 to about 180 mg/dl glucose, about 60 to about 130 mg/dl glucose, or about 80 to about 110 mg/dl. In some embodiments, the blood glucose regulator is insulin or an analog or derivative thereof. The blood glucose regulator may be glucose.

In some embodiments, the equilibrium glucose sensor comprises a fluorophore and an analyte binding moiety. The fluorophore may be chosen from a group consisting of a fluorescent organic dye, an organometallic compound, a metal chelate, a fluorescent conjugated polymer, quantum dots or nanoparticles, and combinations of the above.

In some embodiments, the fluorescent dye is capable of being excited by light of a wavelength greater than about 400 nm. The fluorescent dye may be stable against photo-oxidation, hydrolysis, and biodegradation. The fluorescent dye may comprise a HPTS-triCysMA dye, SNARF-1, SNAFL-1, or TSPP.

In some embodiments, the analyte binding moiety comprises a boronic acid functionalized viologen quencher. The boronic acid functionalized viologen quencher may comprise a 3,3'-oBBV quencher.

In some embodiments, the fluorescent dye and the analyte binding moiety are physically immobilized within a semi-permeable membrane. The fluorescent dye and the analyte binding moiety may be sufficiently greater in size than the glucose, where the semi-permeable membrane allows passage of glucose but blocks passage of the fluorescent dye and the analyte binding moiety. In other embodiments, the fluorescent dye and the analyte binding moiety are physically immobilized within a hydrogel matrix. The fluorescent dye and the analyte binding moiety may be covalently bonded to a hydrogel matrix. The fluorescent dye and the analyte binding moiety may be covalently bonded to each other.

In some embodiments, the concentration of glucose and a second analyte are simultaneously measured. The second analyte may be a hydrogen ion.

In some embodiments, the equilibrium glucose sensor comprises an optical fiber. The optical fiber may be coupled to a light source. The optical fiber may be coupled to an emission light detector.

Another method for achieving tight glycemic control in a patient in need thereof, is disclosed. The method comprises deploying an equilibrium glucose sensor within a blood vessel in the patient. The equilibrium glucose sensor comprises a fluorescent dye operably coupled to a boronic acid functionalized quencher. The sensor is coupled to a monitor that displays the blood glucose concentration and the rate and direction of change in the blood glucose concentration. A blood glucose regulator is administered when the blood glucose concentration varies outside of a predetermined concentration range. The blood glucose regulator is administered in an amount sufficient to return the blood glucose concentration to within the predetermined concentration range or reverse a rising or falling trend in the blood glucose concentration, thereby achieving tight glycemic control. In some embodiments, the quencher is a viologen.

DETAILED DESCRIPTION OF THE PREFERRED EMBODIMENT

Figure 1:
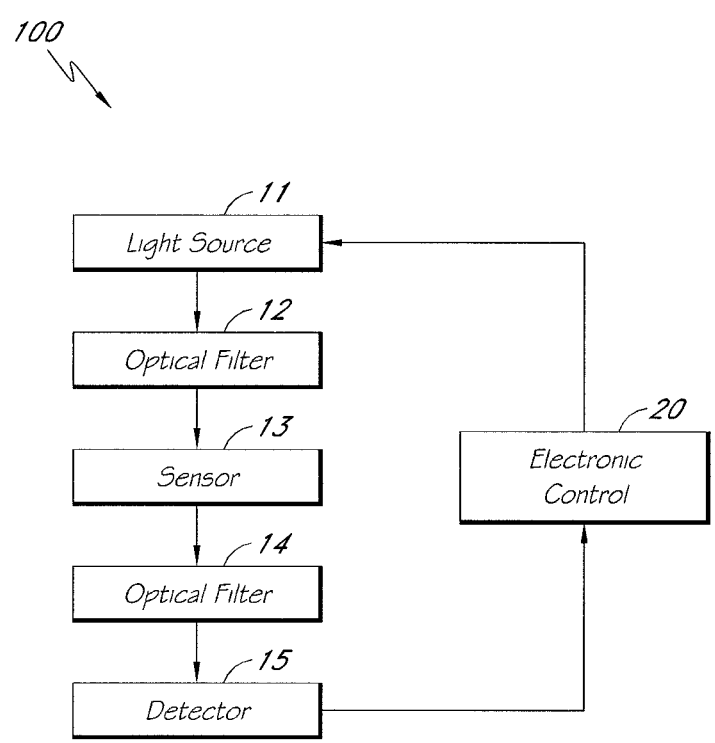
FIG. 1 is a flow chart showing the sensing mechanism of one embodiment of the present invention.

In a preferred embodiment, the present invention is directed to an optical sensor capable of measuring two analytes with a single indicator system. A preferred sensor employs equilibrium chemistry in which a glucose signal is produced in response to an equilibrium process, such as for example the association and disassociation of a quencher and fluorophore. In certain embodiments, a single fluorophore (e.g., a fluorescent dye) is used to: (1) determine the concentration of a first analyte, e.g., $H^+$ (pH), by a ratiometric method, wherein such determination is independent of the concentration of the fluorophore; and (2) determine the concentration of a second analyte, e.g., a polyhydroxyl compounds (e.g., preferably glucose) by measuring the apparent fluorophore concentration (e.g., emission intensity of the fluorophore upon excitation), wherein the apparent fluorophore concentration is dependent on the concentration of the second analyte. Further, where measurement of the second analyte concentration is dependent on the first analyte concentration (e.g., in optical systems in which glucose measurement varies with pH—a common problem in this field), then in accordance with one embodiment of the present invention, the measured second analyte concentration may be corrected for the contribution of the first analyte concentration. The sensor is preferably stable in aqueous media (e.g., physiological media, blood, interstitial fluid, etc.), and more preferably, the sensor is configured to be inserted into a blood vessel where it can remain indwelling for a period of time. Thus, in accordance with a preferred embodiment of the present invention, an optical sensor configured for intravascular placement is disclosed, which sensor is capable of measuring two analytes (preferably pH and glucose) with a single indicator system and correcting the glucose measurement for any contributions of pH.

Although preferred embodiments of the sensor are directed inter alia to ratiometric pH sensing, other first analyte concentrations may be determined in accordance with the broader scope of the present invention, as long as the indicator system comprises an indicator that exists in at least two forms, the concentration of which is associated with the concentration of the first analyte and the emission ratio of which is independent of the indicator concentration. Likewise, although glucose is used as a second analyte example herein, it is understood that the concentration of other polyhydroxyl-containing organic compounds (carbohydrates, 1,2-diols, 1,3-diols and the like) in a solution may be determined using embodiments of this invention, as long as the indicator system comprises an indicator that is operably coupled to a binding moiety that binds the second analyte, wherein the signal intensity of the indicator varies with the concentration of second analyte. In some embodiments, the second analyte may include non-carbohydrates.

Indicator System

An indicator reports on what is happening in the medium being investigated. An indicator system is a specific type of sensing system comprising an indicator, An example of a mobile indicator system would be a probe, while an immobilized indicator system may be a sensor. The indicator systems used in accordance with certain embodiments of the present invention comprise a fluorophore operably coupled to an analyte binding moiety, where analyte binding causes an apparent optical change in the fluorophore concentration (e.g., emission intensity). It is further desired that the fluorophore has different acid and base forms that exhibit a detectable difference in spectral properties such that ratiometric pH sensing is enabled. For example, a glucose binding moiety such as 3,3'-oBBV (described in detail below) that is operably coupled to a fluorescent dye such as HPTS-triLysMA (described in detail below) will quench the emission intensity of the fluorescent dye, wherein the extent of quenching is reduced upon glucose binding resulting in an increase in emission intensity related to glucose concentration. In preferred embodiments, the indicator systems comprise a dye having at least two anionic groups and a quencher having at least two boronic acids. In further preferred embodiments, the indicator systems also comprise a means for immobilizing the sensing moieties (e.g., dye-quencher) such that they remain physically close enough to one another to interact (quenching). As in vivo sensing is desired, such immobilizing means is preferably insoluble in an aqueous environment (e.g., intravascular), permeable to the target analytes, and impermeable to the sensing moieties. Typically, the immobilizing means comprises a water-insoluble organic polymer matrix. For example, the HPTS-triLysMA dye and 3,3'-oBBV quencher may be effectively immobilized within a DMAA (N,N-dimethylacrylamide) hydrogel matrix (described in detail below), which allows pH and glucose sensing in vivo.

Some embodiments of fluorophores, analyte binding moieties and immobilizing means are set forth in greater detail below. A person skilled in the art would understand that while indicator systems comprising fluorophores and boronic acid-appended quenchers, are described in greater detail below, other indicator systems based on the principle of equilibrium chemistry used intravascularly to achieve tight glycemic control are within the scope of the present invention.

Fluorophores

"Fluorophore" refers to a substance that when illuminated by light at a particular wavelength emits light at a longer wavelength; i.e. it fluoresces. Fluorophores include but are not limited to fluorescent organic dyes, organometallic compounds, metal chelates, fluorescent conjugated polymers, quantum dots or nanoparticles and combinations of the above. In some instances, fluorescent organic dyes are simply called fluorescent dyes. Fluorophores may be discrete moieties or substituents attached to a polymer.

Fluorophores that may be used in certain embodiments are capable of being excited by light of wavelength at or greater than about 400 nm, with a Stokes shift large enough that the excitation and emission wavelengths are separable by at least 10 nm. In some embodiments, the separation between the excitation and emission wavelengths may be equal to or greater than about 30 nm. These fluorophores are preferably susceptible to quenching by electron acceptor molecules, such as viologens, and are resistant to photo-bleaching. They are also preferably stable against photo-oxidation, hydrolysis and biodegradation.

In some embodiments, the fluorophore is a discrete compound.

In some embodiments, the fluorophore is a pendant group or a chain unit in a water-soluble or water-dispersible polymer having molecular weight of about 10,000 daltons or greater, forming a dye-polymer unit. In one embodiment, such dye-polymer unit is non-covalently associated with a water-insoluble polymer matrix $M^1$ and is physically immobilized within the polymer matrix $M^1$, wherein $M^1$ is permeable to or in contact with analyte solution. In another embodiment, the dye in the dye-polymer unit is negatively charged, and the dye-polymer unit may be immobilized as a complex with a cationic water-soluble polymer, wherein said complex is permeable to or in contact with the analyte solution. In one embodiment, the dye is one of the polymeric derivatives of hydroxypyrene trisulfonic acid. The polymeric dyes may be water-soluble, water-swellable or dispersible in water. In some embodiments, the polymeric dyes may also be cross-linked. In preferred embodiments, the dye has a negative charge.

In other embodiments, the dye molecule is covalently bonded to the water-insoluble polymer matrix $M^1$, wherein said $M^1$ is permeable to or in contact with the analyte solution. The dye molecule is bonded to $M^1$ forming a structure $M^1$-$L^1$-Dye. $L^1$ is a hydrolytically stable covalent linker that covalently connects the sensing moiety to the polymer or matrix. Examples of $L^1$ include lower alkylene (e.g., $C_1$-$C_8$ alkylene), optionally terminated with or interrupted by one or more divalent connecting groups selected from sulfonamide (—$SO_2NH$—), amide —(C=O)N—, ester —(C=O)—O—, ether. —O—, sulfide —S—, sulfone (—$SO_2$—), phenylene —$C_6H_4$—, urethane —NH(C=O)—O—, urea —NH(C=O)NH—, thiourea —NH(C=S)—NH—, amide —(C=O)NH—, amine —NR— (where R is defined as alkyl having 1 to 6 carbon atoms) and the like, or a combination thereof. In one embodiment, the dye is bonded to a polymer matrix through sulfonamide functional groups.

In some embodiments, useful dyes include pyranine derivatives (e.g. hydroxypyrene trisulfonamide derivatives and the like), which have the following formula:

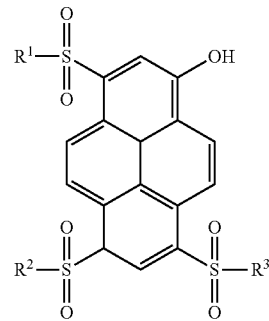

wherein $R^1$, $R^2$, $R^3$ are each —$NHR^4$, $R^4$ is —$CH_2CH_2$(—$OCH_2CH_2$—)$_n X^1$; wherein $X^1$ is —OH, —$OCH_3COOH$, —$CONH_2$, —$SO_3H$, —$NH_2$, or OMe; and n is between about 70 and 10,000.

In another embodiment, the fluorescent dye is 8-hydroxypyrene-1,3,6-N,N',N"-tris-(methoxypolyethoxyethyl (n~125)sulfonamide) (HPTS-PEG):

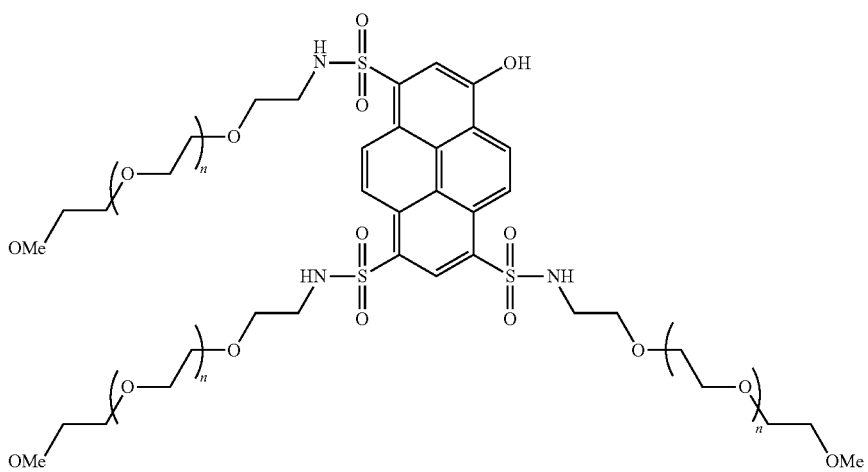

It is noted that dyes such as HPTS-PEG (above) having no anionic groups other than the partially ionized —OH group, may not provide a very strong glucose response when operably coupled to a viologen quencher, particularly a viologen quencher having only a single boronic acid moiety.

In some embodiments, the fluorescent dye is 8-hydroxypyrene-1,3,6-trisulfonate (HPTS). The counterions can be $H^+$ or any other cation with the proviso that the dye remains compatible with aqueous media including physiological fluids. HPTS exhibits two excitation wavelengths at around 450 nm and around 405 nm, which correspond to the absorption wavelengths of the acid and its conjugate base. The shift in excitation wavelength is due to the pH-dependent ionization of the hydroxyl group on HPTS. As the pH increases, HPTS shows an increase in absorbance at about 450 nm, and a decrease in absorbance below about 420 nm. The pH-dependent shift in the absorption maximum enables dual-excitation ratiometric detection in the physiological range. This dye has a molecular weight of less than 500 daltons, so it will not stay within the polymer matrix, but it can be used with an anion exclusion membrane.

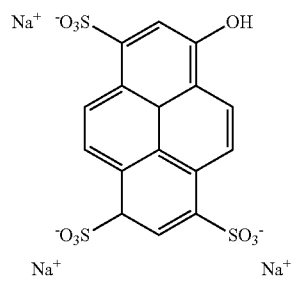

(the $Na^+$ salt of HPTS—"pyranine")

In another embodiment, the fluorescent dye is a polymer of 8-acetoxy-pyrene-1,3,6-N,N',N"-tris-(methacrylpropylamidosulfonamide) (acetoxy-HPTS-MA), subsequently hydrolyzed to remove the acetoxy protecting group:

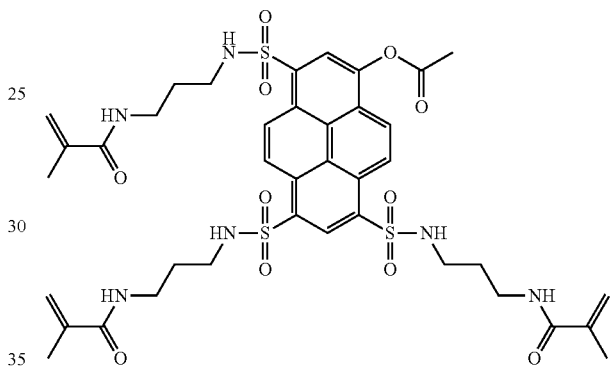

It is noted that dyes such as HPTS-MA and polymers comprising said dyes having no anionic groups other than the partially ionized —OH group, may not give very strong glucose response when operably coupled to a viologen quencher, particularly a viologen quencher having only a single boronic acid moiety.

In another embodiment, the fluorescent dye is 8-hydroxypyrene-1,3,6-N,N',N"-tris-(carboxypropylsulfonamide) ($HPTS-CO_2$):

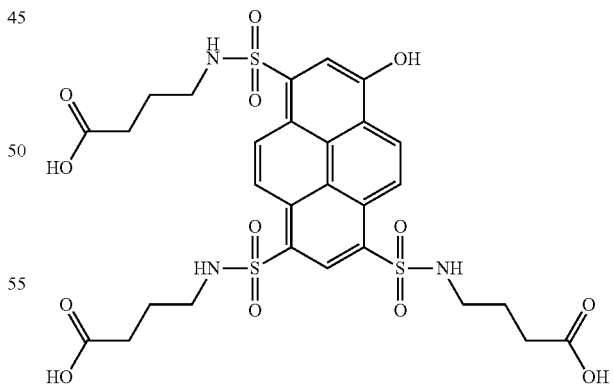

Representative dyes as discrete compounds are the tris adducts formed by reacting 8-acetoxypyrene-1,3,6-trisulfonylchloride (HPTS-Cl) with an amino acid, such as amino butyric acid, followed by hydrolysis to remove the acetoxy group. In one embodiment, the dyes may be bonded to a polymer through the sulfonamide functional groups. In other embodiments, the dye may be one of the polymeric derivatives of hydroxypyrene trisulfonic acid. Hydroxypyrene trisulfonamide dyes bonded to a polymer and bearing one or more anionic groups are most preferred, such as copolymers of 8-hydroxypyrene-1-N-(methacrylamidopropylsulfonamido)-N',N''-3,6-bis(carboxypropylsulfonamide) HPTS-CO$_2$-MA with HEMA, PEGMA, and the like.

In another embodiment, the fluorescent dye is HPTS-TriCys-MA:

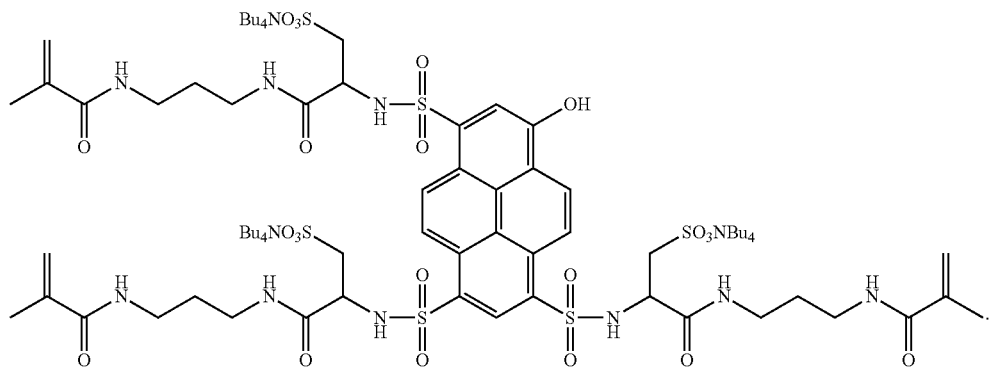

This dye may be used with a quencher comprising boronic acids, such as 3,3'-oBBV. While dyes substituted with polymerizable groups or other reactive groups may be used directly in some embodiments, preferably, the dyes are coupled to a polymer or matrix. In a preferred embodiment, polymers comprising HPTS-TriCys-MA are used in the sensing systems of this invention.

Of course, in some embodiments, substitutions other than Cys-MA on the HPTS core are consistent with aspects of the present invention, as long as the substitutions are negatively charged and include a reactive group, preferably a polymerizable group. Either L or D stereoisomers of cysteine may be used. In some embodiments, only one or two of the sulfonic acids may be substituted. Likewise, in variations to HPTS-CysMA shown above, other counterions besides NBu$_4^+$ may be used, including positively charged metals, e.g., Na$^+$. In other variations, the sulfonic acid groups may be replaced with other acidic ionizable functional groups e.g., phosphoric, carboxylic, etc.

Another suitable dye is HPTS-LysMA. Although this dye can be used in its monomeric form, polymers comprising this dye are preferred. The structure of HPTS-LysMA is pictured below:

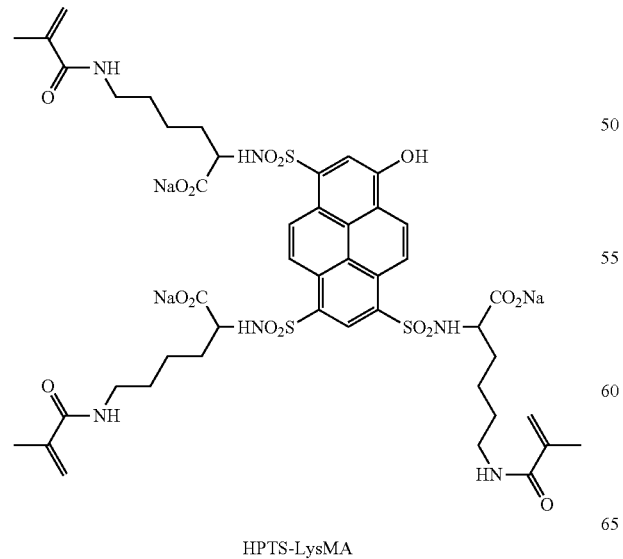

HPTS-LysMA

Other examples include soluble copolymers of 8-acetoxypyrene-1,3,6-N,N',N''-tris(methacrylamidopropylsulfonamide) with HEMA, PEGMA, or other hydrophilic comonomers. The phenolic substituent in the dye is protected during polymerization by a blocking group that can be removed by hydrolysis after completion of polymerization. Such suitable blocking groups, as for example, acetoxy, trifluoroacetoxy, and the like, are well known in the art.

Fluorescent dyes, including HPTS and its derivatives are known and many have been used in analyte detection. See e.g., U.S. Pat. Nos. 6,653,141, 6,627,177, 5,512,246, 5,137,833, 6,800,451, 6,794,195, 6,804,544, 6,002,954, 6,319,540, 6,766,183, 5,503,770, and 5,763,238; and co-pending U.S. patent application Ser. Nos. 11/296,898; 11/782,553; and 60/954,204; each of which is incorporated herein in its entirety by reference thereto.

The SNARF and SNAFL dyes from Molecular Probes may also be useful fluorophores in accordance with aspects of the present invention. The structures of SNARF-1 and SNAFL-1 are shown below.

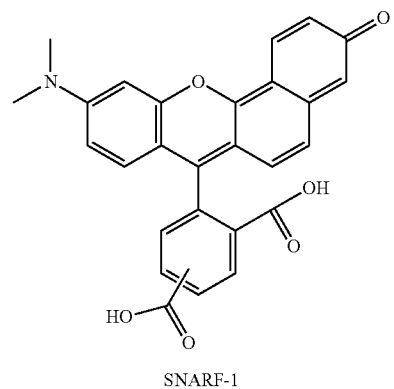

SNARF-1

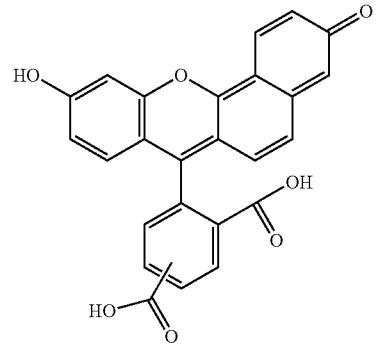

SNAFL-1

Additionally, a set of isomeric water-soluble fluorescent probes based on both the N-boronobenzyl derivatives of 6-methyl- and 6-methoxyquinoline, which show spectral shifts and intensity changes with pH in a wavelength-ratiometric and colorimetric manner, may be useful in accordance with some embodiments of the present invention (See e.g., Badugu, R. et al. 2005 Talanta 65 (3):762-768; and Badugu, R. et al. 2005 Bioorg. Med. Chem. 13 (1):113-119); incorporated herein in its entirety by reference.

Another example of a fluorescence dye that may be pH and saccharide sensitive is tetrakis(4-sulfophenyl)porphine (TSPP)—shown below. TSPP may not work optimally in blood, where the porphyrin ring may react with certain metal ions, like ferric, causing a change in optical properties.

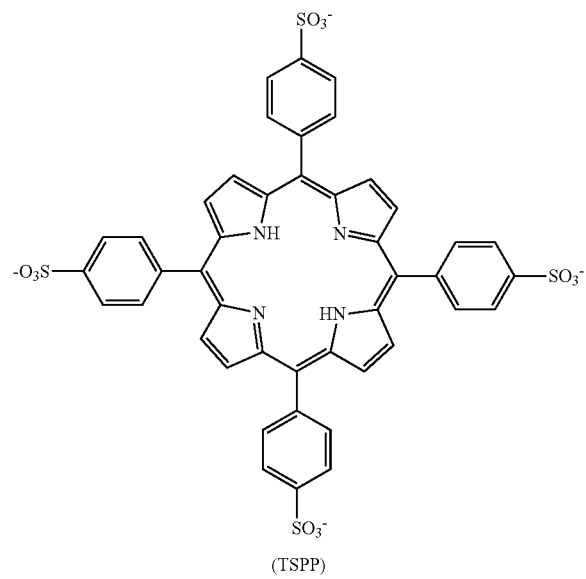

(TSPP)

Additional examples of pH sensitive fluorescent indicators that may be useful for simultaneous determination of pH and glucose in the sensor of the present invention are described in US 2005/0233465 and US 2005/0090014; each of which is incorporated herein by reference in its entirety.

Analyte Binding Moieties—Quenchers

In accordance with broad aspects of the present invention, the analyte binding moiety provides the at least dual functionality of being able to bind an analyte and being able to measure the concentration of the fluorophore (e.g., as a change in emission signal intensity) in a manner related to the amount of analyte binding. In certain embodiments, the analyte binding moiety is associated with a quencher. "Quencher" refers to a compound that reduces the emission of a dye when in its presence. Quencher (Q) is selected from a discrete compound, a reactive intermediate which is convertible to a second discrete compound or to a polymerizable compound or Q is a pendant group or chain unit in a polymer prepared from said reactive intermediate or polymerizable compound, which polymer is water-soluble or dispersible or is an insoluble polymer, said polymer is optionally cross-linked.

In one example, the moiety that provides glucose recognition in the embodiments is an aromatic boronic acid. The boronic acid is covalently bonded to a conjugated nitrogen-containing heterocyclic aromatic bis-onium structure (e.g., a viologen). "Viologen" refers generally to compounds having the basic structure of a nitrogen containing conjugated N-substituted heterocyclic aromatic bis-onium salt, such as 2,2'-, 3,3'- or 4,4'-N,N'bis-(benzyl) bipyridium dihalide (i.e., dichloride, bromide chloride), etc. Viologen also includes the substituted phenanthroline compounds. The boronic acid substituted quencher preferably has a pKa of between about 4 and 9, and reacts reversibly with glucose in aqueous media at a pH from about 6.8 to 7.8 to form boronate esters. The extent of reaction is related to glucose concentration in the medium. Formation of a boronate ester diminishes quenching of the dye, (e.g., a fluorophore) by the viologen resulting in an increase in signal emission (e.g., fluorescence) dependent on glucose concentration. A useful bis-onium salt is compatible with the analyte solution and capable of producing a detectable change in the signal emission of the dye in the presence of the analyte to be detected.

Bis-onium salts in the embodiments of this invention are prepared from conjugated heterocyclic aromatic di-nitrogen compounds. The conjugated heterocyclic aromatic di-nitrogen compounds are selected from dipyridyls, dipyridyl ethylenes, dipyridyl phenylenes, phenanthrolines, and diazafluorenes, wherein the nitrogen atoms are in a different aromatic ring and are able to form an onium salt. It is understood that all isomers of said conjugated heterocyclic aromatic di-nitrogen compounds in which both nitrogens can be substituted are useful in this invention. In one embodiment, the quencher may be one of the bis-onium salts derived from 3,3'-dipyridyl, 4,4'-dipyridyl and 4,7-phenanthroline.

In some embodiments, the viologen-boronic acid adduct is a discrete compound having a molecular weight of about 400 daltons or greater. In other embodiments, it is a pendant group or a chain unit of a water-soluble or water-dispersible polymer with a molecular weight greater than about 10,000 daltons. In one embodiment, the quencher-polymer unit is non-covalently associated with a polymer matrix and is physically immobilized therein. In yet another embodiment, the quencher-polymer unit is immobilized as a complex with a negatively charge water-soluble polymer.

In other embodiments, the viologen-boronic acid moiety is a pendant group or a chain unit in a cross-linked, hydrophilic polymer or hydrogel sufficiently permeable to the analyte (e.g., glucose) to allow equilibrium to be established.

In other embodiments, the quencher is covalently bonded to a second water-insoluble polymer matrix $M^2$, which can be represented by the structure $M^2$-$L^2$-Q. $L^2$ is a linker selected from the group consisting of a lower alkylene (e.g., $C_1$-$C_8$ alkylene), sulfonamide, amide, quaternary ammonium, pyridinium, ester, ether, sulfide, sulfone, phenylene, urea, thiourea, urethane, amine, and a combination thereof. The quencher may be linked to $M^2$ at one or two sites in some embodiments.

For the polymeric quencher precursors, multiple options are available for attaching the boronic acid moiety and a reactive group which may be a polymerizable group or a coupling group to two different nitrogens in the heteroaromatic centrally located group. These are:

a) a reactive group on a first aromatic moiety is attached to one nitrogen and a second aromatic group containing at least one —$B(OH)_2$ group is attached to the second nitrogen;

b) one or more boronic acid groups are attached to a first aromatic moiety which is attached to one nitrogen and one boronic acid and a reactive group are attached to a second aromatic group which second aromatic group is attached to the second nitrogen;

c) one boronic acid group and a reactive group are attached to a first aromatic moiety which first aromatic group is attached to one nitrogen, and a boronic acid group and a reactive group are attached to a second aromatic moiety which is attached to the second nitrogen; and d) one boronic acid is attached to each nitrogen and a reactive group is attached to the heteroaromatic ring.

Preferred embodiments comprise two boronic acid moieties and one polymerizable group or coupling group wherein the aromatic group is a benzyl substituent bonded to the nitrogen and the boronic acid groups are attached to the benzyl ring and may be in the ortho-meta or para-positions.

In some embodiments, the boronic acid substituted viologen as a discrete compound useful for in vitro sensing may be represented by one of the following formulas:

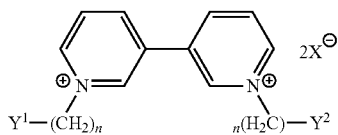

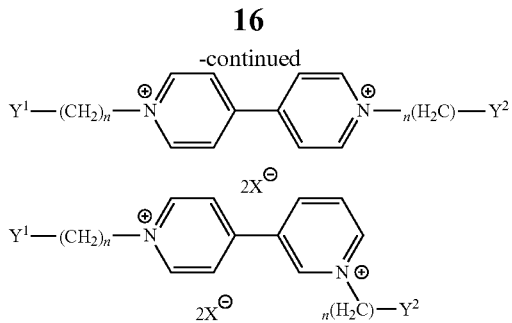

where n=1-3, X is halogen, and $Y^1$ and $Y^2$ are independently selected from phenyl boronic acid (o- m- or p-isomers) and naphthyl boronic acid. In other embodiments, the quencher may comprise a boronic acid group as a substituent on the heterocyclic ring of a viologen.

The quencher precursors suitable for making sensors may be selected from the following:

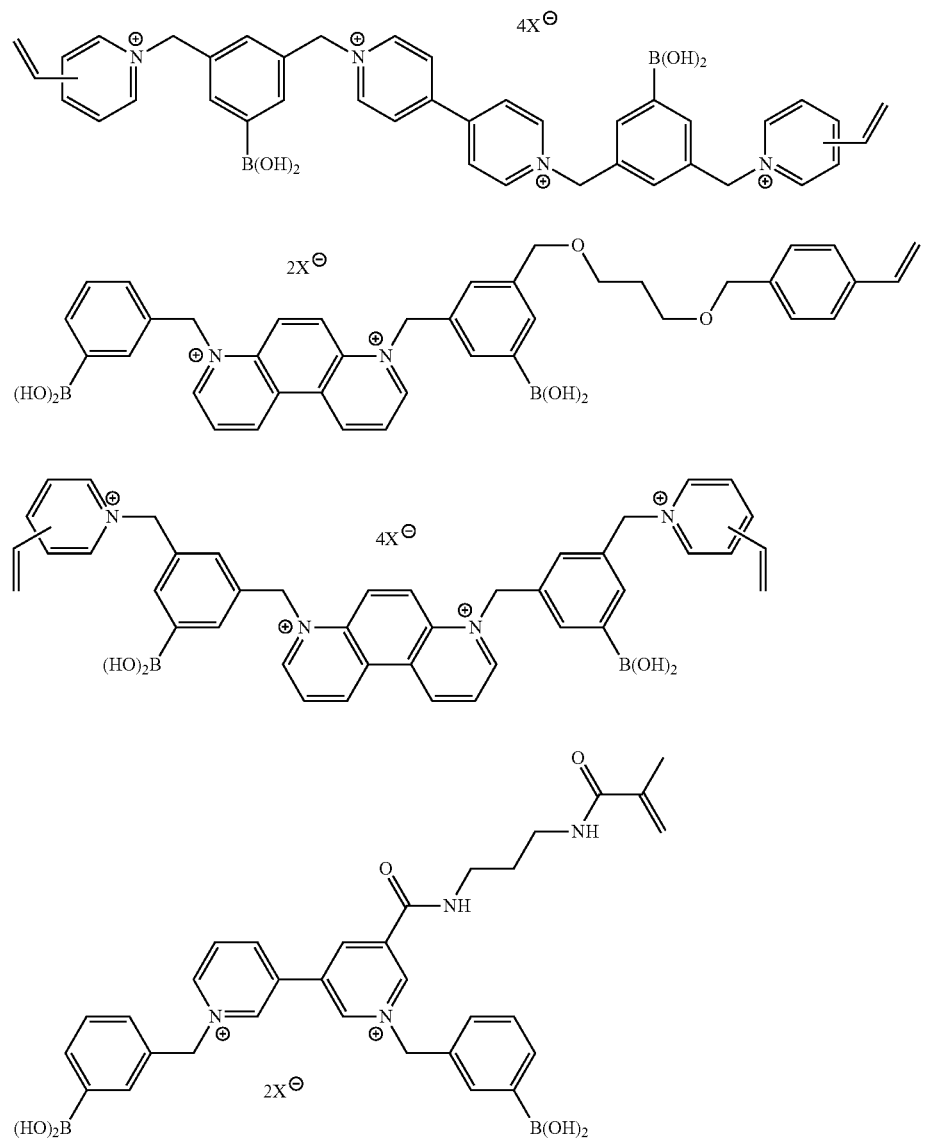

-continued
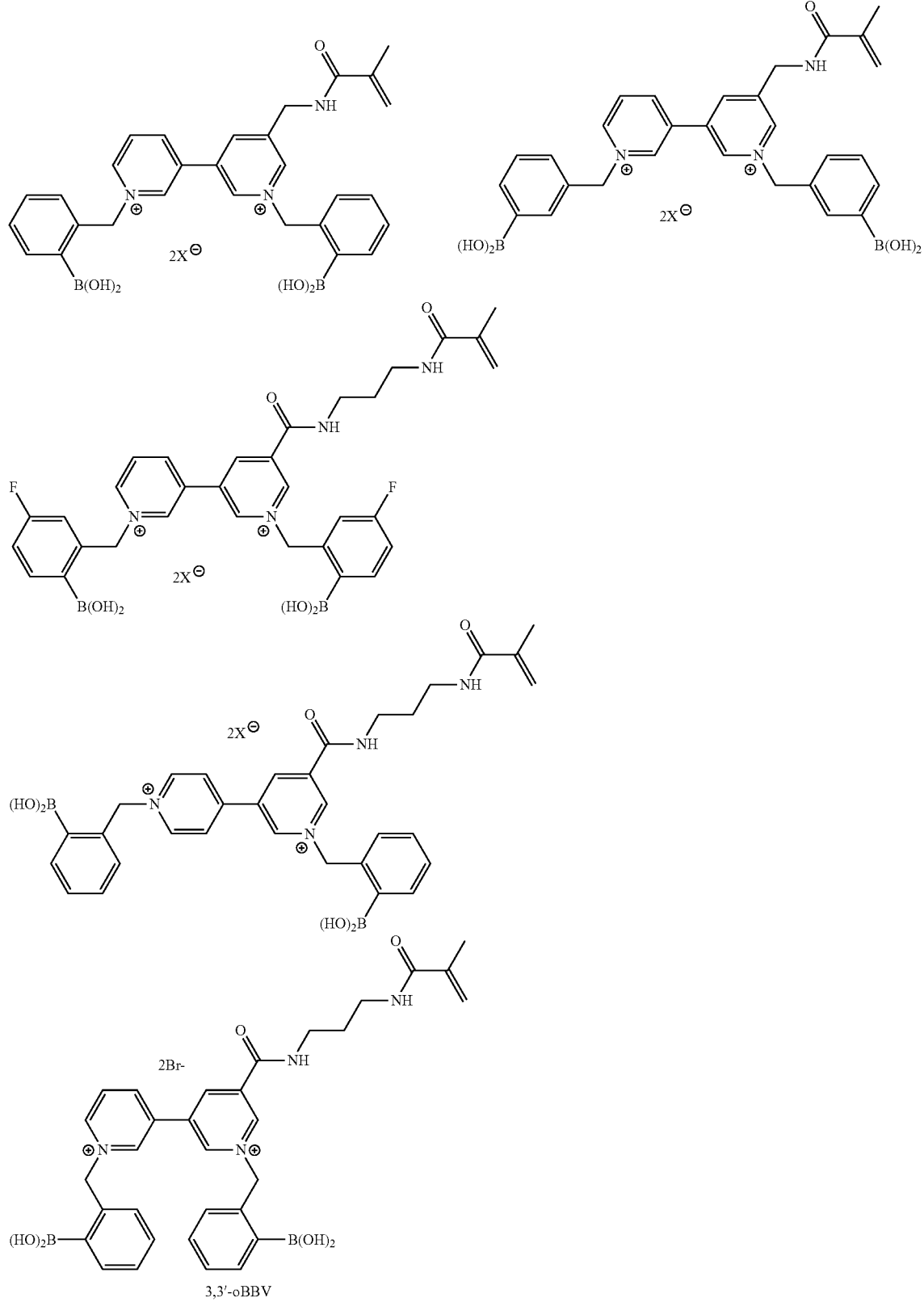
3,3'-oBBV
The quencher precursor 3,3'-oBBV may be used with HPTS-LysMA or HPTS-CysMA to make hydrogels in accordance with certain aspects of the invention.
In certain embodiments, the quenchers are prepared from precursors comprising viologens derived from 3,3'-dipyridyl substituted on the nitrogens with benzylboronic acid groups and at other positions on the dipyridyl rings with a polymerizable group or a coupling group. Representative viologens include:

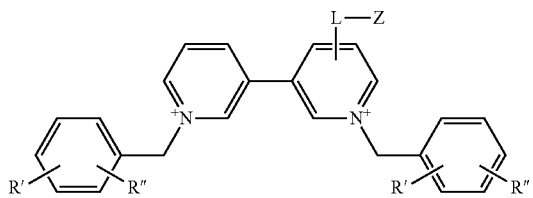

where L is $L^1$ or $L^2$ and is a linking group;
Z is a reactive group; and
R' is —B(OH)$_2$ in the ortho- meta- or para-positions on the benzyl ring and R" is H—; or optionally R" is a coupling group as is defined herein or a substituent specifically used to modify the acidity of the boronic acid such as fluoro- or methoxy-;
L is a divalent moiety that covalently connects the sensing moiety to a reactive group that is used to bind the viologen to a polymer or matrix. Examples of L include those which are each independently selected from a direct bond or, a lower alkylene having 1 to 8 carbon atoms, optionally terminated with or interrupted by one or more divalent connecting groups selected from sulfonamide (—SO$_2$NH—), amide —(C=O)N—, ester —(C=O)—O—, ether —O—, sulfide —S—, sulfone (—SO$_2$—), phenylene —C$_6$H$_4$—, urethane —NH(C=O)—O—, urea —NH(C=O)NH—, thiourea —NH(C=S)—NH—, amide —(C=O)NH—, amine —NR— (where R is defined as alkyl having 1 to 6 carbon atoms) and the like.
Z is either a polymerizable ethylenically unsaturated group selected from but not limited to methacrylamido-, acrylamido-, methacryloyl-, acryloyl-, or styryl- or optionally Z is a reactive functional group, capable of forming a covalent bond with a polymer or matrix. Such groups include but are not limited to —Br, —OH, —SH, —CO$_2$H, and —NH$_2$.

Boronic acid substituted polyviologens are another class of preferred quenchers. The term polyviologen includes: a discrete compound comprising two or more viologens covalently bonded together by a linking group, a polymer comprised of viologen repeat units in the chain, a polymer with viologen groups pendant to the chain, a dendrimer comprised of viologen units, including viologen terminal groups, an oligomer comprised of viologen units, including viologen endgroups, and combinations thereof. Polymers in which mono-viologen groups form a minor component are not included. In certain embodiments, the quenchers are water soluble or dispersible polymers, or crosslinked, hydrophilic polymers or hydrogels sufficiently permeable to glucose to function as part of a sensor. Alternatively the polyviologen boronic acid may be directly bonded to an inert substrate.

A polyviologen quencher as a polymer comprised of viologen repeat units has the formula:

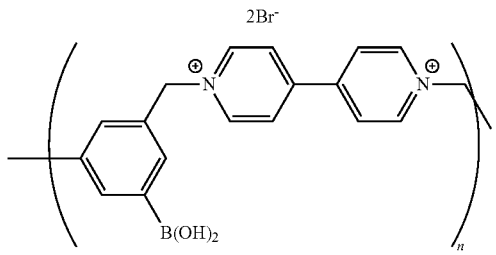

In another embodiment, the polyviologen boronic acid adducts are formed by covalently linking two or more viologen/boronic acid intermediates. The bridging group is typically a small divalent radical bonded to one nitrogen in each viologen, or to a carbon in the aromatic ring of each viologen, or one bond may be to a ring carbon in one viologen and to a nitrogen in the other. Two or more boronic acid groups are attached to the polyviologen. Optionally, the polyviologen boronic acid adduct is substituted with a polymerizable group or coupling group attached directly to the viologen or to the bridging group. The polyviologen moiety may include only one such group. The bridging group may be selected to enhance cooperative binding of the boronic acids to glucose.

The coupling moiety is a linking group as defined previously with the proviso that the linking group is optionally further substituted with a boronic acid, a polymerizable group, an additional coupling group, or is a segment in a polymer chain in which the viologen is a chain unit, a pendant group, or any combination thereof.

In other embodiments, the quencher may be any selected from any of those described in co-pending U.S. application Ser. Nos. 11/296,898; 11/782,553; 11/671,880; 12/113,876; 60/915,372; and 60/949,145; each of which is incorporated herein in its entirety by reference thereto.

Immobilizing Means

In some embodiments, for use in vitro not involving a moving stream, the sensing components are used as individual (discrete) components. The dye and quencher are mixed together in liquid solution, analyte is added, the change in fluorescence intensity is measured, and the components are discarded. Polymeric matrices that can be used to trap the sensing components to prevent leaching need not be present. Optionally, the sensing components are immobilized which allows their use to measure analytes in a moving stream.

For in vivo applications, the sensor is used in a moving stream of physiological fluid which contains one or more polyhydroxyl organic compounds or is implanted in tissue such as muscle which contains said compounds. Therefore, it is preferred that none of the sensing moieties escape from the sensor assembly. Thus, in certain embodiments for use in vivo, the sensing components are part of an organic polymer sensing assembly. Soluble dyes and quenchers can be confined by a semi-permeable membrane that allows passage of the analyte but blocks passage of the sensing moieties. This can be realized by using as sensing moieties soluble molecules that are substantially larger than the analyte molecules (molecular weight of at least twice that of the analyte or greater than 1000 preferably greater than 5000); and employing a selective semi-permeable membrane such as a dialysis or an ultrafiltration membrane with a specific molecular weight cutoff between the two so that the sensing moieties are quantitatively retained.

In some embodiments, the sensing moieties are immobilized in an insoluble polymer matrix, which is freely permeable to glucose. The polymer matrix is comprised of organic, inorganic or combinations of polymers thereof. The matrix may be composed of biocompatible materials. Alternatively, the matrix is coated with a second biocompatible polymer that is permeable to the analytes of interest.

The function of the polymer matrix is to hold together and immobilize the dye and quencher moieties while at the same time allowing contact with the analyte (e.g., polyhydroxyl compounds, H$^+$ and OH$^-$), and binding of the polyhydroxyl compound to the quencher. To achieve this effect, the matrix must be insoluble in the medium, and in close association with it by establishing a high surface area interface between matrix and analyte solution. For example, an ultra-thin film or microporous support matrix is used. Alternatively, the matrix is swellable in the analyte solution, e.g. a hydrogel matrix is used for aqueous systems. In some instances, the sensing polymers are bonded to a surface such as the surface of a light conduit, or impregnated in a microporous membrane. In all cases, the matrix must not interfere with transport of the analyte to the binding sites so that equilibrium can be established between the two phases. Techniques for preparing ultra-thin films, microporous polymers, microporous sol-gels, and hydrogels are established in the art. All useful matrices are defined as being analyte permeable.

Hydrogel polymers are used in some embodiments. The term, hydrogel, as used herein refers to a polymer that swells substantially, but does not dissolve in water. Such hydrogels may be linear, branched, or network polymers, or polyelectrolyte complexes, with the proviso that they contain no soluble or leachable fractions. Typically, hydrogel networks are prepared by a cross-linking step, which is performed on water-soluble polymers so that they swell but do not dissolve in aqueous media. Alternatively, the hydrogel polymers are prepared by copolymerizing a mixture of hydrophilic and cross-linking monomers to obtain a water swellable network polymer. Such polymers are formed either by addition or condensation polymerization, or by combination process. In these cases, the sensing moieties are incorporated into the polymer by copolymerization using monomeric derivatives in combination with network-forming monomers. Alternatively, reactive moieties are coupled to an already prepared matrix using a post polymerization reaction. Said sensing moieties are units in the polymer chain or pendant groups attached to the chain.

The hydrogels useful in this invention are also monolithic polymers, such as a single network to which both dye and quencher are covalently bonded, or multi-component hydrogels. Multi-component hydrogels include interpenetrating networks, polyelectrolyte complexes, and various other blends of two or more polymers to obtain a water swellable composite, which includes dispersions of a second polymer in a hydrogel matrix and alternating microlayer assemblies.

Monolithic hydrogels are typically formed by free radical copolymerization of a mixture of hydrophilic monomers, including but not limited to HEMA, PEGMA, methacrylic acid, hydroxyethyl acrylate, N-vinyl pyrrolidone, acrylamide, N,N'-dimethyl acrylamide, and the like; ionic monomers include methacryloylaminopropyl trimethylammonium chloride, diallyl dimethyl ammonium. chloride, vinyl benzyl trimethyl ammonium chloride, sodium sulfopropyl methacrylate, and the like; crosslinkers include methylene bisacrylamide, ethylene dimethacrylate, PEGDMA, trimethylolpropane triacrylate, and the like. The ratios of monomers are chosen to optimize network properties including permeability, swelling index, and gel strength using principles well established in the art. In one embodiment, the dye moiety is derived from an ethylenically unsaturated derivative of a dye molecule, such as 8-acetoxypyrene-1,3,6-N,N',N"'-tris(methacrylamidopropylsulfonamide), the quencher moiety is derived from an ethylenically unsaturated viologen such as 4-N-(benzyl-3-boronic acid)-4'-N'-(benzyl-4ethenyl)-dipyridinium dihalide (m-SBBV) and the matrix is made from HEMA and PEGDMA. The concentration of dye is chosen to optimize emission intensity. The ratio of quencher to dye is adjusted to provide sufficient quenching to produce the desired measurable signal.

In some embodiments, a monolithic hydrogel is formed by a condensation polymerization. For example, acetoxy pyrene trisulfonyl chloride is reacted with an excess of PEG diamine to obtain a tris-(amino PEG) adduct dissolved in the unreacted diamine. A solution of excess trimesoyl chloride and an acid acceptor is reacted with 4-N-(benzyl-3-boronic acid)-4'-N'-(2 hydroxyethyl) bipyridinium dihalide to obtain an acid chloride functional ester of the viologen. The two reactive mixtures are brought into contact with each other and allowed to react to form the hydrogel, e.g. by casting a thin film of one mixture and dipping it into the other.

In other embodiments, multi-component hydrogels wherein the dye is incorporated in one component and the quencher in another are preferred for making the sensor of this invention. Further, these systems are optionally molecularly imprinted to enhance interaction between components and to provide selectivity for glucose over other polyhydroxy analytes. Preferably, the multicomponent system is an interpenetrating polymer network (IPN) or a semi-interpenetrating polymer network (semi-IPN).

The IPN polymers are typically made by sequential polymerization. First, a network comprising the quencher is formed. The network is then swollen with a mixture of monomers including the dye monomer and a second polymerization is carried out to obtain the IPN hydrogel.

The semi-IPN hydrogel is formed by dissolving a soluble polymer containing dye moieties in a mixture of monomers including a quencher monomer and polymerizing the mixture. In some embodiments, the sensing moieties are immobilized by an insoluble polymer matrix which is freely permeable to polyhydroxyl compounds. Additional details on hydrogel systems have been disclosed in US Patent Publications Nos. US2004/0028612, and 2006/0083688 which are hereby incorporated by reference in their entireties.

In one embodiment, the boronic acid substituted viologen may be covalently bonded to a fluorescent dye. The adduct may be a polymerizable compound or a unit in a polymer. One such adduct for example may be prepared by first forming an unsymmetrical viologen from 4,4'-dipyridyl by attaching a benzyl-3-boronic acid group to one nitrogen and an aminoethyl group to the other nitrogen atom. The viologen is condensed sequentially first with 8-acetoxy-pyrene-1,3,6-trisulfonyl chloride in a 1:1 mole ratio followed by reaction with excess PEG diamine to obtain a prepolymer mixture. An acid acceptor is included in both steps to scavenge the byproduct acid. The prepolymer mixture is crosslinked by reaction with a polyisocyanate to obtain a hydrogel. The product is treated with base to remove the acetoxy blocking group. Incomplete reaction products and unreacted starting materials are leached out of the hydrogel by exhaustive extraction with deionized water before further use. The product is responsive to glucose when used as the sensing component as described herein.

Alternatively, such adducts are ethylenically unsaturated monomer derivatives. For example, dimethyl bis-bromomethyl benzene boronate is reacted with excess 4,4'-dipyridyl to form a half viologen adduct. After removing the excess dipyridyl, the adduct is further reacted with an excess of bromoethylamine hydrochloride to form the bis-viologen adduct. This adduct is coupled to a pyranine dye by reaction with the 8-acetoxypyrene-tris sulfonyl chloride in a 1:1 mole ratio in the presence of an acid acceptor followed by reaction with excess aminopropylmethacrylamide. Finally, any residual amino groups may be reacted with methacrylol chloride. After purification, the dye/viologen monomer may be copolymerized with HEMA and PEGDMA to obtain a hydrogel.

Ratiometric pH Sensing

Ratiometric pH sensing is known. See e.g., U.S. Pat. Publication Nos. 2006/0105174; 2005/0090014; incorporated herein in their entirety by reference. In certain embodiments, the indicator system comprises a fluorophore (e.g., a fluorescent indicator dye) that exists in two forms (an acid form and a base form). The ratio of the emission intensity at the two wavelengths can be used to measure pH independent of the fluorophore concentration. The fluorescent indicator dyes suitable for ratiometric pH sensing may be: (1) dyes that exhibit dual excitation wavelengths (corresponding to acid and conjugate base forms) and single emission wavelengths (e.g., HPTS dyes); (2) single excitation wavelengths and dual emission wavelengths (acid and base forms); or (3) dual excitation—dual emission dyes. Some dyes, such as the SNARF or SNAFL dyes may have both dual-emission and dual-excitation properties. However a dual-dual dye, e.g., SNARF can be used as a single-dual or a dual-single.

Dual emission fiber-optic sensors based on seminapthofluorescein and carboxynaphthofluorescein have been described that rapidly and reliably correlate intensity ratios to pH. See e.g., respectively, Xu, Z., A. Rollins, et al. (1998) "A novel fiber-optic pH sensor incorporating carboxy SNAFL-2 and fluorescent wavelength-ratiometric detection" Journal of Biomedical Materials Research 39: 9-15, and Song, A., S. Parus, et al. (1997) "High-performance fiber-optic pH microsensors for practical physiological measurements using a dual-emission sensitive dye" Analytical Chemistry 69: 863-867. The extensive photobleaching observed for these dyes may be accounted for by the ratiometric approach, but it would still limit the useful lifetime of the sensor.

The fluorescent dye 8-hydroxy-1,3,6-pyrene trisulfonic acid trisodium salt (HPTS) consists of a pyrene core with three sulfonic acid groups and a hydroxyl group that imparts pH sensitivity around a pKa of approximately 7.3 (Wolfbeis, O. S., E. Fuerlinger, et al. (1983). "Fluorimetric analysis. I. Study on fluorescent indicators for measuring near neutral ('physiological') pH values." Fresneius' Z. Anal. Chem. 314 (2): 119-124); Wolfbeis et al. also have several patents on immobilized HPTS. Yafuso and Hui describe another immobilized fluorescent dye pH sensor in U.S. Pat. No. 4,886,338; incorporated herein in its entirety by reference thereto. HPTS exhibits two excitation wavelengths, one at 405 nm and one at 457 nm, which correspond to the acid and its conjugate base (Agayn, V. I. and Dr. R. Walt (1993). "Fiber-optic sensor for continuous monitoring of fermentation pH." Biotechnology 72(6):6-9). The subsequent pH-dependent shift in excitation maximum about the pKa of 7.3 enables dual-excitation/single emission ratiometric detection in the physiological range. This, together with a low toxicity (Lutty, G. A. (1978). "The acute intravenous toxicity of stains, dyes, and other fluorescent substances." Toxical Pharmacol. 44: 225-229) and insensitivity to oxygen concentration (Zhujun, Z. and W. R. Seitz (1984). "A fluorescence sensor for quantifying pH in the range from 6.5 to 8.5." Analytical Chimica Acta 160: 47-55), makes HPTS a suitable probe for physiological and bioprocess pH measurements.

The presence of the three strongly anionic sulfonic acid groups allows for HPTS to be immobilized by ionic binding to cationic supports. To date, covalent attachment of HPTS has been via sulfonamide coupling (U.S. Pat. No. 4,798,738). While effective in immobilizing the dye and preserving pH sensitivity, polymer substrates are limited to those that contain primary amines. In addition, amine groups which remain on the substrate after coupling will affect the local pH inside the polymer matrix. The dye has been covalently attached to controlled pore glass (Offenbacher, H., O. S. Wolfbeis, et al. (1986). "Fluorescence optical sensors for continuous determination of near-neutral pH values." Sensor Actuator 9: 73-84) and aminoethyl cellulose (Schulman, S. G., S. Chen, et al. (1995). "Dependence of the fluorescence of immobilized 1-hydroxypyrene-3,6,8-trisulfonate on solution pH: extension of the range of applicability of a pH fluorosensor." Anal Chim Acta 304: 165-170) in the development of fluorescence-based pH sensors that operate in neutral and acidic environments, as well as an intravascular blood gas monitoring system where it was used for both pH and $pCO_2$ detection (Gehrich, J. L., D. W. Lubbers, et al. (1986). "Optical fluorescence and its application to an intravascular blood gas monitoring system." IEE TBio-med Eng BME-33: 117-132). Fiber-optic pH sensors have been described with HPTS bound to an anion exchange membrane (Zhujun, Z. and W. R. Seitz (1984)) or resin (Zhang, S., S. Tanaka, et al. (1995). "Fibre-optical sensor based on fluorescent indicator for monitoring physiological pH values." Med Biol Eng Comput 33: 152-156) and fixed to the tip of the optical fiber.

For example U.S. Pat. No. 5,114,676 (incorporated by reference herein in its entirety) provides a pH sensor with a fluorescent indicator which may be covalently attached to a particle or to a microcrystalline cellulose fiber. The sensor comprises an optically transparent substrate, a thermoplastic layer and a hydrogel. Part of the particle with the indicator attached thereto is imbedded in a thermoplastic layer that is coated on the substrate and mechanically adhered using heat and pressure. The majority of the particle/indicator is imbedded within a hydrogel layer that is applied over the thermoplastic layer. The pH sensor is applied to the tip of an optical waveguide.

Furthermore, with the recent availability of low cost UV LEDs, the dye can be measured with relatively inexpensive instrumentation that combines UV and blue LEDs and a photodiode module. Such a setup has been described (Kostov, Y., P. Harms, et al. (2001). "Low-cost microbioreactor for high-throughput bioprocessing." Biotechnol Bioeng 72: 346-352) to detect the pH of a high throughput microbioreactor system via HPTS directly dissolved in the fermentation media.

The presence of hydroxyl (—OH) groups on dyes such as HPTS and its derivatives make these dyes sensitive to pH changes in the environment. The pH-dependent ionization of the hydroxyl group causes these dyes to have a pH-dependent absorption spectra with different absorption maxima in its acidic form and basic form. The first absorption maximum is the first excitation wavelength and the second absorption maximum is the second excitation wavelength. The amounts of light absorbed by the fluorescent dye at the first excitation wavelength and the second excitation wavelength depend on or relate to the pH of the medium the fluorescent dye is in contact with. The amount of light emitted by the dye (e.g., the fluorescent emission intensity) at the emission wavelength depends on the amount of light absorption when the dye is irradiated at the excitation wavelength. Since the absorption is affected by the pH of the medium, the fluorescent emission is also affected by the pH. This provides the basis for the pH determination while being able to simultaneously measure the polyhydroxyl compound concentration.

In one embodiment of the present invention, ratiometric pH sensing is accomplished using an optical sensor comprising at least one excitation light source operably coupled to the proximal end region of an optical fiber, wherein the fiber has disposed along its distal end region within the light path of the fiber, an indicator system configured to generate a detectable emission signal in response to the excitation light. Preferred embodiments of the sensor further comprise optical means for sending the emission signal to a detector. Such optical means are well known in the art, and may involve e.g., a mirror to return light, filters, lens, beam splitters, and optical fiber bundles and split configurations.

In some embodiments, the indicator system comprises a fluorophore that exhibits at least two different forms and a pH-dependent shift between these different forms, where this shift can be detected as a change in the emission intensity at a single wavelength or at two different wavelengths. For example, one indicator system for ratiometric pH sensing comprises an fluorescent dye (e.g., HPTS) that absorbs light at two different wavelength maxima's ($\lambda_{acid}$ and $\lambda_{base}$) depending on whether the dye is in its acid or base forms, and it emits light at a single longer emission wavelength. More particularly, as pH is increased, HPTS shows an increase in absorbance corresponding to the $\lambda_{base}$ and a decrease in absorbance corresponding to the $\lambda_{acid}$. These changes are due to the pH-dependent ionization of the hydroxyl group. The emission spectrum for HPTS is independent of pH, with a peak emission wavelength of about 511 nm, but the intensity of the emitted light depends on the amount of light absorbed (which varies with pH and the excitation wavelength). So for example, if one excites HPTS at a given pH with light of a first wavelength (e.g., $\lambda_{acid}$), one can measure the emission intensity at the single emission wavelength; the intensity will depend on the form of the dye (i.e., degree of ionization— which depends on the pH). One can also excite at a second wavelength (e.g., $\lambda_{base}$) and measure the emission intensity at the same given pH. The ratio of the emission intensities relates to the pH and is independent of the amount of the dye as well as certain optical artifacts in the system. It is noted that any excitation wavelengths may be used for the ratiometric sensing, but the $\lambda_{acid}$ and $\lambda_{base}$ are preferred in accordance with one embodiment of the invention. The wavelength at which the absorption is the same for the acid and base forms of the dye is called the isobestic point—excitation at this wavelength ($\lambda_{iso}$) may also be used in ratiometric sensing in accordance with other preferred variations to the invention. When a ratio of emission intensities (e.g., $I_{base}/I_{iso}$ or $I_{base}/I_{acid}$) is plotted against pH, a standard or calibration curve is generated (See e.g., FIGS. 3, 5 and 9). The ratiometric method is similar regardless of whether the dye used is a dual exciter-single emitter (like HPTS), or a single exciter-dual emitter, or a dual exciter-dual emitter, as long as the dye undergoes a pH sensitive shift in form that yields a detectable change in spectral property.

Device and Method for Intravascular Determination of pH and Glucose

In some embodiments of the present invention, the sensing device comprises at least one light source, a detector, and a sensor comprising a fluorescent reporter dye system. In some embodiments, the fluorescent reporter dye system comprises a fluorescent dye operably coupled to an analyte-binding quencher. The dye may be covalently bound to the quencher or merely associated with the quencher. The dye and quencher are operably coupled, which means that in operation, the quencher is in close enough proximity to the dye to interact with and modulate its fluorescence. In some embodiments, the dye and quencher may be constrained together within an analyte-permeable hydrogel or other polymeric matrix. When excited by light of appropriate wavelength, the fluorescent dye emits light (e.g., fluoresces). The intensity of the light is dependent on the extent of quenching which varies with the amount of analyte binding. In other embodiments, the fluorescent dye and the quencher may be covalently attached to hydrogel or other polymeric matrix, instead of to one another.

In some embodiments, the method uses a sensor to monitor the pH of the media and the concentration of analyte in vitro. In other embodiments, the method uses a sensor to monitor the pH and analyte concentration in vivo. In still other embodiments, the measured pH value can also be used to more correctly determine glucose concentration in vitro or in vivo. Specifically, the simultaneous measurement of the pH value and the glucose concentration would enable real time correction of the signal of glucose response. Although it will be appreciated that the device in accordance with some embodiments comprises a sensor that may be used only to determine pH or analyte concentration, the correction of which for pH may be done by conventional two sensor technologies or by testing the blood pH in vitro.

One embodiment, which provides a device for determining pH and the concentration of a polyhydroxyl compound simultaneously, comprises a sensor having a fluorescent dye operably coupled to a quencher, a means for delivering one or more excitation wavelengths to said sensor, and a means for detecting fluorescence emissions from the sensor.

Another embodiment provides a device for determining the pH and the polyhydroxyl compound concentration in a physiological fluid. It comprises a water-insoluble polymer matrix, where the polymer matrix is permeable to polyhydroxyl compound. A fluorescent dye is associated with the polymer matrix. The fluorescent dye is configured to absorb light at a first excitation wavelength and a second excitation wavelength, and to emit light at an emission wavelength. The device further comprises a quencher comprising an aromatic boronic acid substituted viologen, adapted to reversibly bind an amount of polyhydroxyl compound dependent on the polyhydroxyl compound concentration. The quencher is associated with the polymer matrix and is operably coupled to the fluorescent dye. The quencher is configured to reduce the light intensity emitted by the fluorescent dye, which corresponds to the amount of bound polyhydroxyl compound. The device also has at least one excitation light source and an emission light detector.

In one embodiment, the device comprises an optical fiber comprising a cavity disposed therein and having immobilized within the cavity an indicator system as described above (e.g., a fluorophore operably coupled to a glucose binding moiety/quencher and an immobilizing polymeric matrix). The device further comprises a light source and a detector.

One embodiment provides a method for determining the pH and the polyhydroxyl compound concentration with a fluorescent dye. The method comprises providing a sensor having a fluorescent dye operably coupled to a quencher, contacting the sensor with the medium to be analyzed, irradiating the sensor at a first excitation wavelength, detecting a first fluorescence emission of the sensor at an emission wavelength, irradiating the sensor at a second excitation wavelength, measuring a second fluorescence emission of the sensor at the emission wavelength, comparing the ratio of the first and second emissions with a pH calibration curve to determine the pH of the sample, and correlating the emission quenching with a standard curve at the known pH to determine the polyhydroxyl compound concentration in the medium.

Other algorithms are known for ratiometric pH sensing and may be used in accordance with embodiments of the present invention. A controller, such as a computer or dedicated device, may be used in some embodiments to control the operations, including application of the excitation light, monitoring of detector signals, determining ratios, correlating ratios with calibration curves, correlating glucose signals with standard curves, correcting for pH changes, running routine sensor calibration operations, prompting operator actions, integrating user data input (e.g., finger stick glucose measurements) as programmed to maintain accuracy, and other functions.

With respect to FIG. 1, a sensing device 100 in accordance with one embodiment of the present invention comprises at least one light source 11 (e.g., an excitation light source), a detector 15 (e.g., an emission light detector), and a sensor 13 comprising a fluorescent dye operably coupled to a quencher and an optional polymer matrix. In some embodiments, the light source 11 may be adapted to selectively deliver two or more different wavelength for the excitations of fluorescent dyes. This type of light source may be a tunable light source. In other embodiments, one or more light sources may be used in conjunction with an optical filter 12 for attenuating the wavelengths. In other embodiments, more than one light source 11 may be used to deliver different excitation wavelengths. Such light source is also a means for delivering a first and a second excitation wavelength to the sensor.

The sensor 13 comprises a fluorescent dye that is sensitive to both the pH and the polyhydroxyl compound (e.g., sugar or glucose) concentration of the medium when the dye is operably coupled to a quencher. Such fluorescent dye exhibits a shift in excitation wavelength maximum with a corresponding shift in pH of the local environment of the fluorescent dye. As the pH of the local environment changes, the absorption at a first excitation wavelength may increase, while the absorption at a second excitation wavelength decreases, or vice versa. The change in absorption at a selected wavelength can affect the level of fluorescence emission, therefore ultimately permitting pH detection. The pH detection is independent of the concentration of the polyhydroxyl compound in the environment. A suitable fluorescent dye is also susceptible to quenching by molecules such as viologens. When the fluorescent dye is operably coupled to a quencher (e.g., a viologen), the fluorescence emission is attenuated. The quencher may be substituted with an aromatic boronic acid moiety that is capable of providing glucose recognition. The boronic acid reacts reversibly with glucose in aqueous media to form boronate ester, and the extent of such reaction is related to the glucose concentration in the medium. As more glucose is available to react with the quencher, the extent of quenching decreases. As a result, the attenuation of fluorescence emission by the quencher is dependent on the concentration of the polyhydroxyl compound (e.g., glucose) to be detected.

A detector 15 is used to detect the fluorescent emission and in preferred embodiments, may be linked to the electronic control 20 for analysis. Optical filters, e.g., 14, can be placed between the sensor 13 and the detector 15 for wavelength selection. Other optical components may also be utilized, e.g., mirrors, collimating and/or focusing lenses, beam splitters, etc. Optical fibers can be used to deliver selected wavelengths to the sensor and to deliver the fluorescence emission from the sensor to the detector. The light source and the detector may be controlled by electronic control 20 such as a computer.

One embodiment of this invention provides a method for measuring pH and polyhydroxyl compound concentration with a single fluorescent dye. Measurements can be carried out in vitro or in vivo. It may be necessary to calibrate the sensor prior to performing the first measurement. This may be done by first acquiring the absorbance spectra of the sensor at various pH levels to determine the wavelengths where isobestic point and absorption maxima for acid and base forms occur and then acquiring the emission signals from at least two of these wavelengths at at least one known pH and glucose concentration.

For the pH and polyhydroxyl concentration measurements, the sensor 13 is first placed in contact with a sample. The sensor 13 is then irradiated at the first excitation wavelength followed by the second excitation wavelength. The first and second excitation wavelengths are typically chosen near the wavelength of the absorption maximum for the acidic form of the fluorescent dye ($\lambda_{acid}$), the wavelength of the absorption maximum for the basic form of the fluorescent dye ($\lambda_{base}$), or the wavelength of the isobestic point ($\lambda_{iso}$), or other selected wavelength. The ratio of the emissions from the first and second excitation wavelengths are used to determine the sample pH. Either the first or second emission, once corrected for pH, can be used to determine the sample glucose concentration.

In variations to the sensing device shown in FIG. 1, the detector may be a standard photodiode detector. There may be two diode detectors, one for a reference and one for the emission signal. Instead of diode detectors, the optical fiber carrying sensor output (fluorescent emission and/or reflected excitation light) may provide input directly to a spectrophotometer or microspectrometer. In a preferred embodiment, the detector comprises a microspectrometer such as the UV/VIS Microspectrometer Module manufactured by Boehringer Ingelheim.

Figure 2:
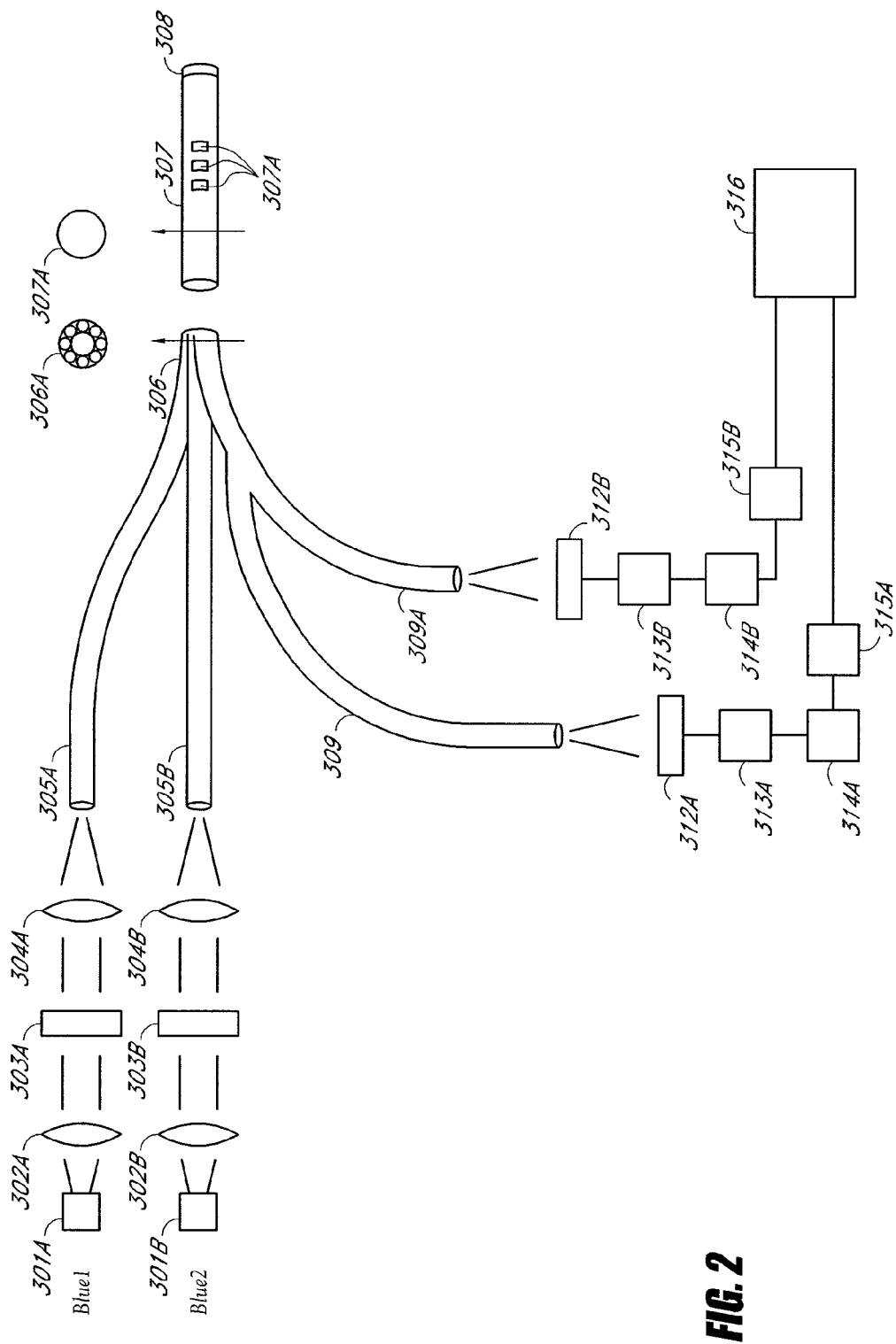
FIG. 2 shows a glucose and pH sensor and optical system comprising two excitation light sources and two detectors in accordance with one embodiment of the present invention.

FIG. 2 shows one embodiment of an optical system that may be used in accordance with preferred aspects of the present invention. With reference to FIG. 2, certain embodiments comprise at least two light sources, 301A and 301B. The light sources generate excitation light that may be transmitted (as illustrated) through collimator lenses 302A and 302B. In certain embodiments, the resulting light from collimator lenses may be transmitted (as illustrated) to interference filters 303A and 303B. In certain embodiments, the resulting light from interference filters may be focused (as illustrated) by focusing lenses 304A and 304B into fiber optic lines 305A and 305B. In certain embodiments, fiber optic lines merge into a single fiber 306 that is continuous with the sensor 307, having the imbedded indicator system 307A. The cross-sections of the fibers may vary (as illustrated) from a bundle of fibers surrounding a central optical fiber 306A to a single fiber 307A.

In certain embodiments (as illustrated), the emission light signals generated by the indicator system 307A as well as the excitation light signals are reflected by mirror 308 and transmitted back out of the sensor into the fiber optic outlet lines 309 and 309A. In the illustrated system, the outlet lines are augmented by including two interference filters 312A, 312B and two detectors 313A, 313B. In preferred embodiments, the interference filter 312A is configured to block the excitation light and allow the emission light to pass to detector 313A where the emission light is detected. In certain embodiments, the signal produced by the detector 313A is amplified by the amplifier 314A and converted into a digital signal by analog-to-digital converter 315A and transmitted to computer 316. In certain embodiments, the interference filter 312B is configured to block the emission light and allow the excitation lights to pass to detector 313B where the excitation light is measured. In certain embodiments, the signal produced by the detector 313B is amplified by the amplifier 314B and converted into a digital signal by analog-to-digital converter 315B and transmitted to computer 316. Ratiometric calculations may be employed to substantially eliminate or reduce non-glucose related factors affecting the intensity of the emission light; these methods are disclosed in detail in co-pending U.S. Provisional Application No. 60/888,477, entitled "Optical systems and methods for ratiometric measurement of glucose using intravascular fluorophore sensors," filed herewith on the same day, and incorporated herein in its entirety by reference thereto.

EXAMPLES

Example 1

Figure 3:
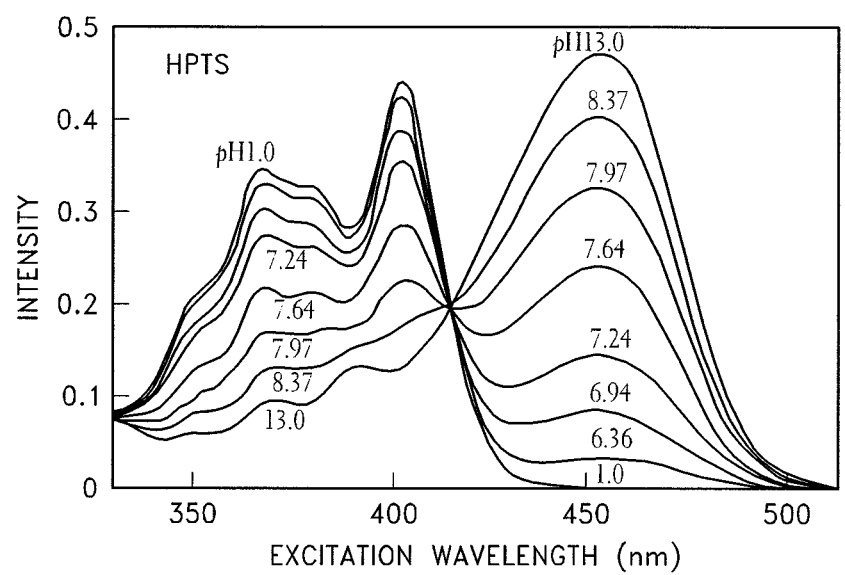
FIG. 3 shows the absorption spectra of HPTS at different pH levels in accordance with some embodiments of the present invention.

FIG. 3 shows an example of the excitation/absorption spectrum of a fluorescent dye, in this case HPTS. From the absorption spectra of the fluorescent dye acquired at different pHs, $\lambda_{acid}$, $\lambda_{base}$ and $\lambda_{iso}$ can be determined. At a lower pH (e.g., more acidic condition), the peak at around 405 nm is higher than the peak at around 460 nm, and is therefore the absorption maximum for the acidic form of the fluorescent dye. At a higher pH (e.g., more basic condition), the peak at round 460 nm is higher than the peak at around 405 nm, therefore is the absorption maximum for the basic form of the fluorescent dye. The $\lambda_{iso}$ would be the wavelength where the absorption is independent of the pH, and it would be, for example, around 422 nm for HPTS.

The first fluorescence emission intensity ($I_x$, which could be $I_{acid}$, $I_{base}$ or $I_{iso}$) at a emission wavelength, resulting from the irradiation at the first excitation wavelength (e.g., $\lambda_{acid}$, $\lambda_{base}$ or $\lambda_{iso}$), is then measured by the detector and the result is stored in the electronic control. Then the sensor is again irradiated at the second excitation wavelength. The second excitation wavelength is different from the first excitation wavelength and can also be selected from $\lambda_{acid}$, $\lambda_{base}$ or $\lambda_{iso}$. The detector will then detect/measure the second fluorescence emission intensity ($I_y$, which could be $I_{acid}$, $I_{base}$ or $I_{iso}$) resulting from the irradiation at the second excitation wavelength (e.g., $\lambda_{acid}$, $\lambda_{base}$ or $\lambda_{iso}$). The ratio of the first and the second fluorescence emissions ($I_x/I_y$) can then be computed. Since the $I_x/I_y$ is independent from the polyhydroxyl concentration, a pH standard curve ($I_x/I_y$ vs. pH) can be plotted without considering the effect of polyhydroxyl concentration.

Example 2

HPTS/MABP4

Figure 4:
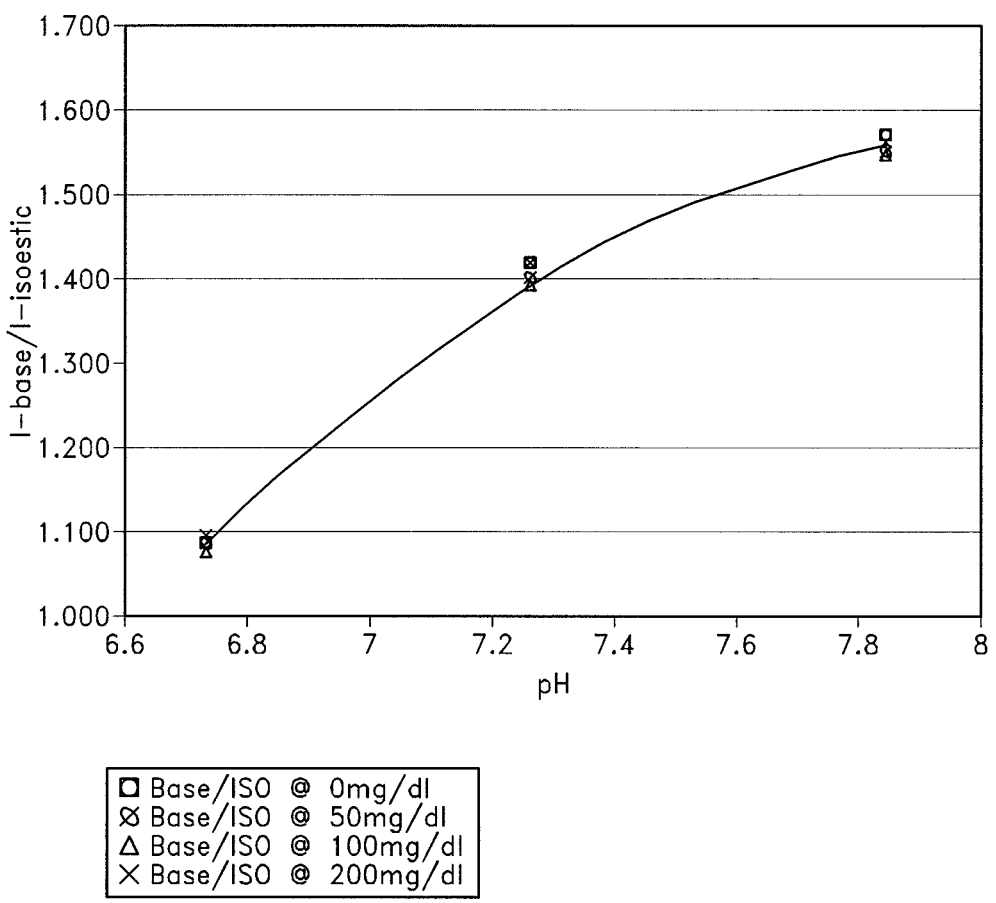
FIG. 4 shows independence of ratiometric pH sensing using HPTS/MABP4 and the $I_{(base)}/I_{(iso)}$ ratio from the glucose concentration. The data are plotted as a ratio of the fluorescence emission corresponding to an excitation at 454 nm (base) and 422 nm (isobestic point) vs. pH in various glucose concentrations in accordance with some embodiments of the present invention.

FIG. 4 shows independent relationship between ratiometric pH sensing using HPTS/MABP4 and the $I_{(base)}/I_{(iso)}$ ratio from glucose concentration. The structure of MABP4 is:

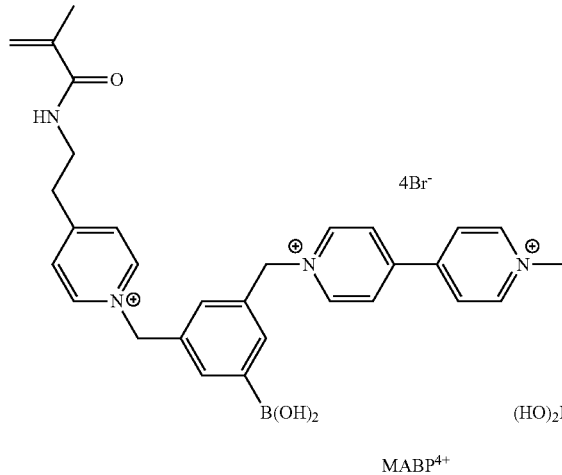

MABP$^{4+}$

The data are plotted as a ratio of the fluorescence emission corresponding to excitation at 454 nm (base) and 422 nm (isobestic point) vs. pH in various glucose concentrations. The changes in glucose concentrations have no discernable effects on the value of $I_{base}/I_{iso}$ at each specific pH. Thus the pH of the sample can be measured using a standard curve of $I_x/I_y$ vs. pH, regardless of the polyhydroxyl compound concentration in the sample. By correlating or comparing the measured $I_x/I_y$ to the standard curve, one may determine the pH of the sample being measured.

Figure 5:
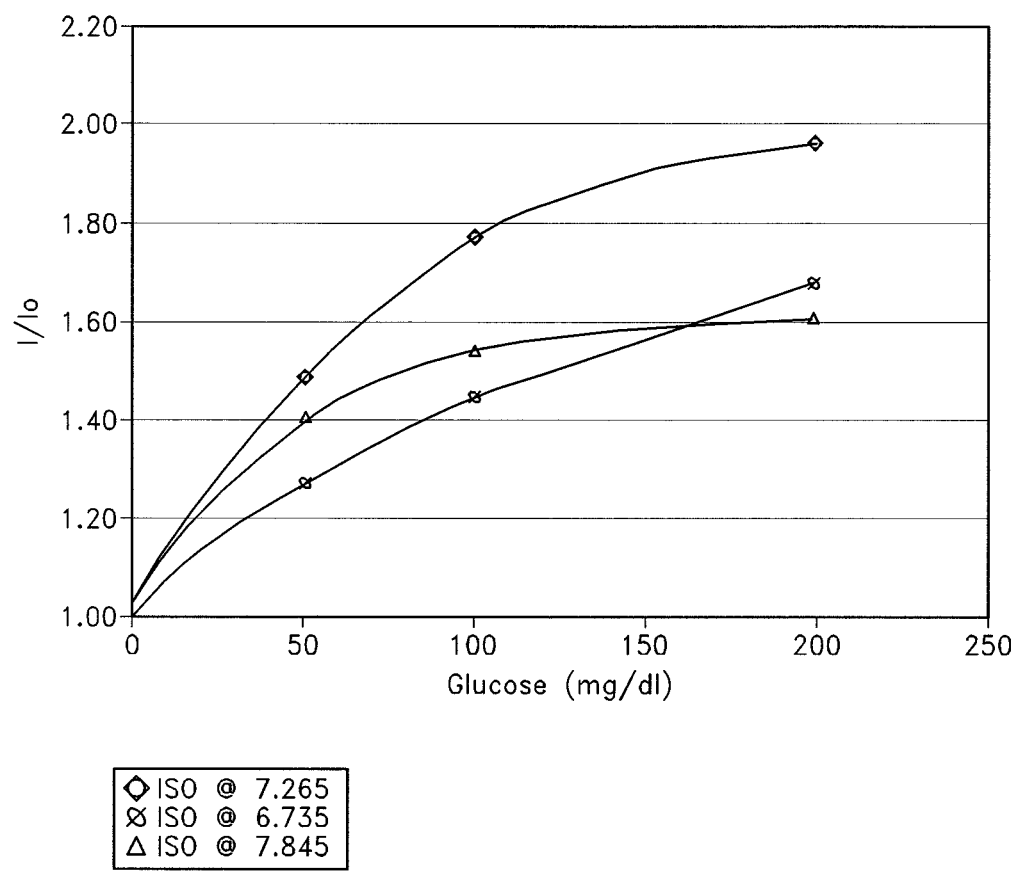
FIG. 5 shows glucose response curves for HPTS/MABP4 excited at 422 nm (isobestic point) at different pH levels in accordance with some embodiments of the present invention.

FIG. 5 shows glucose response curves for HPTS/MABP4 excited at 422 nm (isobestic point) at different pHs. By plotting the ratio of $I_x/I_y$ at various glucose levels (I) to $I_x/I_y$ at zero glucose concentration ($I_0$) vs. glucose concentration, a standard polyhydroxyl response curve can be used to determine the glucose concentration in a sample from measured $I/I_0$ values. However, since $I/I_0$ value is dependent on the pH of the sample, the standard glucose response curve can be affected by the different pH. To circumvent this, several standard glucose response curves at different pHs within the physiological range can be plotted and available for selection by either the electronic control or the operator of the sensor device. When the $I_x/I_y$ measurement of the sample is available, the electronic control or the operator would know the pH of the sample from the standard $I_x/I_y$ vs. pH curve, and the correct standard polyhydroxyl response curve (e.g., glucose response curve) may be used for determining the accurate glucose concentration. Although the examples shown in the figures concern the determination of glucose concentrations, the application of the method and device of the present invention is not limited to detecting glucose concentration. Since the fluorescent system responds to some polyhydroxyl compounds the same way it responds to glucose, the sensor device can be used to measure the concentration of these polyhydroxyl compounds and the pH at the same time.

Example 3

SNARF-1

Figure 6:
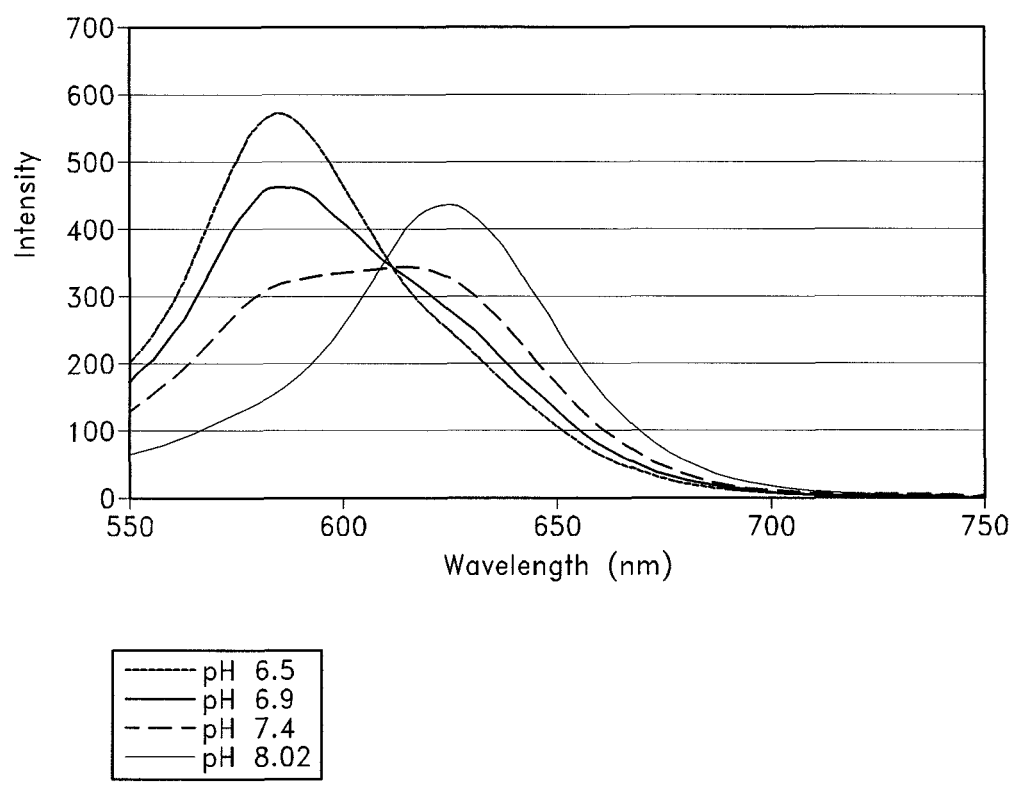
FIG. 6 shows the absorption spectra of SNARF-1 at different Ph levels in solution in accordance with some embodiments of the present invention.
Figure 7:
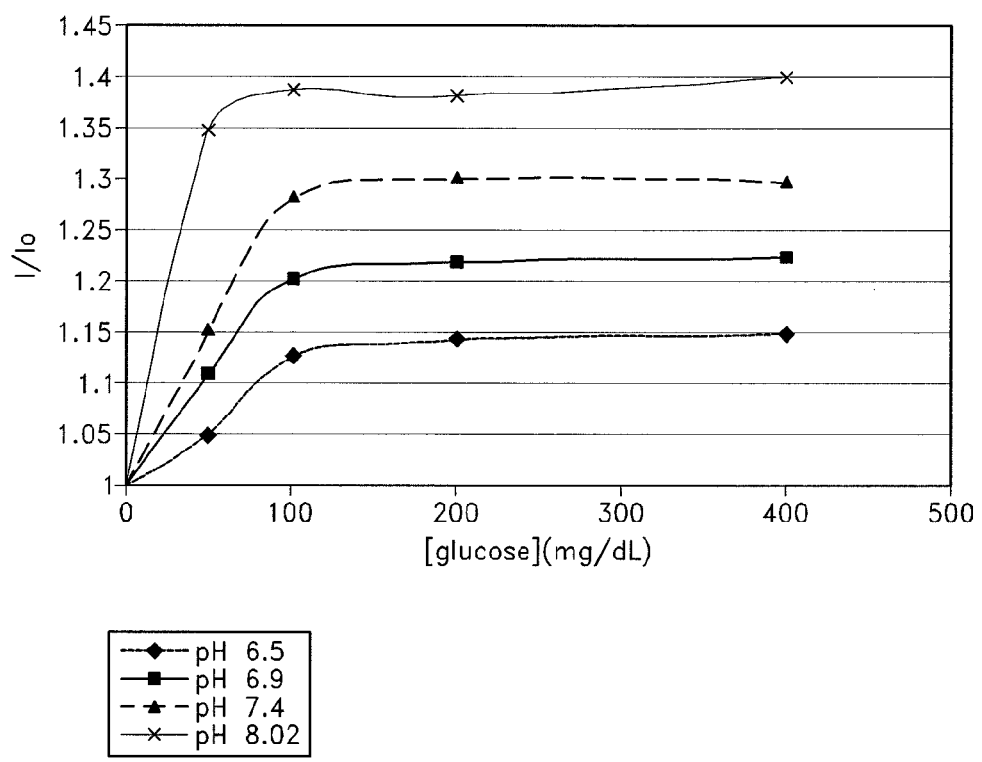
FIG. 7 shows glucose response curves for SNARF-1/3,3'-oBBV in solution at different pH levels excited at 514 nm with emissions at 587 nm in accordance with some embodiments of the present invention.
Figure 8:
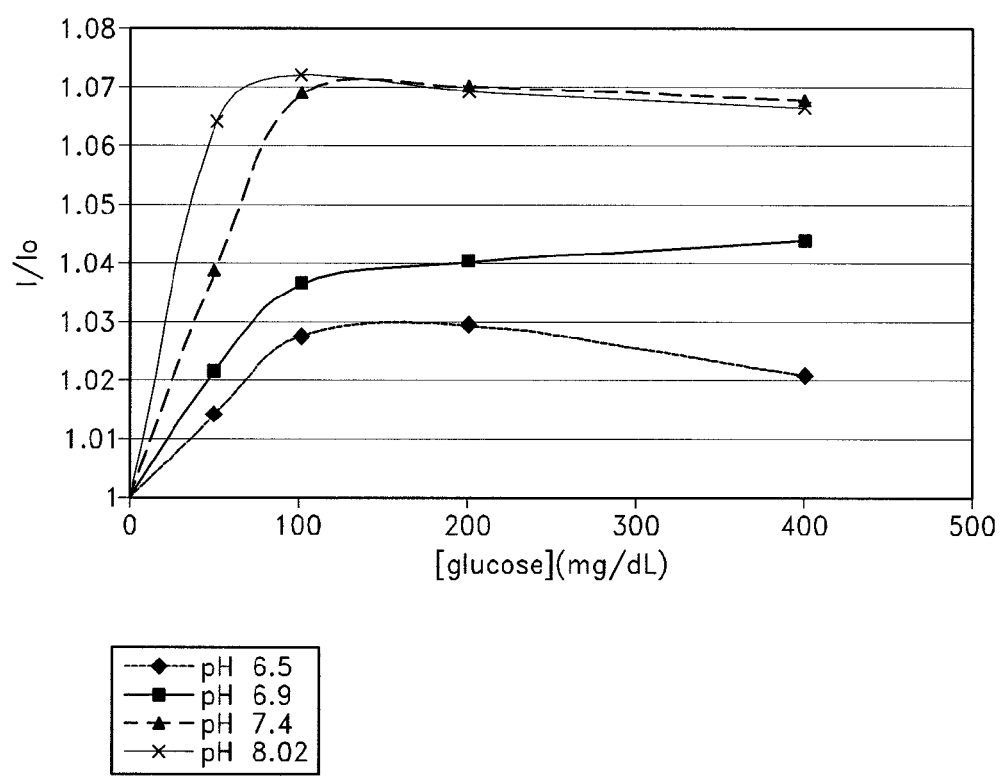
FIG. 8 shows glucose response curves for SNARF-1/3,3'-oBBV in solution at different pH levels excited at 514 nm with emissions at 625 nm in accordance with some embodiments of the present invention.
Figure 9:
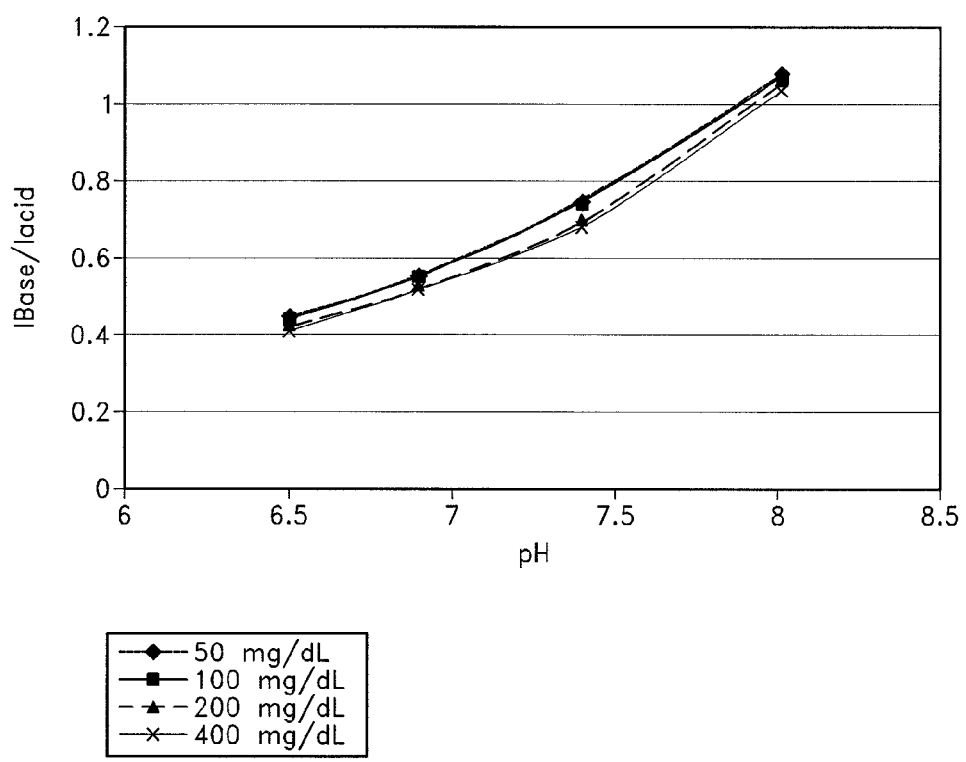
FIG. 9 shows ratiometric sensing of pH at different glucose concentrations with SNARF-1/3,3'-oBBV in solution using the $I_{(base)}/I_{(acid)}$ ratio in accordance with some embodiments of the present invention.

FIG. 6 shows the absorption spectra of SNARF-1 at different pHs in solution. SNARF is a tradename for a class of commercial dyes from Molecular Probes, Inc. These experiments were carried out using SNARF-1. FIGS. 7 and 8 show glucose response curves for SNARF-1/3,3'-oBBV in solution at different pHs determined at 514 nm excitation/587 nm emission (FIG. 7), or at 514 nm excitation/625 nm emission (FIG. 8). FIG. 9 shows ratiometric sensing of pH at different glucose concentrations with SNARF-1/3,3'-oBBV in solution using the $I_{(base)}/I_{(acid)}$ ratio determined at a single excitation wavelength of 514 nm and emission wavelengths of 587 and 625 nm. Thus, the dual-dual dye SNARF-1 may be used operably coupled to the quencher 3,3'-oBBV (in solution) as a single exciter-dual emitter fluorophore to determine both pH ratiometrically and glucose.

Example 4

HPTS-triLysMA/3,3'-oBBV/DMAA

Figure 10:
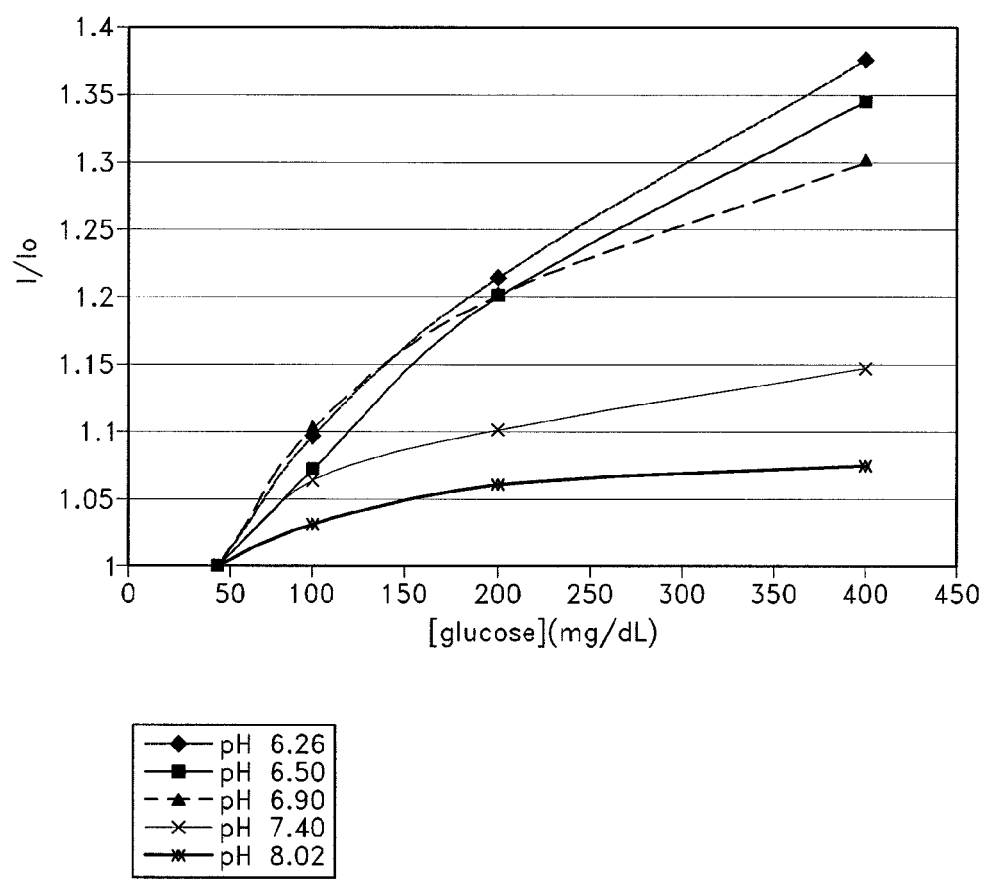
FIG. 10 shows glucose response curves for a DMAA hydrogel comprising HPTS-triLysMA/3,3'-oBBV at different pH levels in accordance with some embodiments of the present invention.
Figure 11:
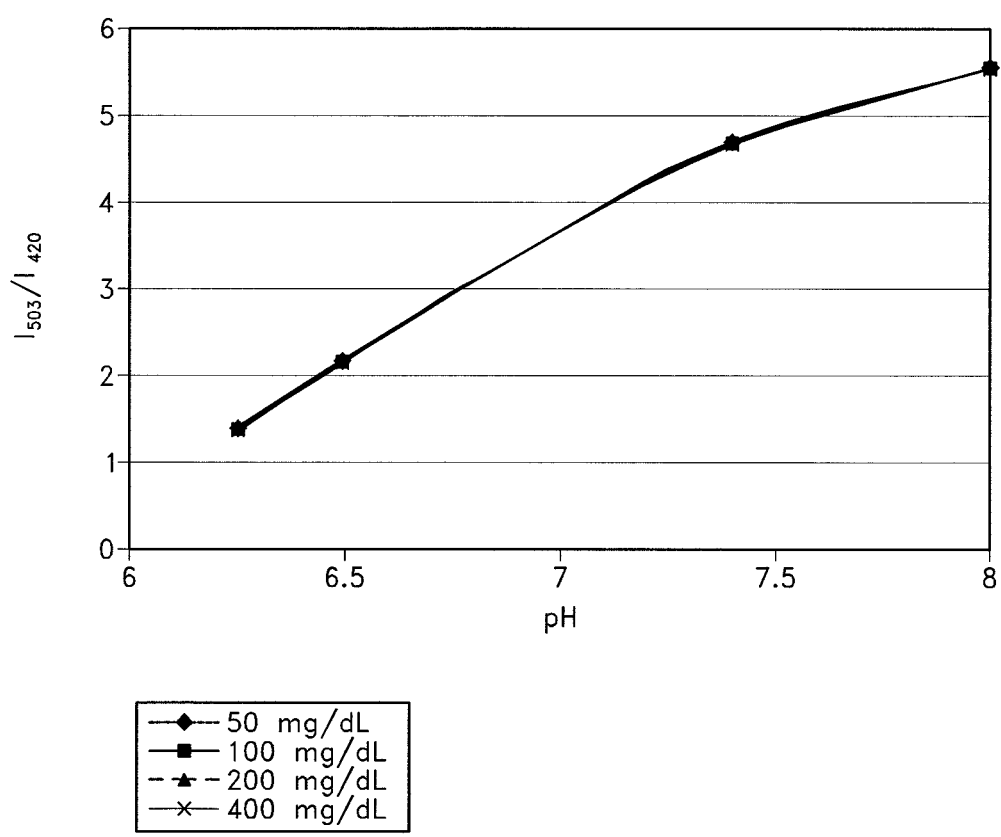
FIG. 11 shows ratiometric sensing of pH at different glucose concentrations using a DMAA hydrogel comprising HPTS-triLysMA/3,3'-oBBV, using the $I_{(base)}/I_{(acid)}$ ratio in accordance with some embodiments of the present invention.

FIG. 10 shows the glucose response of a DMAA hydrogel indicator system comprising HPTS-triLysMA/3,3'-oBBV at different pH levels. FIG. 11 shows ratiometric sensing of pH at different glucose concentrations with the same hydrogel, using the $I_{(base)}/I_{(acid)}$ ratio. It can be seen that this indicator system provides a linear pH curve over the physiologic pH range. For this example, the hydrogel was embedded at the end of an optical fiber. The acid and base emission signals were measured using a hand-held detector.

Example 5

HPTS-triCysMA/3,3'-oBBV/DMMA

Figure 12:
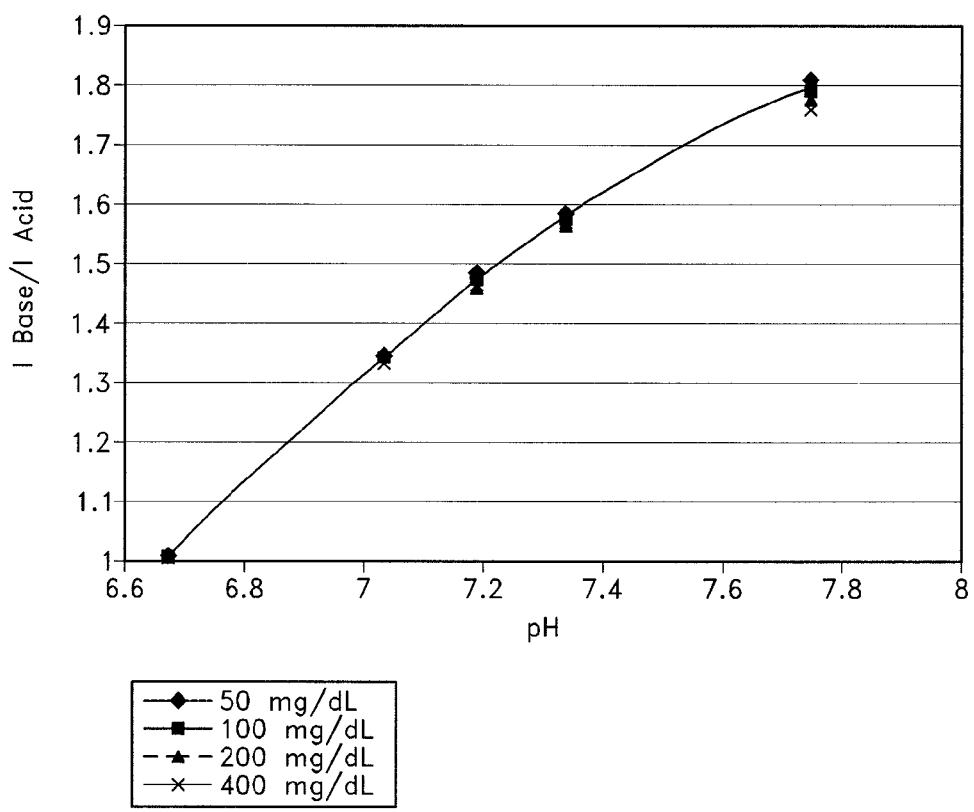
FIG. 12 shows ratiometric sensing of pH at different glucose concentrations using a DMAA hydrogel comprising HPTS-triCysMA/3,3'-oBBV wherein the indicator system is immobilized on the end of an optical fiber, using the $I_{(base)}/I_{(acid)}$ (ratio, in accordance with some embodiments of the present invention.

FIG. 12 shows ratiometric sensing of pH at different glucose concentrations with a DMAA hydrogel indicator system comprising HPTS-triCysMA/3,3'-oBBV, using the $I_{(base)}/I_{(acid)}$ ratio. It can be seen that this indicator system provides a linear pH curve over the physiologic pH range. For this example, the hydrogel was embedded at the end of an optical fiber. The acid and base emission signals were measured using a hand-held detector.

Lifetime Chemistry

In another embodiment, glucose concentrations can be determined by exploiting the phenomena of fluorescence resonance energy transfer (FRET). FRET is the transfer of energy from a donor fluorophore to an acceptor molecule. FRET occurs when the donor fluorophore, which fluoresces at a wavelength absorbed at least in part by the acceptor molecule, is in close proximity to the acceptor such that the donor fluorophore can transfer energy to the acceptor through molecular interactions. The fluorescence lifetime of the fluorophore, where the fluorescence lifetime is the time the fluorophore remains in the excited state, is altered by FRET. Thus, measuring the fluorescence lifetime of the fluorophore allows one to determine whether the fluorophore is bound to the acceptor.

Lifetime can be measured by using a time-domain method where the fluorophore is excited by a brief pulse of excitation light and the fluorescence intensity is measured over time. The excitation pulse can be a pulse from a laser with a duration in the picoseconds range up to a duration of about a few nanoseconds. In other embodiments, the pulse duration can be greater than about a few nanoseconds. The fluorescence intensity of the fluorophore as a function of time is given by the equation:

$$I(t) = I_0 * \exp(-t/\tau) \quad \text{Equation 1}$$

Figure 13:
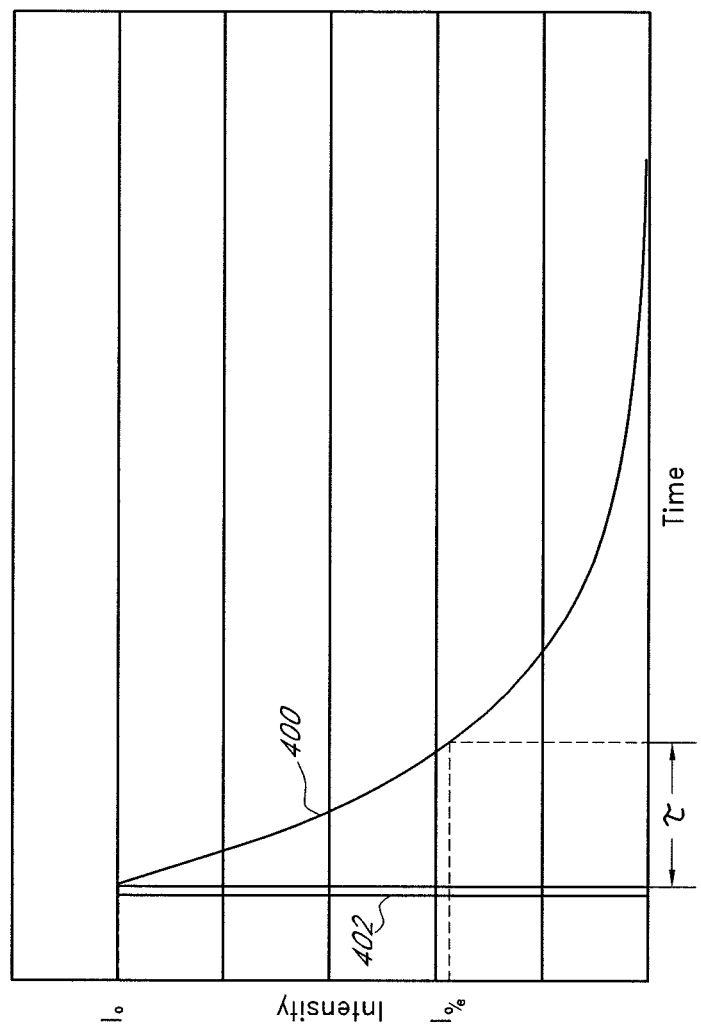
FIG. 13 shows a graph of the decay of fluorescence intensity over time after a fluorophore is subjected to a pulse of excitation light in accordance with some embodiments of the present invention.

I(t) is the fluorescence intensity at time (t), $I_0$ is the initial intensity after excitation and $\tau$ is the fluorescence lifetime which is defined as the time required for I(t) to decay to $I_0/e$. Equation 1 is applicable to a fluorophore with a single exponential decay of fluorescence and a lifetime that is substantially longer than the excitation pulse. FIG. 13 shows a graph of the decay of the fluorescent emission 400 over time after a pulse of excitation light 402. The time it takes the initial intensity, $I_0$, to drop to $I_0/e$ is equal to the lifetime, $\tau$.

An alternative method of measuring lifetime is by a frequency-domain method where the fluorophore is excited by a frequency modulated excitation light. The fluorescence lifetime, $\tau$, can be determined by measuring the phase shift of the emission from the fluorophore relative to the excitation light, or by measuring the modulation ratio, using the following equations:

$$\tau_\phi = \omega^{-1} * \tan(\phi) \quad \text{Equation 2}$$

$$\omega = 2\pi f \quad \text{Equation 3}$$

$$\tau_M = \omega^{-1} * (M^{-2} - 1)^{1/2} \quad \text{Equation 4}$$

$$M = \frac{(AC/DC)_{EM}}{(AC/DC)_{EX}} \quad \text{Equation 5}$$

Figure 14:
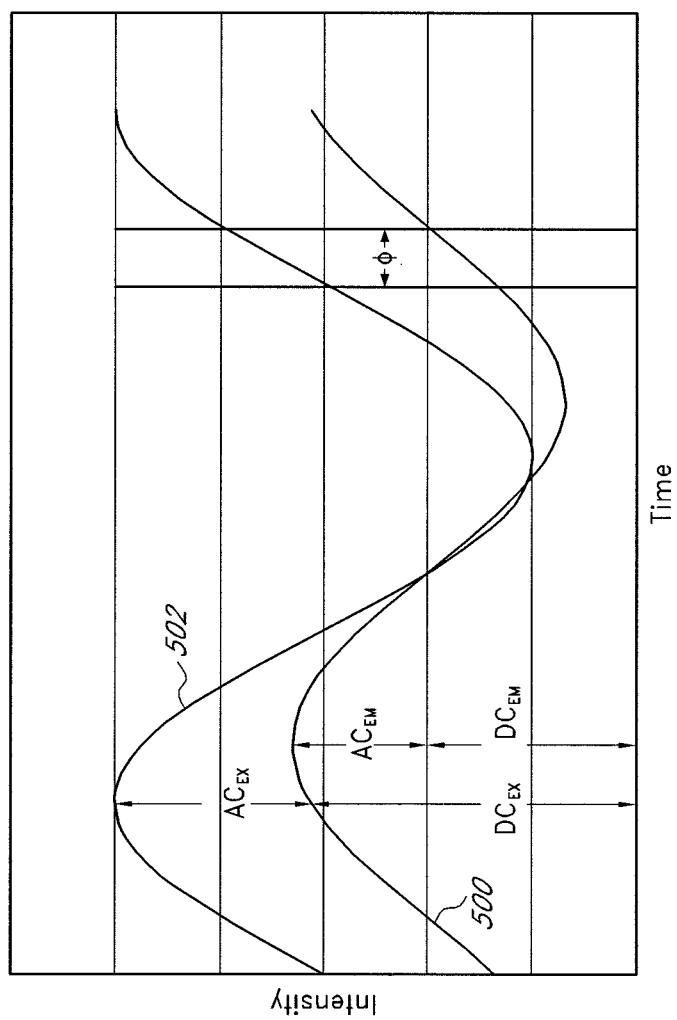
FIG. 14 shows a graph of the emission signal resulting from a frequency modulated excitation signal.

$\tau_\phi$ is the lifetime determined by measuring the phase shift, $\phi$. $\omega$ is the angular frequency of the frequency modulated excitation light and $f$ is the linear frequency. $\tau_M$ is the lifetime determined by measuring the modulation ratio, M. AC is the magnitude of the alternating portion of the signal, or the amplitude of the wave, while DC is the amplitude of the DC portion of the signal. EM refers to the emission signal, and EX refers to the excitation signal. FIG. 14 is a graph showing the relationship between the emission signal 500 and the excitation signal 502 and the variables described in Equations 2-5.

In certain embodiments, the binding assay configurations for use in an equilibrium sensor include a reversible competitive, reagent limited, binding assay, the components of which include an analyte analog and an analyte binding agent capable of reversibly binding both the analyte of interest and the analyte analog. The analyte of interest and the analyte analog compete for binding to the same binding site on the analyte binding agent. Such competitive binding assay configurations are well known in the art of clinical diagnostics and are described, by way of example, in The Immunoassay Handbook, ed. David Wild, Macmillan Press 1994. Suitable analyte binding agents for use in the assay would include antibodies or antibody fragments which retain an analyte binding site (e.g. Fab fragments), lectins (e.g. concanavalin A), hormone receptors, drug receptors, aptamers and molecularly-imprinted polymers. Preferably the analyte analog should be a substance of higher molecular weight than the analyte such that it cannot freely diffuse out of the sensor. For example, an assay for glucose might employ a high molecular weight glucose polymer such as dextran as the analyte analog.

Suitable optical signals which can be used as an assay readout in accordance with the invention include any optical signal which can be generated by a proximity assay, such as those generated by fluorescence resonance energy transfer, fluorescence polarisation, fluorescence quenching, phosphorescence technique, luminescence enhancement, luminescence quenching, diffraction or plasmon resonance.

In some embodiments of the sensor of the invention incorporates a competitive, reagent limited binding assay which generates an optical readout using the technique of fluorescence resonance energy transfer. In this assay format the analyte analog is labelled with a first chromophore and the analyte binding agent is labelled with a second chromophore. One of the first and second chromophores acts as a donor chromophore and the other acts as an acceptor chromophore. It is an important feature of the assay that the fluorescence emission spectrum of the donor chromophore overlaps with the absorption spectrum of the acceptor chromophore, such that when the donor and acceptor chromophores are brought into close proximity by the binding agent a proportion of the energy which normally would produce fluorescence emitted by the donor chromophore (following irradiation with incident radiation of a wavelength absorbed by the donor chromophore) will be non radiatively transferred to the adjacent acceptor chromophore, a process known in the art as FRET, with the result that a proportion of the fluorescent signal emitted by the donor chromophore is quenched and, in some instances, that the acceptor chromophore emits fluorescence. Fluorescence resonance energy transfer will generally only occur when the donor and acceptor chromophores are brought into close proximity by the binding of analyte analog to analyte binding agent. Thus, in the presence of analyte, which competes with the analyte analog for binding to the analyte binding agent, the amount of quenching is reduced (resulting in a measurable increase in the intensity of the fluorescent signal emitted by the donor chromophore or a fall in the intensity of the signal emitted by the acceptor chromophore) as labelled analyte analog is displaced from binding to the analyte binding agent. The intensity or lifetime of the fluorescent signal emitted from the donor chromophore thus correlates with the concentration of analyte in the fluid bathing the sensor.

An additional advantageous feature of the fluorescence resonance energy transfer assay format arises from the fact that any fluorescent signal emitted by the acceptor chromophore following excitation with a beam of incident radiation at a wavelength within the absorption spectrum of the acceptor chromophore is unaffected by the fluorescence resonance energy transfer process. It is therefore possible to use the intensity of the fluorescent signal emitted by the acceptor chromophore as an internal reference signal, for example in continuous calibration of the sensor or to monitor the extent to which the sensor has degraded and thus indicate the need to replace the sensor. As the sensor degrades, the amount of acceptor chromophore present in the sensor will decrease and hence the intensity of fluorescent signal detected upon excitation of the acceptor chromophore will also decrease. The fall of this signal below an acceptable baseline level would indicate the need to implant or inject a fresh sensor. Competitive binding assays using the fluorescence resonance energy transfer technique which are capable of being adapted for use in the sensor of the invention are known in the art. U.S. Pat. No. 3,996,345 describes immunoassays employing antibodies and fluorescence resonance energy transfer between a fluorescer-quencher chromophoric pair. Meadows and Schultz (Anal. Chim. Acta (1993 280: pp 21-30) describe a homogeneous assay method for the measurement of glucose based on fluorescence resonance energy transfer between a labelled glucose analog (FITC labelled dextran) and a labelled glucose binding agent (rhodamine labelled concanavalin A). In all of these configurations the acceptor and donor chromophores/quenchers can be linked to either the binding agent or the analyte analog.

Fluorescence lifetime or fluorescence intensity measurements may be made. As described in Lakowitz et al, Analytica Chimica Acta, 271, (1993), 155-164, fluorescence lifetime may be measured by phase modulation techniques.

Figure 15A:
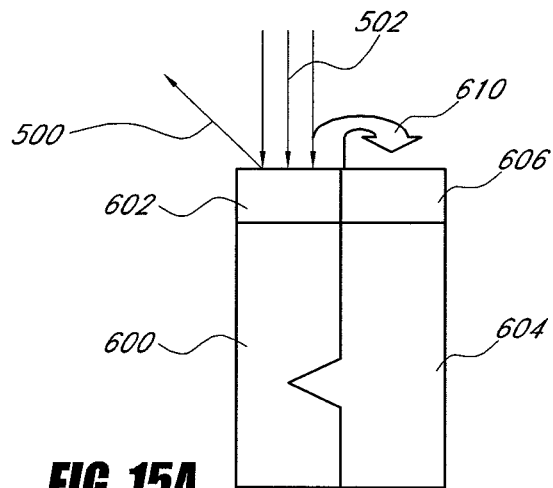
FIGS. 15A-C show the interaction between a glucose binding molecule linked to a fluorophore, a glucose analog linked to an acceptor and a glucose molecule in accordance with some embodiments of the present invention.
Figure 15B:
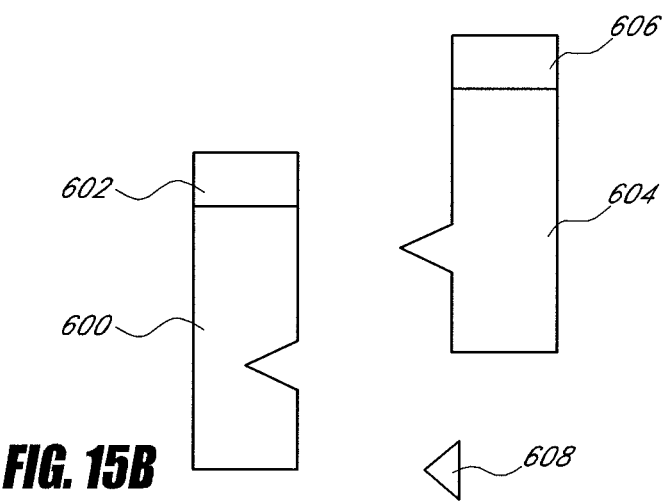
Figure 15C:
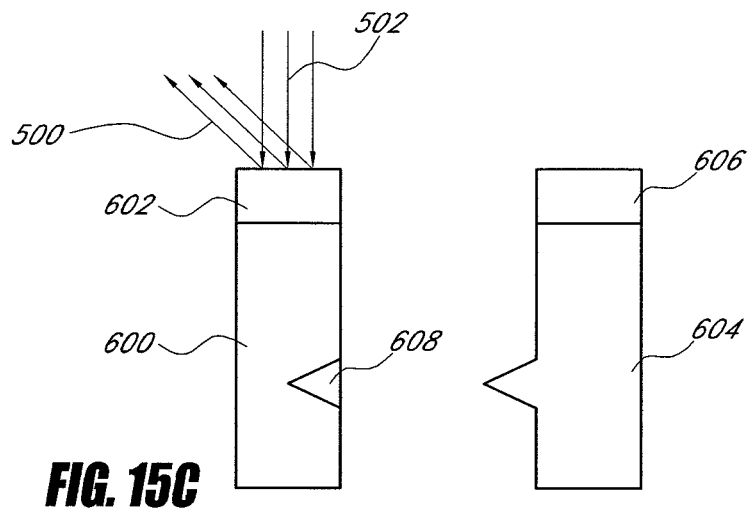

In some embodiments as shown in FIGS. 15A, 15B and 15C, a competitive binding system to measure glucose using FRET comprises a glucose binding molecule 600 linked to a donor fluorophore 602 and a glucose analog 604 linked to an acceptor molecule 606. The glucose binding molecule 600 is capable of binding with both glucose 608 and the glucose analog 604. As shown in FIG. 15A, when the glucose analog 604 is bound to the glucose binding molecule 600, the fluorescent emission 500 from the fluorophore 602 is reduced in magnitude and shifted in phase and lifetime by FRET 610 because the fluorophore 502 is in close proximity to the acceptor 606. In other embodiments, the fluorophore 602 is linked to the glucose analog 604 and the acceptor 606 is linked to the glucose binding molecule 600.

As shown in FIG. 15B, glucose 608 competes with the glucose analog 604 for the binding site on the glucose binding molecule 600. As shown in FIG. 15C, the glucose molecule 608 can displace the glucose analog 604 from the glucose binding molecule 600 so that the acceptor 606 does not alter the emission lifetime 500 of the fluorophore 602 via FRET 610.

In a system where there is a certain concentration of glucose binding molecules, glucose analogs and glucose molecules, an equilibrium will exist between the number of bound glucose molecules to the number of bound glucose analogs. A change in the number of glucose molecules in the system, changes the equilibrium between bound glucose molecules to bound glucose analogs. This in turn changes the mean lifetime of the fluorophore emission.

In some preferred embodiments, the system is excited by a frequency modulated excitation light less than approximately 1 MHz, between approximately 1 to 200 MHZ, or greater than approximately 200 MHz. In some embodiments, the frequency is approximately 0.05, 0.1, 1, 10, 20, 30, 40, 50, 60, 70, 80, 90, 100, 110, 120, 130, 140, 150, 160, 170, 180, 190 or 200 MHz. By measuring the degree of the phase shift of the system, an average FRET induced phase shift for the system can be determined which corresponds to an average lifetime value for the system as defined by Equations 2 and 3 described above. Both the phase shift and the lifetime values can be correlated to the glucose concentration. The magnitude of the phase shift is independent of the amplitude of the emission.

In other embodiments, the system is excited by a pulse and the decay of the fluorescence is measured over time. The lifetime can be determined using Equation 1 described above, and glucose concentration can be correlated to the lifetime value.

In some embodiments, the glucose binding molecule with a donor fluorophore and the glucose analog with an acceptor can be substantially immobilized in the hydrogel described above such that diffusion of the glucose binding molecule and the glucose analog out of the hydrogel is substantially reduced. In addition, the sensor is configured to provide excitation light at a wavelength absorbed by the donor fluorophore as described above. In some embodiments, the excitation light is provided as a short pulse from a laser or a light emitting diode (LED). In other embodiments, the excitation light is frequency modulated. In some embodiments, the frequency modulated excitation light is provided by a laser. In some embodiments the frequency modulated excitation light is provided by a LED. The sensor also has a detector that detects the amplitude of the emission over time and/or the phase shift of the emission and/or the amplitudes of the AC and DC portions of the emission and excitation light. The detector can be a photodetector or multiple photodetectors. The excitation and emission light can be transmitted throughout the sensor via optical fibers.

In some embodiments, the sensor can be introduced into a patient's blood vessel, such as a vein, artery or capillary, for measuring the intravascular concentration of an analyte in the patient's blood. In some embodiments, the chemistry used to measure the concentration of the analyte is based on a correlation of fluorescence intensity of a fluorophore to analyte concentration, as described above in more detail. In some embodiments, the chemistry used to measure the concentration of the analyte is based on a correlation of fluorescence lifetime of a fluorophore to analyte concentration, as described above in more detail. In some embodiments, the sensor is used to measure the concentration of glucose.

Tight Glycemic Control—Van Den Berghe Studies

In a prospective clinical study, Van Den Berghe (US 2002/0107178) tested the hypothesis that the incidence of CIPNP can be reduced by more strict metabolic using intensive insulin treatment from admission onward. Between Feb. 2 and Apr. 25, 2000, 400 patients were included in the study. They had been randomly allocated to one of two insulin (Actrapid H M NovoLet of Novo Nordisk) treatment schedules:

(1) insulin infusion started at a dose of 1 U/h only when blood glucose is >230 mg/dL (13 mmol/L) and titrated up (2 to 4 hourly controls of blood glucose levels) with increments of 0.5 to 1 U/h to keep blood glucose below this level [180-200 mg/dL (10.3-11.2 mmol/L)]. When blood glucose levels reach 180 mg/dL, insulin infusion is stopped.

(2) insulin infusion started when blood glucose is >120 mg/dL (6.8 mmol/L) at a dose of 2 U/h and titrated up (2 to 4 hourly controls of blood glucose levels) with increments adequate to keep blood glucose levels normal and thus below this level [80-110 mg/dL (4.6-6.1 mmol/L)]. Maximal hourly insulin dose is set at 60 U per hour. When blood glucose levels reach 80 mg/dL, insulin infusion is tapered and eventually stopped until normal levels are again reached. During interruption of enteral tube feeding for determination of residual stomach content, insulin infusion is reduced proportionately to the reduction of caloric intake.

(3) Concomitantly, patients were fed, on the admission day using a 20% glucose infusion and from day 2 onward by using a standardized feeding schedule consisting of normal caloric intake (25-35 Calories/kgBW/24 h) and balanced composition (20%-40% of the non-protein Calories as lipids & 1-2 g/kgBW/24 h protein) of either total parenteral, combined parenteral/enteral or full enteral feeding, the route of administration of feeding depending on assessment of feasibility of early enteral feeding by the attending physician. All other treatments, including feeding regimens, were according to standing orders currently applied within the ICU.

Exclusion criteria were age <18 y, pregnancy and not being intubated at admission.

When patients were still treated in the ICU after 7 days, a weekly EMG examination was performed to screen for the presence of CIPNP. The EMGs were always interpreted by the same expert in electrophysiology. In order to accurately assess ICU stay, which is often determined by other factors than the patient's condition—e.g. bed availability on the wards—"end of ICU stay" was defined as the day on which the attending physician considers the patient to be "ready for discharge".

A total of 83 patients ended up being treated on the ICU for at least one week and were screened by EMG for the presence of CIPNP. In the group randomized into the "intensive insulin schedule", 38 patients stayed for more than 7 days and in the group randomised into the "restrictive insulin schedule", 45 patients stayed more than 7 days. Fifteen out of 38 long-stay ICU patients in the intensive insulin group (or 39% of the long stayers) revealed a positive EMG for CIPNP at any time during the ICU stay versus 30 out of 45 in the restrictive insulin group (or 67%) (P=0.01 with Chi-square). In the intensive insulin group, the mean+SD number of positive EMGs for CIPNP per patient was 0.9±1.8 (median of zero) versus 1.8±2.1 (median of 1) in the restrictive insulin group (P=0.015 with Mann-Whitney U test).

Long-stay patients in the intensive insulin group had a CIPNP-free time on the ICU of 2.1±1.8 weeks versus 1.1±1.2 weeks in the restrictive insulin group (P=0.004 with unpaired Student's t-test).

ICU-mortality was not detectably different between the two treatment groups (P=0.4).

Van Den Berghe concluded that the study revealed that strict metabolic control with intensive insulin treatment and clamping of blood glucose levels within normal limits significantly reduces the incidence of CIPNP and lengthens the time free of CIPNP in patients that do develop this problem. This was the first study to point to a preventive strategy for this frequently occurring and important problem in ICU patients. Since the presence of EMG-proven CIPNP has been shown to extend the need for ICU support and to prolong the time required for rehabilitation, this treatment will lead to a reduction in need for ICU support and to a shorter time for rehabilitation, which could reflect a major reduction in costs.

Van Den Berghe also conducted a prospective, randomized, controlled study. All mechanically ventilated, adult patients admitted to the intensive care unit (ICU) were eligible for inclusion. Only 5 patients participating in another trial and 9 who were moribund or DNR coded at ICU admission were excluded. At admission, patients were randomized to either strict normalization of glycemia (4.5-6.1 mmol/L) with continuously infused insulin during intensive care, the 'intensive insulin schedule' (IIS), or the currently used 'restrictive insulin schedule' (RIS), with insulin started when blood glucose exceeds 12 mmol/L in which case glycemia is clamped to 10-12 mmol/L. An interim safety analysis revealed a difference in mortality, and the study was ended for ethical reasons.

A total of 1548 patients were included, 765 in the IIS group, 783 in the RIS group, well matched at inclusion. IIS reduced ICU mortality by 43% (P=0.005) [63 deaths in the RIS group versus 35 in the IIS group; death odds ratio for IIS, corrected for all baseline univariate predictors of ICU death, was 0.52 (0.33-0.82), P=0.004] and hospital mortality by 34% (P=0.01). Mortality reduction occurred exclusively in long-stay ICU patients and was due to prevention of death from multiple organ failure with sepsis. IIS also reduced the incidence of blood stream infections, renal failure, anemia and critical illness polyneuropathy as well as the need for dialysis or hemofiltration, red cell transfusion, prolonged mechanical ventilatory support and intensive care. Further details of the clinical study are disclosed in US 2002/0107178; incorporated herein in its entirety by reference thereto.

According to Van Den Berghe, the data suggested that disturbances in glucose metabolism during critical illness are not "adaptive and beneficial" since strict metabolic control with exogenous insulin substantially reduces morbidity and mortality.

The primary outcome measure in the Van Den Berghe study was death from all causes during intensive care. Secondary outcome measures were in-hospital mortality, incidence of prolonged intensive care dependency and need for ICU re-admission, need for vital organ system support comprising mechanical ventilatory support, renal replacement therapy (continuous or intermittent hemofiltration or dialysis), inotropic or vasopressor support, incidence of critical illness polyneuropathy, the degree of inflammation, incidence of blood stream infections and use of antibiotics, transfusion requirements and incidence of hyperbilirubinemia. Furthermore, use of intensive care resources was analyzed by cumulative TISS scores. In order to accurately and objectively assess duration of ICU stay, which is often influenced by non-patient related factors such as bed availability on regular wards, patients were defined 'dischargable from ICU' when they were no longer in need of vital organ system support and received at least ⅔rd of the caloric need through the normal enteral route or earlier when actually sent to a ward.

Van Den Berghe reported another study involving 1548 patients, 783 in the RIS group and 765 in the IIS group, well matched at randomization although IIS patients tended to be slightly older and more obese compared with RIS patients. A history of diabetes was present in 13.2% of patients, 4.6% treated with subcutaneous insulin injections, 8.6% receiving oral anti-diabetic treatment. On ICU admission, 74.6% of patients revealed glycemia higher than normal when compared with overnight fasted reference values ($\geq 6.1$ mmol/L) and 56% had a blood glucose level higher than the fasted diabetes threshold ($\geq 7$ mmol/L). Only 11.7%, however, revealed an on-admission glycemia in the non-fasting diabetes range ($\geq 11$ mmol/L). A non-fasting "diabetic" glycemia on ICU admission did not correlate well with having a history of diabetes, as only 19.6% of the known diabetics revealed a blood glucose level on ICU admission $\geq 11$ mmol/L. The two study groups were comparable for diabetes diagnosed before ICU admission and for incidence of on-admission hyperglycemia.

Mean and maximal amount of non-protein Calories per patient (not including the first and last day of ICU stay) was 19±7 kCal/kg/24 h and 24±10 kCal/kg/24 h, respectively. Mean and maximal amount of dietary nitrogen was 0.14±0.06 gN/kg/24 h and 0.19±0.08 gN/kg/24 h, respectively. Daily amounts and composition of the feeding regimens were comparable in the two groups.

In the IIS group, 99% of patients required exogenous insulin, a need which persisted for the entire duration of ICU stay. Glycemia was well controlled with mean morning levels of 5.8±1.0 mmol/L. Only 0.1% of IIS patients had blood glucose levels that failed to go below 6.1 mmol/L within 48 h, 48% never exceeded 6.1 mmol/L after treatment initiation and only 17% occasionally peaked over 8.4 mmol/L. Mean morning glycemia in the RIS group was 8.5±1.8 mmol/L. Only 39% of RIS patients actually received insulin and those revealed a mean morning glycemia of 9.6±1.8 mmol/L in contrast to 7.8±1.4 mmol/L in the non-insulin requiring RIS patients.

In 39 IIS-treated patients, glycemia transiently fell below 2.3 mmol/L versus 6 patients in the RIS group. Such an event of hypoglycemia was always quickly corrected and never induced serious symptoms such as hemodynamic deterioration or epilepsia.

In the IIS group, 35 patients (4.6%) died during intensive care versus 63 (8.1%) in the RIS group (P=0.005), a relative risk reduction (RRR) of 43%. The "numbers needed to treat" (NNT) to save one life during intensive care was 29. The impact on ICU mortality by IIS was independent of the first 24 h-APACHE II and TISS scores. The intervention effect was also similar in patients after cardiac surgery and those suffering from other types of critical illness. ICU mortality among the RIS patients actually receiving insulin was 12.4% versus 5.2% among those not requiring insulin to keep glycemia below 12 mmol/L (P=0.0003).

Since it was hypothesized that a difference in mortality among long-stay ICU patients, Van Den Berghe's group sub-analyzed the effect in patients with an ICU stay of $\leq 5$ days and in those staying >5 days. First 24 h-APACHE II score of patients staying $\leq 5$ days was a median 9 (IQR 6-12) and 75% of them were patients after cardiac surgery. Median first 24 h-APACHE II in patients staying >5 days was 12 (8-15) and 68% were suffering from a non-cardiac surgery type of critical illness. The number of patients with an ICU stay of >5 days was not statistically different in the IIS (27%) and RIS (31%) groups (P 0.1). Mortality of patients staying $\leq 5$ days was similar in IIS and RIS groups. Hence, the reduction in ICU mortality by IIS occurred selectively in the prolonged critically ill cohort with an absolute and relative risk reduction of 9.6% and 47%, respectively, and one life saved for every 11 treated long-stay patients.

All on-admission risk factors for ICU mortality were determined using univariate analysis. These comprised the first 24 h-APACHE II score, age, a non-cardiac surgery type of critical illness, tertiary referral, history of malignancy, and on-admission blood glucose level $\geq 11$ mmol/L. These factors were subsequently entered into a multivariate logistic regression model together with the randomized insulin schedule. This revealed that the independent risk factors for mortality were the first 24 h-APACHE II score, age, a noncardiac surgery type of critical illness, tertiary referral and insulin treatment schedule. The death odds ratio for IIS, corrected for other baseline univariate predictors of ICU death, was 0.52 (95% confidence intervals 0.33-0.82). Analysis of the causes of death during intensive care revealed that IIS particularly reduced the risk of death from multiple organ failure with a proven septic focus on post-mortem examination.

IIS also significantly reduced total in-hospital mortality from 10.8% to 7.1% (P=0.01), a relative risk reduction of 34%. Again, this benefit was limited to the prolonged critically ill cohort.

IIS reduced duration of ICU stay whereas in-hospital stay was not detectably different between the two study groups. ICU re-admission rate was 2.1% and similar in both groups. In the IIS group, significantly less patients required prolonged mechanical ventilatory support and renal replacement therapy compared with the RIS group, whereas the need for inotropic or vasopressor support was identical. Independent of renal replacement therapy, kidney function parameters were more disturbed in the RIS group. The incidence of hyperbilirubinemia was significantly lower in the IIS group.

There was a 46% reduction in blood stream infections. Moreover, markers of inflammation were less disturbed and prolonged use of antibiotics (>10 days) less often required in the IIS group. The latter was largely attributable to the effect on bacteremia (75% of bacteremic patients were treated with antibiotics for >10 days versus 10% of non-bacteremic patients; P<0.0001). Mortality tended to be lower in bacteremic IIS patients (12.5%) compared with bacteremic RIS patients (29.5%; P=0.067). There was no difference between the two groups in the use of ICU drugs other than insulin or antibiotics.

Patients with an ICU stay of more than 1 week were screened weekly for critical illness polyneuropathy. Firstly, due to the effect on ICU stay, less IIS patients were screened. Secondly, among the screened patients in the IIS group, less revealed a positive EMG compared with the RIS group. Among screened patients, the NNT to prevent critical illness polyneuropathy in one patient was 4. Furthermore, critical illness polyneuropathy resolved more rapidly in the IIS group, as indicated by a lower fraction of patients with repetitive positive EMGs on the weekly screenings.

The use of aminoglycosides and glucocorticoids were determinants of critical illness polyneuropathy by univariate analysis. However, when entered into a multivariate logistic regression model together with other univariate predictors, the only independent determinants of critical illness polyneuropathy remained restrictive insulin schedule [or of 2.6 (1.6-4.2); P=0.0002], >3 days vasopressor treatment [or of 2.5 (1.4-4.2); P=0.001], acquiring a blood stream infection [or of 2.3 (1.3-4.1); P=0.006] and receiving renal replacement therapy [or of 1.9 (1.0-3.8); P=0.05].

When the risk of critical illness polyneuropathy was evaluated in both study groups as function of the actual mean glycemia per patient, a positive, linear correlation was obtained.

The amount of red cell transfusions in IIS patients was only half that of RIS patients. This was not due to a more liberal transfusion strategy in RIS patients as indicated by their lower levels of hemoglobin and hematocrit.

The cumulative TISS score is an indicator of the number of therapeutic interventions per patient and per ICU stay. There was a 20% reduction in median cumulative TISS score selectively in long-stay patients. In view of a comparable TISS score on the last day of study [median of 30 (26-38) in both study groups], this difference reflects a 20% reduction in costs per long-stay ICU patient.

In this large prospective, randomized, controlled study of intensive care-dependent critically ill patients, tight glycemic control below 6.1 mmol/L with insulin reduced ICU mortality by 43% and in-hospital mortality by 34%. Strict metabolic control also substantially improved morbidity by preventing blood stream infections, renal failure, anemia, critical illness polyneuropathy and need for prolonged support of failing vital organ systems. These striking benefits were independent of the type and severity of underlying disease.

The beneficial effects on morbidity can be summarized as reducing the risk of several key problems in intensive care. These include acquiring severe infections and ensuing inflammatory response, development of renal failure, cholestasis, anemia, critical illness polyneuropathy and muscle weakness. These problems perpetuate the need for intensive care which, in view of the high mortality of prolonged critical illness, often becomes futile.

In conclusion, the data suggest that disturbances in glucose metabolism in critically ill patients are not "adaptive and beneficial" since strict glycemic control during intensive care substantially reduces morbidity and mortality.

Use of Intravascular Equilibrium Sensor to Achieve Tight Glycemic Control

The Van Den Berghe data and conclusions described above, as well as earlier publications from Furnary and colleagues (see e.g., Zerr et al., Ann Thorac Surg 1997 63:356-361), suggest that tight glycemic control may significantly reduce complications, shorten ICU stays, and improve outcome. Unfortunately, despite the significant benefits, it is still considered acceptable clinical ICU practice to allow blood glucose levels to increase as high as to 250 mg/dL or above before intervention. The reasons that medical and ICU personnel are disinclined to try to tightly regulate blood glucose in critically ill patients, e.g., within preferred target concentrations of about 80 to 110 mg/dl, are several fold. First, some practitioners believe that high levels of blood glucose may be part of the adaptive stress responses and that low blood glucose levels during stress is potentially deleterious for the immune system and for healing (Mizock B A. Am J Med 1995; 98: 75-84). As a practical matter, without continuous glucose monitoring and a reliable indication of the rate and direction (rising or falling) of changes in blood glucose concentration following insulin administration, ICU staff are inclined to err on the side of tolerating relative hyperglycemia rather than risk acute hypoglycemia induced by insulin. In view of the foregoing, Applicants have postulated that the clinical benefits of tight glycemic control in the critically ill ICU patient may be facilitated and enhanced by use of an intravascular glucose sensor capable of accurate continuous glucose monitoring, wherein the blood glucose concentrations are corrected for changes in pH, and wherein the sensor is operably coupled to a monitor in which the rate and direction of the change in blood glucose may be displayed.

Thus, in accordance with a preferred embodiment of the present invention, a method is disclosed for achieving tight glycemic control in a patient in need thereof (preferably in a patient under care in an intensive care unit), wherein the tight glycemic control is sufficient to reduce the incidence and/or severity of at least one critical illness polyneuropathy or other complication. The method comprises deploying an equilibrium glucose sensor within a blood vessel in the patient; operably coupling the sensor to a monitor that displays the blood glucose concentration and the rate and direction of changes in blood glucose concentration, and optionally generates an alarm signal when the blood glucose concentration and/or rate and direction of change varies outside of a predetermined range; and administering a blood glucose regulator when the blood glucose concentration varies outside of the predetermined range, wherein the blood glucose regulator is administered in an amount sufficient to return the blood glucose concentration to within the predetermined concentration range and/or reverse a rising or falling trend, thereby achieving tight glycemic control. The predetermined concentration range may be from about 60 to about 180 mg/dl glucose, more preferably from about 60 to about 130 mg/dl glucose, and yet more preferably from about 80 to about 110 mg/dl. The blood glucose regulator may be glucose or insulin or insulin analogs or derivatives, or other hypoglycemic agents, or any known agents or combinations that regulate blood glucose.

Figure 16A:
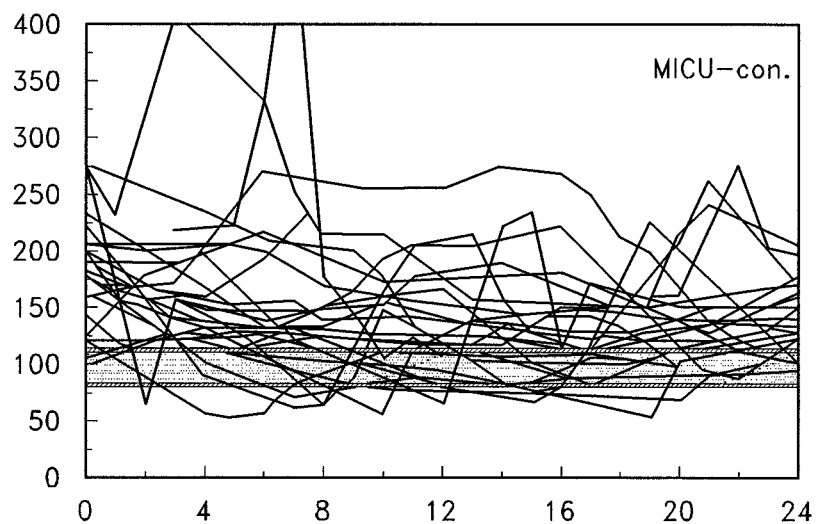
FIGS. 16A and B show blood glucose concentrations in medical and surgical ICU patient populations in a study by Mader et al. 2007 Diabetes Technology Meeting, San Francisco.
Figure 16B:
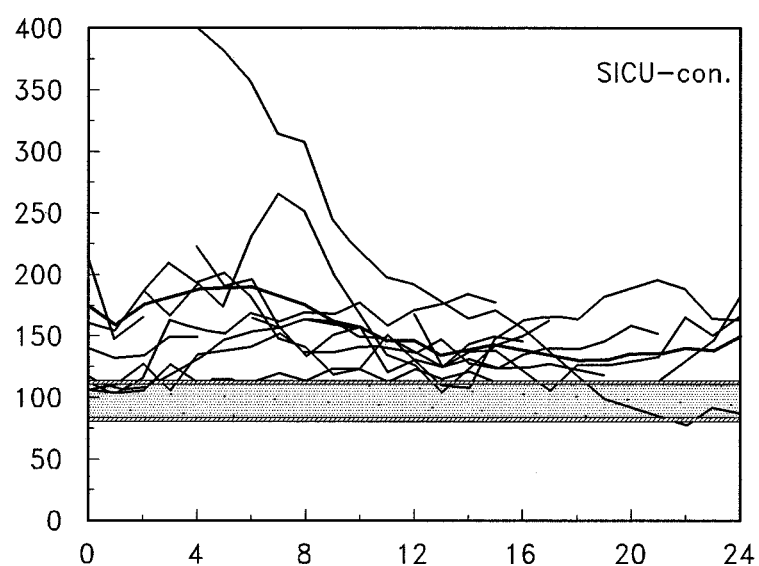

With reference to FIGS. 16A and 16B, typical blood glucose concentrations in medical ICU and surgical ICU are shown; these data are from Mader et al., Diabetes Technology Meeting, San Francisco, Calif. (2007). The shaded bar indicates the target blood glucose range (80-110 mg/dl). The thicker line represents the calculated average, and the many lines are from individual patients. Clearly, there is a great challenge in trying to achieve tight glycemic control in these patient populations, in which the blood glucose varies tremendously over time.

Figures 17A, 17B:
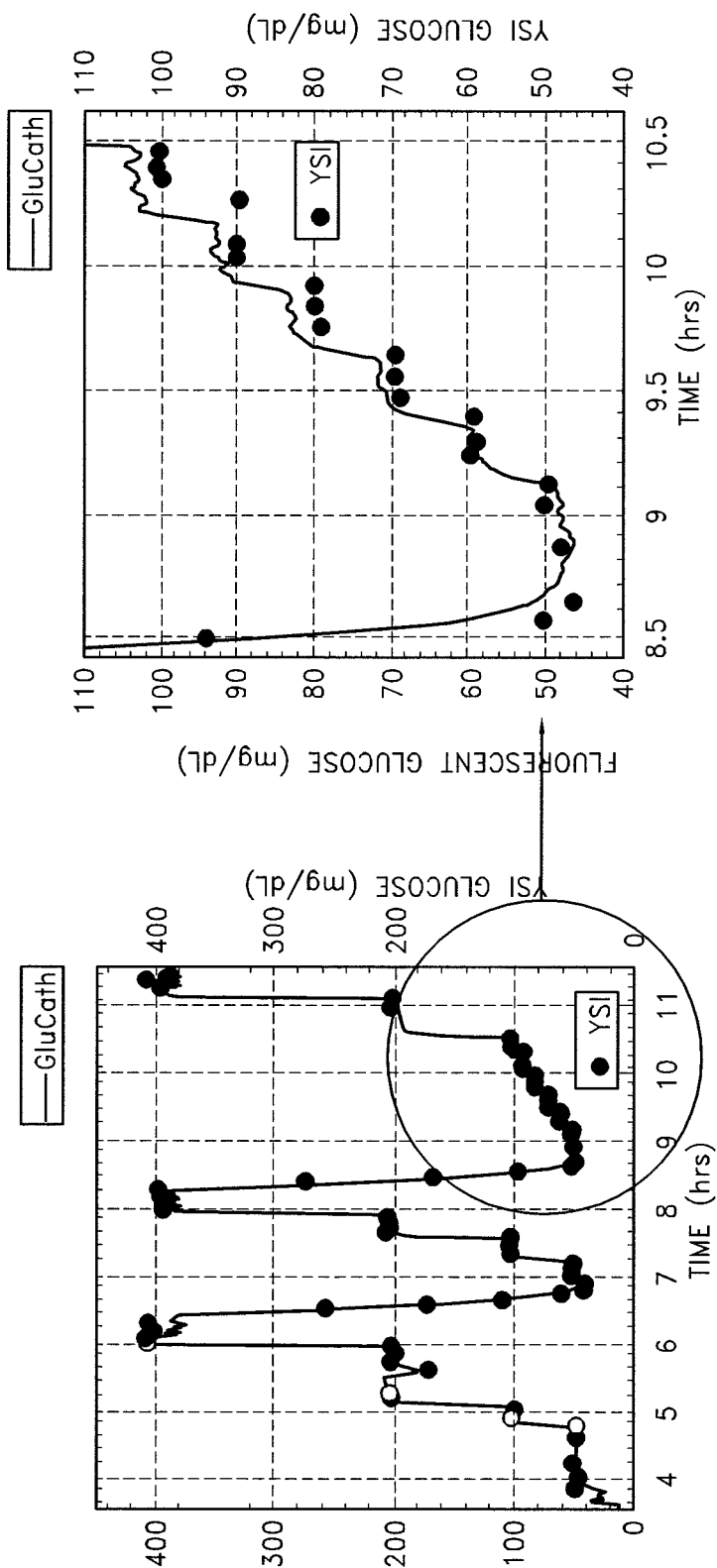
FIGS. 17A and B show a comparison of the GluCath and YSI detection methods of blood glucose in vitro in a circulating blood loop.

With reference to FIGS. 17A and B, the results of glucose determination over time and with infused glucose in a circulating blood loop in vitro are compared for a continuous glucose sensor in accordance with a preferred embodiment of the present invention (—GluCath) and the Yellow Springs Instrument glucose oxidase lab analyzer (● YSI), the gold standard of blood glucose measurements. The GluCath equilibrium fluorescence glucose sensor used in this experiment comprised HPTS-triCysMA dye and 3,3'-oBBV quencher. FIG. 17A shows an 8 hr time course with changes in circulating glucose in the range of 50-400 mg/dl. FIG. 17B is an expanded illustration of the two hr stepwise addition of 10 mg/dl boluses. The data show that the equilibrium fluorescence glucose sensor provides continuous monitoring of blood glucose which is as accurate as the YSI lab analyzer. The expanded view in FIG. 17B shows rapid and accurate sensing even at very low levels of blood glucose (between 50 and 100 mg/dl). This is surprising since accurate detection in such a low range has been extremely difficult to accomplish with other detection devices. The lack of accurate and reliable blood glucose sensing below 100 mg/dl has hampered ICU attempts to maintain target blood glucose levels, because of the significant clinical risk of going too low.

Figure 18A:
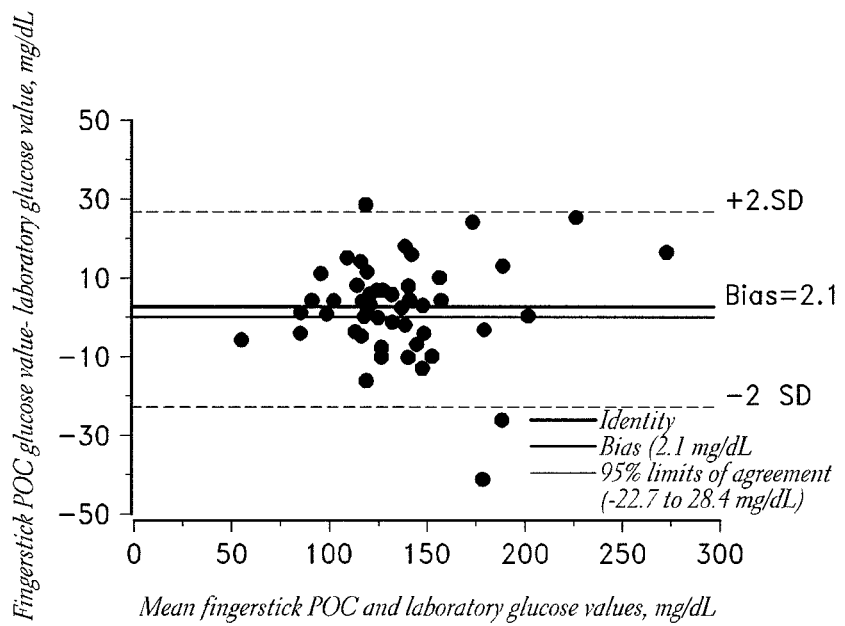
FIGS. 18A and B show Bland-Altman difference plots comparing laboratory references of SureStep Pro Fingerstick and GluCath equilibrium fluorescent glucose sensor. The GluGath sensor is positioned in the right jugular vein of sheep.
Figure 18B:
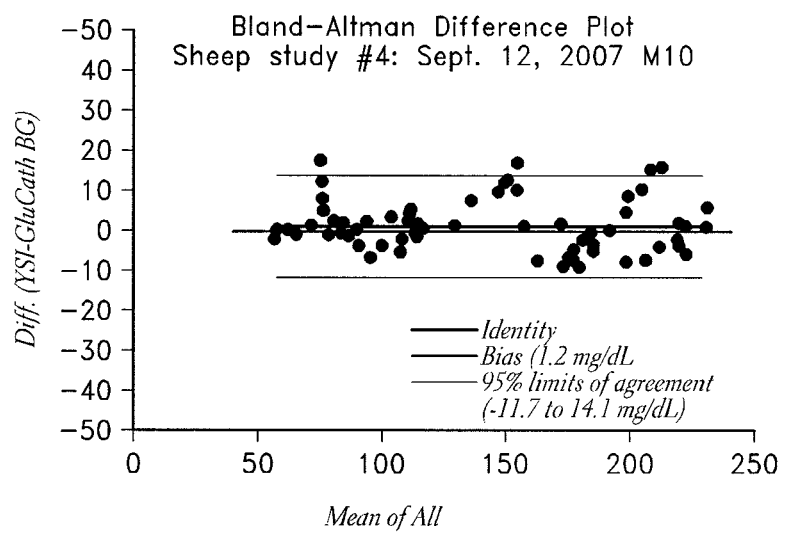

With reference to FIGS. 18A and B, Bland-Altman plots show differences between laboratory references and either fingerstick POC (FIG. 18A) or GluCath indwelling equilibrium fluorescence glucose sensor (FIG. 18B) for in vivo blood glucose monitoring. FIG. 18A shows results of blood glucose detection using a standard fingerstick test compared to a clinical chemistry system. The 95% confidence limits vary from −22.7 to 28.4 mg/dl with a bias of 2.1 mg/dl. It is noteworthy that very few readings below 100 mg/dl can be seen. FIG. 18B shows results of blood glucose detection using GluCath continuous equilibrium fluorescence glucose sensor, deployed intravascularly in sheep compared to the YSI lab analyzer. The differences are much tighter, with 95% confidence limits of −11.7 to 14.1 mg/dl and a bias of only 1.2 mg/dl. There are many more data points below 100 mg/dl.

EXAMPLE

A 65 year old male is admitted to an intensive care unit following open heart surgery. After he is settled, a GluCath optical fiber sensor is deployed intravascularly. The sensor comprises an HPTS-tri-CysMA dye operably coupled to a 3,3'-oBBV quencher, immobilized within a hydrogel disposed along the distal region of the optical fiber sensor. The proximal end of the sensor is coupled to a light source and a programmable monitor adapted to display continuous real-time glucose concentration as well as rates and directions of changes in blood glucose levels. The monitor is programmed to generate an alarm when the blood glucose falls outside of the target range (below 80 mg/dl or above 110 mg/dl). Continuous readout of the rate and direction of blood glucose trend and blood glucose concentration allows ICU staff to determine whether intervention is needed. As soon as the sensor goes on-line, the blood glucose concentration reads out on the monitor at 300 mg/dl and is rising. An ICU nurse administers insulin at a dose calculated to reduce the blood glucose level to within the target range. Within a few minutes the blood glucose begins to drop. The physician is concerned that the glucose will drop too fast and overshoot the target low concentration of 80 mg/dl. Within two hours, the blood glucose concentration is at 100 mg/dl and is steady. After several hours of routine care, the blood glucose concentration begins to rise. When the glucose concentration goes above 110 mg/dl, the alarm on the monitor alerts the ICU staff to the rising glucose level. An ICU nurse administers an amount of insulin sufficient to reduce the blood glucose to within the programmed range. The ICU staff is able to maintain tight control of the patient's blood glucose concentration during the next 7 days in the ICU. The recovery is smooth and no critical illness polyneuropathy or other complications are observed.

While a number of preferred embodiments of the invention and variations thereof have been described in detail, other modifications and methods of using and medical applications for the same will be apparent to those of skill in the art. Accordingly, it should be understood that various applications, modifications, and substitutions may be made of equivalents without departing from the spirit of the invention or the scope of the claims.

What is claimed is:

1. A method for continuously monitoring blood glucose concentration in an ICU patient in need thereof, comprising:
deploying an equilibrium glucose sensor in the patient, wherein the equilibrium glucose sensor comprises an indicator system comprising a fluorophore and a glucose binding moiety, wherein the indicator system is configured to generate an optical signal related to the blood glucose concentration; and
coupling the sensor to a monitor configured to detect the optical signal, and determine and display the ICU patient's blood glucose concentration, and a rate and direction of change in the blood glucose concentration.

2. The method of claim 1, further comprising administering a blood glucose regulator when the displayed blood glucose concentration varies outside of a predetermined concentration range.

3. The method of claim 2, wherein the blood glucose regulator is administered in an amount sufficient to return the blood glucose concentration to within the predetermined concentration range.

4. The method of claim 2, wherein the blood glucose regulator is administered by operator action.

5. The method of claim 2, wherein the blood glucose regulator is administered by an ICU staff member.

6. The method of claim 2, wherein an alarm signal is generated when the blood glucose concentration varies outside of the predetermined concentration range.

7. The method of claim 2, wherein the blood glucose regulator is administered in an amount sufficient to reverse a rising or falling trend in the blood glucose concentration.

8. The method of claim 2, wherein the predetermined concentration range is from about 60 to about 180 mg/dl glucose.

9. The method of claim 8, wherein the predetermined concentration range is from about 60 to about 130 mg/dl glucose.

10. The method of claim 9, wherein the predetermined concentration range is from about 80 to about 110 mg/dl.

11. The method of claim 2, wherein the blood glucose regulator is insulin or an analog or derivative thereof.

12. The method of claim 2, wherein the blood glucose regulator is glucose.

13. The method of claim 1, wherein the equilibrium glucose sensor is deployed in a blood vessel.

14. The method of claim 1, wherein the equilibrium glucose sensor is deployed in tissue.

15. The method of claim 1, wherein glucose binding to the glucose binding moiety causes a change in fluorescence lifetime of the fluorophore, wherein said change is related to the blood glucose concentration.

16. The method of claim 1, wherein an alarm signal is generated when the rate and direction of change in the blood glucose concentration varies outside a predetermined range.

17. The method of claim 1, wherein the fluorophore is chosen from the group consisting of a fluorescent organic dye, an organometallic compound, a metal chelate, a fluorescent conjugated polymer, quantum dots or nanoparticles, and combinations of the above.

18. The method of claim 1, wherein the fluorophore is a fluorescent dye.

19. The method of claim 18, wherein the fluorescent dye is capable of being excited by light of a wavelength greater than about 400 nm.

20. The method of claim 18, wherein the fluorescent dye is stable against photo-oxidation, hydrolysis, and biodegradation.

21. The method of claim 18, wherein the fluorescent dye comprises a HPTS-triCysMA dye.

22. The method of claim 18, wherein the fluorescent dye comprises SNARF-1.

23. The method of claim 18, wherein the fluorescent dye comprises SNARL-1.

24. The method of claim 18, wherein the fluorescent dye comprises TSPP.

25. The method of claim 1, wherein the glucose binding moiety comprises a boronic acid functionalized viologen.

26. The method of claim 25, wherein the boronic acid functionalized viologen comprises 3,3'-oBBV.

27. The method of claim 1, wherein the fluorophore and the glucose binding moiety are physically immobilized within a semi-permeable membrane.

28. The method of claim 27, wherein the fluorophore and the glucose binding moiety are sufficiently greater in size than glucose so that the semi-permeable membrane allows passage of glucose but blocks passage of the fluorophore and the glucose binding moiety.

29. The method of claim 1, wherein the fluorophore and the glucose binding moiety are physically immobilized within a hydrogel matrix.

30. The method of claim 1, wherein the fluorophore and the glucose binding moiety are covalently bonded to a hydrogel matrix.

31. The method of claim 1, wherein the fluorophore and the glucose binding moiety are covalently bonded to each other.

32. The method of claim 1, wherein the equilibrium glucose sensor comprises an optical fiber.

33. The method of claim 32, wherein the optical fiber is coupled to a light source.

34. The method of claim 33, wherein the optical fiber is coupled to an emission light detector.

* * * * *